(12) United States Patent
Osborne et al.

(10) Patent No.: US 12,300,268 B2
(45) Date of Patent: May 13, 2025

(54) METHOD AND SYSTEM FOR CATEGORIZING MUSICAL SOUND ACCORDING TO EMOTIONS

(71) Applicant: X-SYSTEM LIMITED, Hampshire (GB)

(72) Inventors: Nigel Osborne, Hampshire (GB); Kit Barnes, Hampshire (GB); John Turner, Hampshire (GB)

(73) Assignee: X-SYSTEM LIMITED, Hampshire (GB)

( * ) Notice: Subject to any disclaimer, the term of this patent is extended or adjusted under 35 U.S.C. 154(b) by 568 days.

(21) Appl. No.: 16/764,601

(22) PCT Filed: Nov. 15, 2018

(86) PCT No.: PCT/GB2018/053312
§ 371 (c)(1),
(2) Date: May 15, 2020

(87) PCT Pub. No.: WO2019/097236
PCT Pub. Date: May 23, 2019

(65) Prior Publication Data
US 2020/0286505 A1   Sep. 10, 2020

(30) Foreign Application Priority Data
Nov. 15, 2017  (GB) ..................... 1718894

(51) Int. Cl.
*G10L 25/63* (2013.01)
*G06F 3/01* (2006.01)
(Continued)

(52) U.S. Cl.
CPC .............. *G10L 25/63* (2013.01); *G06F 3/011* (2013.01); *G06N 3/08* (2013.01); *G06N 7/01* (2023.01);
(Continued)

(58) Field of Classification Search
CPC .......... G10L 25/63; G10L 25/30; G06F 3/011; G06F 2203/011; G06F 16/60; G06N 3/08;
(Continued)

(56) References Cited

U.S. PATENT DOCUMENTS

| 9,736,603 B2 | 8/2017 | Osborne et al. |
| 2002/0134220 A1 | 9/2002 | Yamane et al. |

(Continued)

FOREIGN PATENT DOCUMENTS

| EP | 1703491 A1 | 9/2006 |
| GB | 2491722 A | 12/2012 |

(Continued)

OTHER PUBLICATIONS

Bai et al ("Dimensional Music Emotion Recognition by Valence Arousal Regression", 2016 IEEE International Conference on Cognitive Informaiton and Cognitive Computing. pp. 42-49) (Year: 2016).*

(Continued)

*Primary Examiner* — Michael N Opsasnick
(74) *Attorney, Agent, or Firm* — Saul Ewing LLP

(57) ABSTRACT

A computer implemented method for analysing sounds, such as audio tracks, and automatically classifying the sounds in a space in which arousal is one axis and valence is another axis. The location of a sound or track in that arousal-valence space is automatically determined using a computer implemented system that analyses, measures or infers values for each of the following base feature parameters: harmonicity, turbulence, rhythmicity, sharpness, volume and linear harmonic cost, or any combination of two or more of those parameters.

30 Claims, 38 Drawing Sheets

(51) Int. Cl.
  *G06N 3/08* (2023.01)
  *G06N 7/01* (2023.01)
  *G06N 20/00* (2019.01)
  *G10L 25/30* (2013.01)

(52) U.S. Cl.
  CPC .............. *G06N 20/00* (2019.01); *G10L 25/30* (2013.01); *G06F 2203/011* (2013.01)

(58) Field of Classification Search
  CPC .......... G06N 7/005; G06N 20/00; G10H 1/00; G10H 2210/031; G10H 2240/005; G10H 2240/075; G10H 2240/081; G10H 2240/085
  See application file for complete search history.

(56) References Cited

U.S. PATENT DOCUMENTS

| | | |
|---|---|---|
| 2004/0094019 A1 | 5/2004 | Herre et al. |
| 2004/0237759 A1 | 12/2004 | Bill |
| 2006/0200344 A1* | 9/2006 | Kosek ............ G10L 21/0208 704/226 |
| 2007/0131096 A1 | 6/2007 | Lu et al. |
| 2007/0288478 A1 | 12/2007 | Dimaria et al. |
| 2008/0201370 A1 | 8/2008 | Kemp et al. |
| 2009/0151544 A1 | 6/2009 | Eggink |
| 2010/0191037 A1 | 7/2010 | Cohen et al. |
| 2010/0282045 A1 | 11/2010 | Chen et al. |
| 2011/0106750 A1 | 5/2011 | Pradeep et al. |
| 2011/0300847 A1* | 12/2011 | Quy ............ H04W 4/00 455/419 |
| 2012/0150544 A1* | 6/2012 | McLoughlin ....... G10L 21/0364 704/262 |
| 2012/0233164 A1 | 9/2012 | Rowe et al. |
| 2014/0221866 A1* | 8/2014 | Quy ............ A61B 5/165 600/300 |
| 2014/0307878 A1* | 10/2014 | Osborne ............ G10H 1/0008 381/56 |
| 2014/0330132 A1* | 11/2014 | Raskin ............ A61B 5/02427 600/479 |
| 2015/0112232 A1* | 4/2015 | Quatieri ............ A61B 5/7264 600/595 |
| 2015/0206523 A1* | 7/2015 | Song ............ A61B 5/0077 84/609 |
| 2015/0297109 A1* | 10/2015 | Garten ............ A61B 5/316 600/28 |
| 2018/0182256 A1* | 6/2018 | Gotgart ............ G09B 7/02 |
| 2019/0201691 A1* | 7/2019 | Poltorak ............ A61B 5/0006 |
| 2020/0035337 A1* | 1/2020 | Söhne ............ A61B 5/0022 |
| 2020/0243055 A1* | 7/2020 | Grace ............ G09B 5/04 |
| 2020/0286505 A1* | 9/2020 | Osborne ............ G06N 3/08 |
| 2021/0353903 A1* | 11/2021 | Park ............ A61B 5/486 |

FOREIGN PATENT DOCUMENTS

| | | |
|---|---|---|
| JP | H07108847 B2 | 4/1995 |
| JP | H09187512 A | 7/1997 |
| JP | 2003015666 A | 1/2003 |
| JP | 2010119563 A | 6/2010 |
| JP | 2011029777 A | 2/2011 |
| WO | 2006050512 A2 | 5/2006 |
| WO | 2010027509 A1 | 3/2010 |
| WO | 2012168740 A1 | 12/2012 |

OTHER PUBLICATIONS

Bai et al., "Dimensional music emotion recognition b valence-arousal regression," 2016 IEEE 15th Intl. Conf. on cognitive Informatics & Cognitive Computing (ICCI*CC), IEEE, pp. 42-49 (Aug. 22, 2016) XP033068769.

Kostek et al., "Rough sets applied to mood of music recognition," 2016 Federated Conf. on Computer Science and INformation SYstems (FEDCSIS), Polish INformaion Processing Society, pp. 71-78 (Sep. 11, 2016) XP032994216.

International Search Report, dated Mar. 19, 2019, issued in International Application No. PCT/GB2018/053312.

Shihab Shamma, "On the role of space and time in auditory processing," Trends in Cognitive Sciences, vol. 5, No. 8, Aug. 1, 2001, pp. 340-348 XP055038877.

Tolos et al., "Mood-based navigation through large collections of musical data," Consumer Communications and Networking Conference, 2005, CCNC 2005 Second IEEE, Jan. 3, 2005, pp. 71-75 XP010787613.

Blood et al., "Intensely pleasurable responses to music correlate with activity in brain regions implicated in reward and emotion," pp. 1-6, Sep. 25, 2001.

Hermann , et al., "The Sonification Handbook", Nov. 1, 2011 (Nov. 1, 2011).

Nardelli Mimma , et al., "Recognizing Emotions Induced by Affective Sounds through Heart Rate Variability", IEEE Transactions on Affective Computing, IEEE, USA, vol. 6, No. 4, Oct. 1, 2015 (Oct. 1, 2015), pp. 385-394, ISSN: 1949-3045, DOI: 10.1109/TAFFC.2015.2432810.

Shubert Emery , et al., "The Six Emotion-Face Clock as a Tool for Continuously Rating Discrete Emotional Responses to Music", Advances in Biometrics: Intl. Conference, ICB 2007, Seoul, Korea, Aug. 27-29, 2007; Proceedings; [Lecture Notes in Computer Science; Lect.Notes Computer], Springer, Berlin, Heidelberg, Jun. 19, 2012, 1-18.

Stanford , "Pitch detection methods review," pp. 1-7, Apr. 13, 2008.

Tzanetakis , et al., "Human Perception and Computer Extraction of Musical Beat Strength," Proc. of the 5th Int. Conference on Digital Audio Effects (DAFx-02), pp. DAFX-1-5 (Sep. 26-28, 2002).

Vinoo Alluri , et al., "Large-scale brain networks emerge from dynamic processing of musical timbre, key and rhythm", Neuroimage, Elsevier, Amsterdam, NL, vol. 59, No. 4, Nov. 6, 2011 (Nov. 6, 2011), pp. 3677-3689, ISSN: 1053-8119, DOI: 10.1016/J.NEUROIMAGE.2011.11.019.

* cited by examiner

|  | 1. | 2. | 3. | 4. | 5. | 6. | 7. | 8. | 9. | 10. |
|---|---|---|---|---|---|---|---|---|---|---|
| high | | | | | | | | | | |
| Harmonicity | 0.0 | 0.02. | 0.04. | 0.06 | 0.08. | 0.1 | 0.12 | 0.14 | 0.16 | 0.18 |
| 1HzT | 0.0 | 0.07 | 0.14 | 0.21 | 0.28 | 0.35 | 0.42 | 0.49 | 0.56 | 0.63 |
| Rhythm. | 0.63 | 0.56 | 0.49 | 0.42 | 0.35 | 0.28 | 0.21 | 0.14 | 0.07 | 0.00 |
| medium | | | | | | | | | | |
| LHC | 1.80. | 1.60 | 1.40 | 1.20 | 1.0 | 0.80 | 0.60. | 0.40 | 0.20 | 0.00 |
| Sharpness | 2800 | 2600. | 2400. | 2200 | 2000. | 1800. | 1600. | 1400 | 1200. | 1000 |
| Rhythm. | 0.63 | 0.56 | 0.49 | 0.42 | 0.35 | 0.28 | 0.21 | 0.14 | 0.07 | 0.00 |
| low | | | | | | | | | | |
| LHC | 1.80. | 1.60 | 1.40 | 1.20 | 1.0 | 0.80 | 0.60. | 0.40 | 0.20 | 0.00 |
| fund | 0 | 100 | 200 | 300 | 400 | 500 | 600 | 700 | 800 | 900 |
| Volume. | -50. | -45. | -40. | -35. | -30. | -25. | -20. | -15. | -10. | -5 |
| 50HzT. | 0. | 0.04. | 0.08. | 0.12 | 0.16. | 0.2 | 0.24. | 0.28. | 0.32. | 0.36 |

FIGURE 13

Category 5 – high activation

| | | |
|---|---|---|
| Spanish Key | Bitches Brew disc 2 | duration 17.32 |
| Oleo | Half Nelson CD9 | duration 5.52 |

Category 4 – moderately high activation

| | | |
|---|---|---|
| Bye Bye Blackbird | Bye Bye Blackbird CD8 | duration 7.55 |
| Surrey with the Fringe on Top | Four CD7 | duration 9.06 |

Category 3 – normal (to high) activation

| | | |
|---|---|---|
| So What | Kind of Blue | duration 9.22 |
| Ahmad's Blues | Half Nelson CD9 | duration 7.27 |

Category 2 – moderately low activation

| | | |
|---|---|---|
| When I Fall in Love | Half Nelson CD9 | duration 4.25 |
| My Funny Valentine | My Funny Valentine CD10 | duration 5.59 |

Category 1 – low activation

| | | |
|---|---|---|
| Flamenco Sketches | Kind of Blue | duration 9.26 |
| Blue in Green | Kind of Blue | duration 5.37 |

FIGURE 32

| Category | Rising | stable | falling |
|---|---|---|---|
| 5. |  | • | • |
| 4. | • | • | • |
| 3. | • | • | • |
| 2. | • | • | • |
| 1. | • | • |  |

FIGURE 33

| Category | Rising | stable | falling |
|---|---|---|---|
| 5. | | Symphony 7 in A, Op. 92 Allegro con brio | Symphony 7 in A major Op 92 Presto – Assai Meno Presto |
| 4. | Symphony No 5 in C minor, Op. 67 Allegro con brio | | Symphony 8 in F, Op. 93 Tempo di Menuetto |
| 3. | Symphony 9 in D minor 'Ode to Joy', Op. 125 Allegro ma non Troppo, un Poco Maestoso | Symphony 6 in F major 'Pastoral', Op. 68 Awakening of cheerful feelings upon arrival in the country | Symphony 7 in A major, Op 92 Allegretto |
| 2. | Symphony 3 in E flat 'Eroica', Op. 55 Allegro con brio | | Symphony 6 in F 'Pastoral', Op. 68 Sheperds' song: cheerful and thankful feelings after the storm |
| 1. | Symphony 3 in E flat 'Eroica', Op. 55 Marcia funebre: Adagio assai | Symphony 6 in F major 'Pastoral', Op 68 Scene at the Brook | |

FIGURE 34

METHOD AND SYSTEM FOR CATEGORIZING MUSICAL SOUND ACCORDING TO EMOTIONS

CROSS REFERENCE TO RELATED APPLICATIONS

This application claims the priority of PCT/GB2018/053312, filed on Nov. 15, 2018, which claims priority to GB Application No. GB1718894.7, filed on Nov. 15, 2017, the entire contents of each of which being fully incorporated herein by reference.

BACKGROUND OF THE INVENTION

1. Field of the Invention

The field of the invention relates to a computer implemented method for analysing sound (e.g. music tracks). Sounds are automatically categorised by a computer implemented system.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Background of the Invention

There has been a huge increase in the availability of music tracks in recent years over streaming and online services. Selecting specific music tracks on the basis of the emotion that is likely to be induced in a listener is an appealing prospect, but a very complex problem to solve in practice. There are many reasons for this: for example, describing emotional states is highly subjective; different people can react very differently to the same music and can describe their experiences in very different ways. One attempt at making the description of emotion objective and systematic is the arousal-valence plane, in which different emotions are plotted in a circle that has arousal on one axis and valence on the other axis. Reference may be made to A Regression Approach to Music Emotion Recognition IEEE Transactions on Audio, Speech, and Language Processing (Volume: 16, Issue: 2, February 2008), electronic ISSN ISSN: 1558-7924.

SUMMARY OF THE INVENTION

The invention is a computer implemented method and system for analysing sounds, such as audio tracks, and automatically classifying the sounds in a space in which arousal is one axis and valence is another axis; and the location of a sound or track in that arousal-valence space is automatically determined using a computer implemented system that analyses, measures or infers values for each of the following parameters: harmonicity, turbulence, rhythmicity, sharpness, volume and linear harmonic cost, or any combination of two or more of those parameters.

This method and system predicts both arousal and valence values from objectively measurable parameters of a sound such as a music track, or part of a track, and locates them in a 2-D space that predicts the human emotional response to specific sound, track or part of a track. The method and system can be trained and verified and improved using machine learning techniques.

Optional features:
- the parameters for a sound or music track are plotted in the arousal-valence space and the location or region defined by those values predicts the emotion likely to be triggered by that sound or track.
- values of some or all of the parameters for a sound or music track are plotted in the arousal-valence space and the location or region defined by those values, e.g. the region bounded by those values, predicts the emotion likely to be triggered by that sound or track.
- the location of a sound or track in the arousal-valence space automatically determines how that sound or track is then used.
- the location of the sound or track in that in the arousal-valence space is used to automatically predict a mood or emotion to be experienced by a listener to that sound or track.
- an emotion is predicted by combining an automatically predicted arousal and valence value.
- the predicted valence value is dependent on the predicted arousal value.
- a linear regression algorithm for predicting arousal is based on a combination of one or more or all of the base feature parameters, with weightings determined by linear regressions and that predict levels of neurophysiological arousal in the listener.
- the linear regression algorithm also takes into account the genre or type of the sound or music track.
- a neural network algorithm, which takes as input some or all of the base feature parameters, is used to output both a predicted neural net arousal and neural net valance.
- an algorithm for predicting arousal is based on averaging the predicted arousal by a linear regression algorithm and a predicted neural net arousal by a neural network.
- a valence hypothesis algorithm for predicting valence is based on a combination of subjective response and Heart Rate Variability data, which predicts how positive or negative the emotions of the listener are going to be.
- a valence hypothesis algorithm using HRV (Heart Rate Variability) data is validated using empirical evidence that associates positive valence with high vagal power, as indicated by high HRV, and negative valence as low vagal power, as indicated by low HRV.
- the valence hypothesis algorithm takes as an input one or more of the base feature parameters as well as the output of the linear regression algorithms.
- the base feature parameters are one or more of the following: linear harmonic cost, volume, sharpness, rhythmicity, 50 Hz turbulence, 1 Hz turbulence, harmonicity, fundamental.
- a predicted arousal value by a linear regression algorithm is categorized into low, medium or high arousal values, which is then used by a valence hypothesis algorithm.
- the base parameters that are used in calculating a valence value depend on the predicted arousal value.
- the valence hypothesis algorithm uses look up tables based on the category of the predicted arousal value by the linear regression algorithm.
- for a high arousal value, a valence hypothesis algorithm takes the following base feature parameters as inputs: harmonicity, 1 Hz turbulence and rhythmicity.
- for a medium arousal value, a valence hypothesis algorithm takes the following base feature parameters as inputs: linear harmonic cost, sharpness and volume.

for low arousal value, a valence hypothesis algorithm takes the following base feature parameters as inputs: linear harmonic cost, fundamental, volume and 50 Hz turbulence.

an algorithm for predicting valence is based on the averaging of the neural net valence outputted by a neural network and the predicted valence generated by a valence hypothesis algorithm.

an algorithm for combining an automatically predicted arousal and valence value is based on plotting arousal and valence values on the X and Y axes of the arousal-valence space, in which the location on the arousal-valence space is associated with specific mood or emotion.

the base feature parameters and the outputs of the algorithms are averaged over one audio track.

an audio track is also classified in terms of physical activity.

the location on the arousal-valence space is associated with a specific physical activity.

the method includes the further step of automatically classifying a dataset of sounds or music in terms of their location in the arousal-valence space.

the method includes the further step of automatically classifying music in terms of physical activities.

the method includes the further step of automatically constructing a playlist in terms of a preselected or desired mood or emotion to be experienced by a listener.

the method includes the further step of automatically constructing a playlist in terms of preselected physical activity.

the method includes the further step of automatically streaming music depending on the listener's activity, such as working, exercising, driving, seeking pain relief, seeking relaxation, seeking mood enhancement.

the method includes the further step of selecting sound or music to stream or otherwise provide to someone viewing online content.

the method includes the further step of selecting sound or music to stream or otherwise provide to someone viewing or listening to online content to optimize the likelihood of that person reacting in a desired way to that content.

optimizing the likelihood of that person reacting in a desired way to that content includes reading or viewing or listening to that content, or purchasing goods or services advertised or promoted by that content.

the base feature parameters are derived from a neurophysiological model of the functioning and response of one or more of the human lower cortical, limbic and subcortical regions in the brain to sounds.

the method is implemented by a system including a processor programmed for automatically analysing sounds according to musical parameters derived from or associated with a predictive model of the neurophysiological functioning and response to sounds by one or more of the human lower cortical, limbic and subcortical regions in the brain; and in which the system analyses sounds so that appropriate sounds can be selected and played to a listener in order to stimulate and/or manipulate neuro-physiological arousal and valence in that listener.

the system predictively models primitive spinal pathways and the pre-motor loop (such as the basal ganglia, vestibular system, cerebellum), all concerned with primal responses to rhythmic impulses, by analysing beat induction, using a specifically calibrated onset window.

the system predictively models rhythmic pattern recognition and retention regions (such as the secondary auditory cortex of the temporal lobes) by using self-similarity/auto-correlation algorithms.

the system predictively models the activation of mirror neuron systems, which detect power, trajectory and intentionality of rhythmic activity, through one or more of: indices of rhythmic power, including computation of volume levels, volume peak density, "troughs", or the absence of energy and, dynamic profiles of performance energy.

the system predictively models activation of mirror neuron systems by analysing a profile of expenditure of energy (precipitous for high arousal, smooth for low) before and in between onsets, important mirror neuron information, by a computation of profiles of energy flow leading to significant articulations.

the system predictively models the functioning and response of Heschl's Gyms to sound by determining levels of harmonicity and inharmonicity.

the system detects a principal fundamental through calculation of the harmonic product spectrum, then establishes degrees of harmonicity both within and among spectra of different fundamentals.

detection of a principal fundamental and the establishment of degrees of harmonicity is applied both to instantaneous moments, and to progressions of pitches and spectra in time (related to the tonotopic mapping of the area around Heschl's Gyms) and is expressed in terms of linear harmonic cost, which represents both the rate at which the fundamental is changing, and the harmonic distance of the changes.

the system predictively models the neurophysiological sensing of simple timbre by Heschl's gyrus, superior temporal sulcus, circular insular sulcus by analysing windows of harmonicity at instantaneous moments.

the system predictively models melodic and harmonic progressions in terms of how far each STFT time slices deviates from the simple ratios of the harmonic series: Linear harmonic cost arises from STFT time slices whose fundamental frequency differs from that of the previous slice; Time slices with no change in fundamental have a cost of zero.

the system combines indices of change in rhythmicity and harmonicity, with auditory brainstem and cortical activity innervating the amygdala, hippocampus and core emotional regions affecting neurotransmission and endocrine systems, including the HPA axis, dopamine circuits and levels of, for example, norepinephrine, melatonin and oxytocin.

the system determines rhythmicity using an equation that relates R to B and S, such as the equation $R=\sqrt{B}*S^2$, and where R is rhythmicity, B is beats per minute, and S is the mean of the beat strength.

the system determines rhythmicity using an equation that relates I to C and H such as the equation $I=C/10-H$, where I is inharmonicity, C is linear harmonic cost and H is instantaneous harmonicity.

the system determines turbulence using an equation that links T to H and P, such as $T=dH/dt*P$, where T is turbulence, H is harmonicity and P is energy during peak volume.

the system determines rhythmicity using an equation that relates R to B and S, and where R is rhythmicity, B is beats per minute, and S is the mean of the beat strength.

the system determines rhythmicity using an equation that relates I to C and H, where I is inharmonicity, C is linear harmonic cost and H is instantaneous harmonicity.

the system determines turbulence using an equation that links T to H and P, where T is turbulence, H is harmonicity and P is energy during peak volume.

the method is not genre sensitive.

Another aspect of the invention is a computer implemented system configured to implement the above methods. The analysis of sounds may operate in real-time on locally stored music data and the system includes software embodied on a non-transitory storage medium, firmware embodied on a non-transitory storage medium and/or hardware running on a personal computing device.

We can define multiple use cases for the above method. Specifically:

A. A computer implemented method of automatically classifying music in terms of arousal and valence (mood/emotion).

B. A computer implemented method of automatically classifying music in terms of physical activities.

C. Computer implemented method of automatically constructing a playlist in terms of preselected desired mood or emotion to be experienced by a listener.

D. Computer implemented method of automatically constructing a playlist in terms of a preselected sequence of mood and emotion to be experienced by a listener E. Computer implemented method of automatically constructing a playlist in terms of preselected physical activity.

F. Computer implemented system of automatically streaming music depending on the listener's activity, such as working, exercising, driving, seeking pain relief, seeking relaxation, seeking mood enhancement.

G. Computer implemented method of selecting sound or music to stream or otherwise provide to someone viewing online content.

H. Computer implemented method of selecting sound or music to stream or otherwise provide to someone viewing or listening to online content to optimize the likelihood of that person reacting in a desired way to that content, such as reading or viewing or listening to that content, or purchasing goods or services advertised or promoted by that content.

BRIEF DESCRIPTION OF THE FIGURES

Aspects of the invention will now be described, by way of example(s), with reference to the following Figures, which each show features of the invention:

FIG. 13 shows a look-up table used to calculate the Parameter Valence Hypothesis.

FIG. 32 shows sample categorisation from the Miles Davis repertoire.

FIG. 33 shows an example of other manual categorisations, in which tracks are further sorted into stable, rising and falling vectors.

FIG. 34 shows an example in which movements from Beethoven symphonies have been categorized according to the vectors.

DETAILED DESCRIPTION

This Detailed Description section describes one implementation of the invention, called X-System. A full description of a version of X-System is in PCT/GB2012/051314, the contents of which are incorporated by reference in Appendix A.

X-System is a system for automatically analysing music of all genres to predict its effect on the human mind and body, such as the autonomic nervous system. The system automatically categorises music in terms of moods and/or emotions and is able to select and play music according to specific mood and/or emotions. Moods and/or emotions are located in a space defined by valence on one axis and arousal on another axis.

More generally, X-system is based on models of the musical brain, in turn derived from IMRM—the Innate Neurological Response to music, which allows the system to predict universal musical responses (i.e music from any culture). The system is based on analyses derived from and verified by substantial neurophysiological data as well as large number of subjective data. The neurophysiological data includes Heart Rate, Heart Rate Variability (with approximately 1000 people over 4 million tracks) and Galvanic Skin Conductance (with approximately 500 subjects and 300 tracks).

The system's parameters are based on INRM and are used to model organs and functions of the human musical brain as opposed to only using signal processing. Hence, arousal and valence can be predicted in all cultures and are not genre sensitive.

Because of its basis in brain modeling and neurophysiological data, the system achieves higher accuracy compared to other techniques. Arousal predictions have been produced with about 99-100% A accuracy, and valence predictions have been produced with about 75% accuracy.

One of the key aspect of the system, is performing physiological verification using Heart Rate Variability (HRV) as an indication of vagal power, where positive valence corresponds to high vagal power (as indicated by high HRV), and negative valence corresponds to low vagal power. The hypothesis valence algorithm is described in details below.

Figure 1:
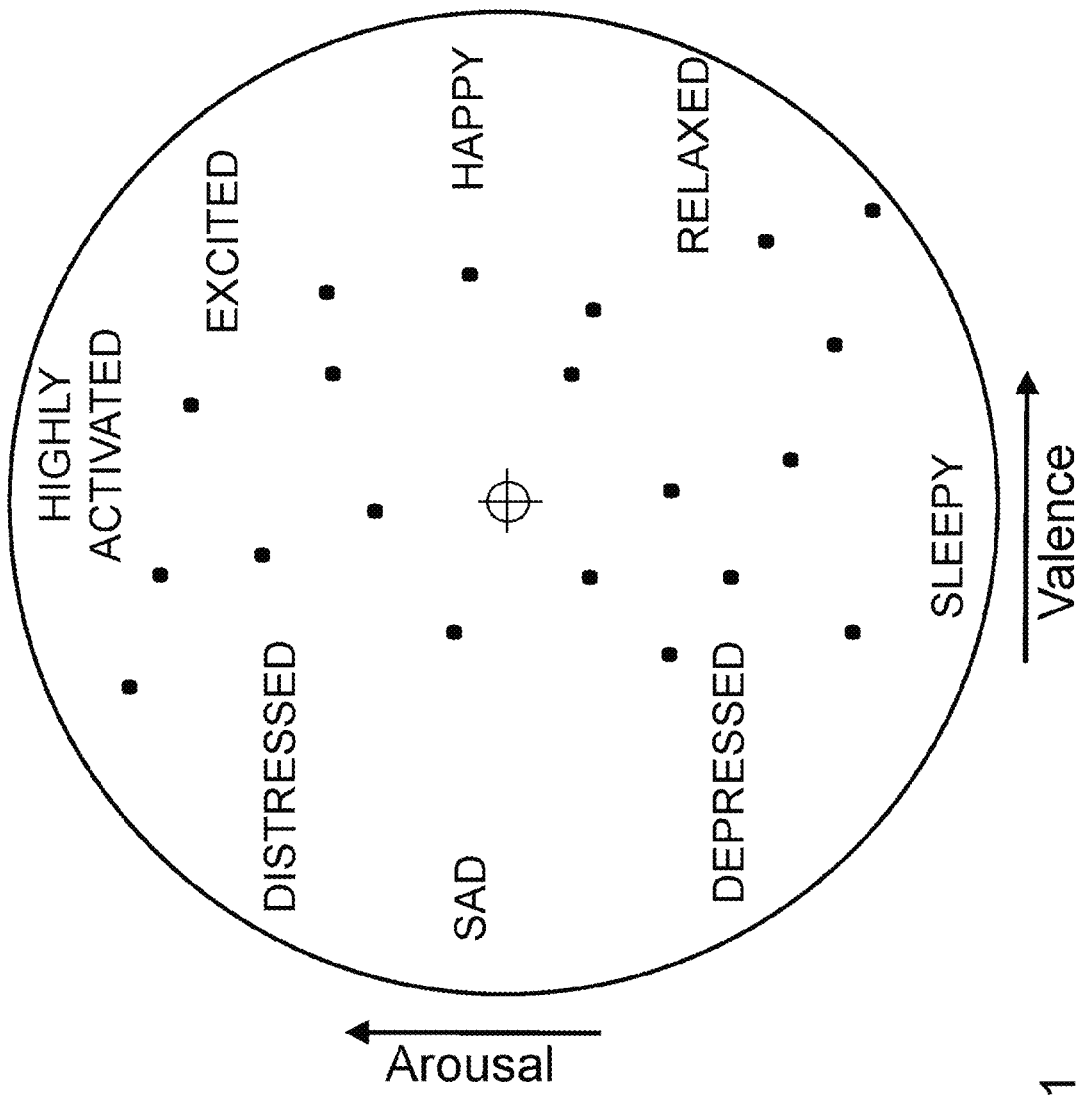
FIG. 1 shows a two-dimensional emotion-mood space used to plot predicted moods and emotions.

FIG. 1 shows a two-dimensional valence-arousal space used to plot predicted moods and/or emotions to be experienced by a listener. Parameters, such as arousal and valence, are combined to predict positive and negative moods and emotions. The dots show examples of predictions of audio tracks and their locations in the emotion-mood or valence-arousal space. Audio tracks are categorized by the X-System in terms of moods and emotions, such as "distressed", "sad", "depressed", "sleepy", "highly activated", "excited", "happy" or "relaxed". A specific mood, such as 'sad' is thought of as being located at a specific region in the valence-arousal space. The mood 'happy' is thought of as being located at a different specific region in the valence-arousal space—at the same level of arousal as the 'sad' emotion, but at the opposite end of the valence axis.

The two-dimensional emotion-mood space shown in FIG. 1 is an adaptation of the Geneva Emotion Wheel (Scherer 2005), where moods and emotions are manually arranged in a circular fashion by subjects manually assigning a location of their mood in the circular space. Low sympathetic autonomic arousal is located at the bottom of the wheel, while high sympathetic autonomic arousal is located at the top of the wheel. Low valence is valence located at the left and high valence is located at the right of the wheel.

Although a two-dimensional model based approach is used as an example in this document, the techniques and algorithms describe may be extended to a three-dimensional model based approach, in order to accommodate further distinctions, such as distinctions between tone and power on the human mind and body, such as in the Parasympathetic Nervous System.

The technology discussed here has a wide range of applications. Key applications of the system are, but not limited to, the following:

The system can automatically select and play music in order to stimulate and/or manipulate a mood and/or an emotion to be experienced by a listener.

The system can automatically help people, through music, navigate, change, or support a specific mood or emotion. As an example, the system can automatically help a listener relax, concentrate, or fall asleep. The system can also automatically help the listener prepare for, or support any activities such as working or exercising.

The system can automatically support medical interventions and procedures through relaxation, calming effects, environment, stimulation of movement, and potentially reduction of pain.

The system can automatically offer musical-emotional navigation, automation and enhancement of playlists in all musical cultures and genres and support for streaming services.

The system can automatically construct playlists according to any X-System parameters, such as arousal, valence, rhythmicity, harmonicity, turbulence, sharpness, volume, etc.

The system can automatically tailor playlists for any needs; such as for example increase or decrease autonomic arousal.

The system can automatically select and stream music depending on the listener's activity, such as working, exercising, driving.

The system can automatically construct playlists to sequence journeys for the listener in mood or emotions, such as from relaxed to excited, or from sad to happy, or any other combination of moods and emotions.

Through the modelling of the musical brain, the system offers an important entry point to music-medicine and to a whole raft of innovation in human and social development.

Figure 2:
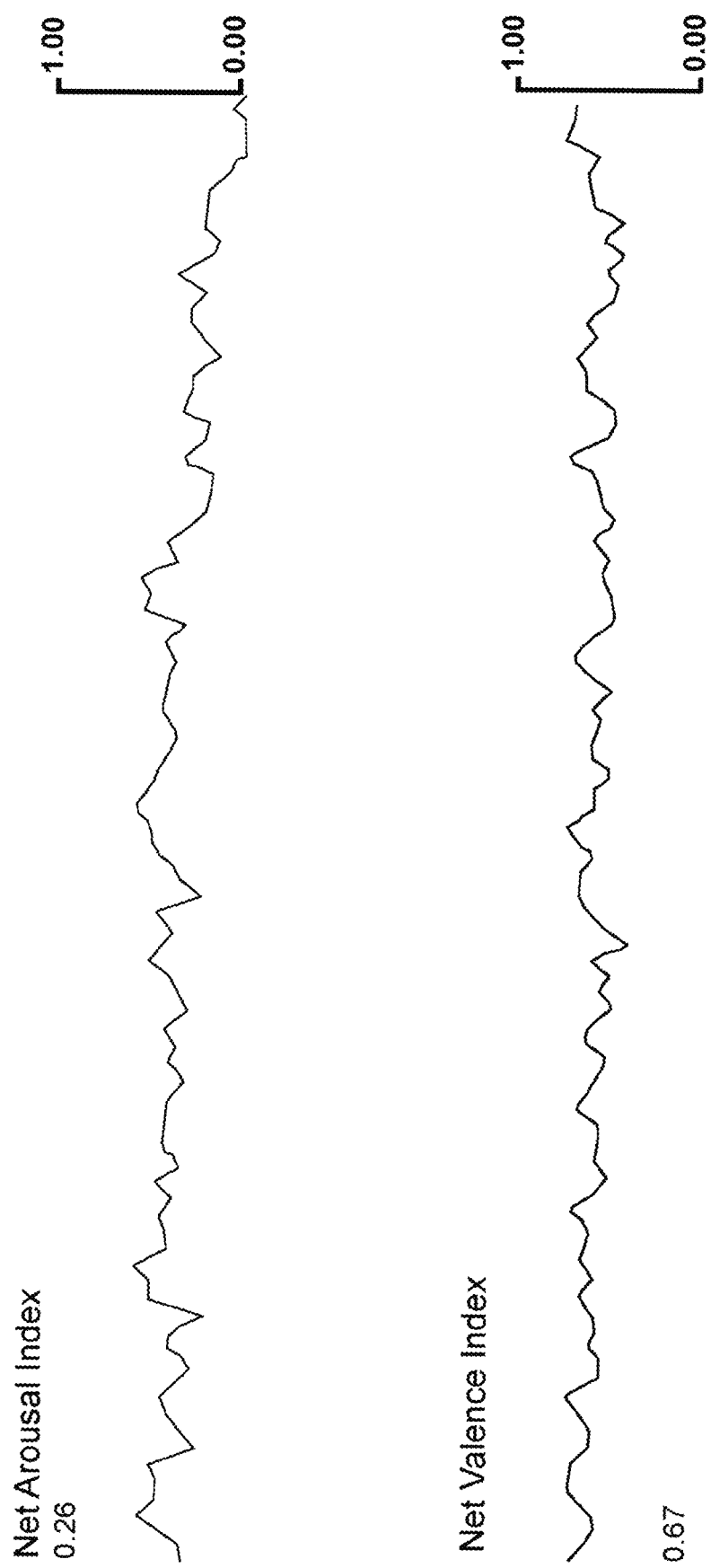
FIG. 2 shows plots of arousal index and valance index of an audio track as a function of time.

FIG. 2 shows plots of arousal index and valance index of an audio track as a function of time. Audio tracks are analysed second by second and consequently moods and emotions can also be predicted second by second. Other parameters analysed as a function of time include: fundamental, harmonicity, Linear Harmonic Cost (LHC)/sec, neural net arousal index, sharpness, turbulence at both 1 Hz and 50 Hz, volume.

Figure 3A:
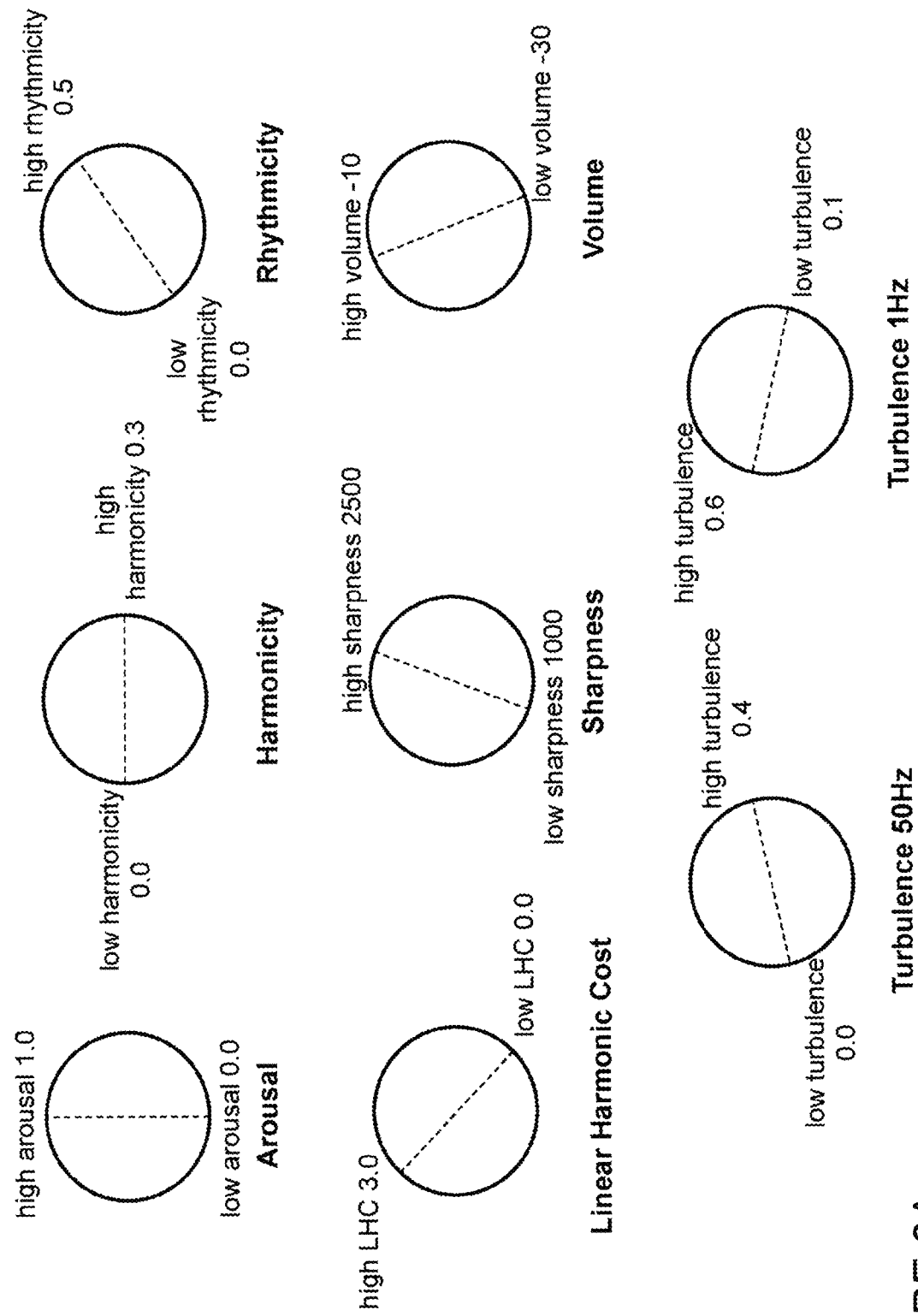
FIG. 3A shows two-dimensional emotion-mood spaces associated with parameters analysed by X-System.
Figure 3B:
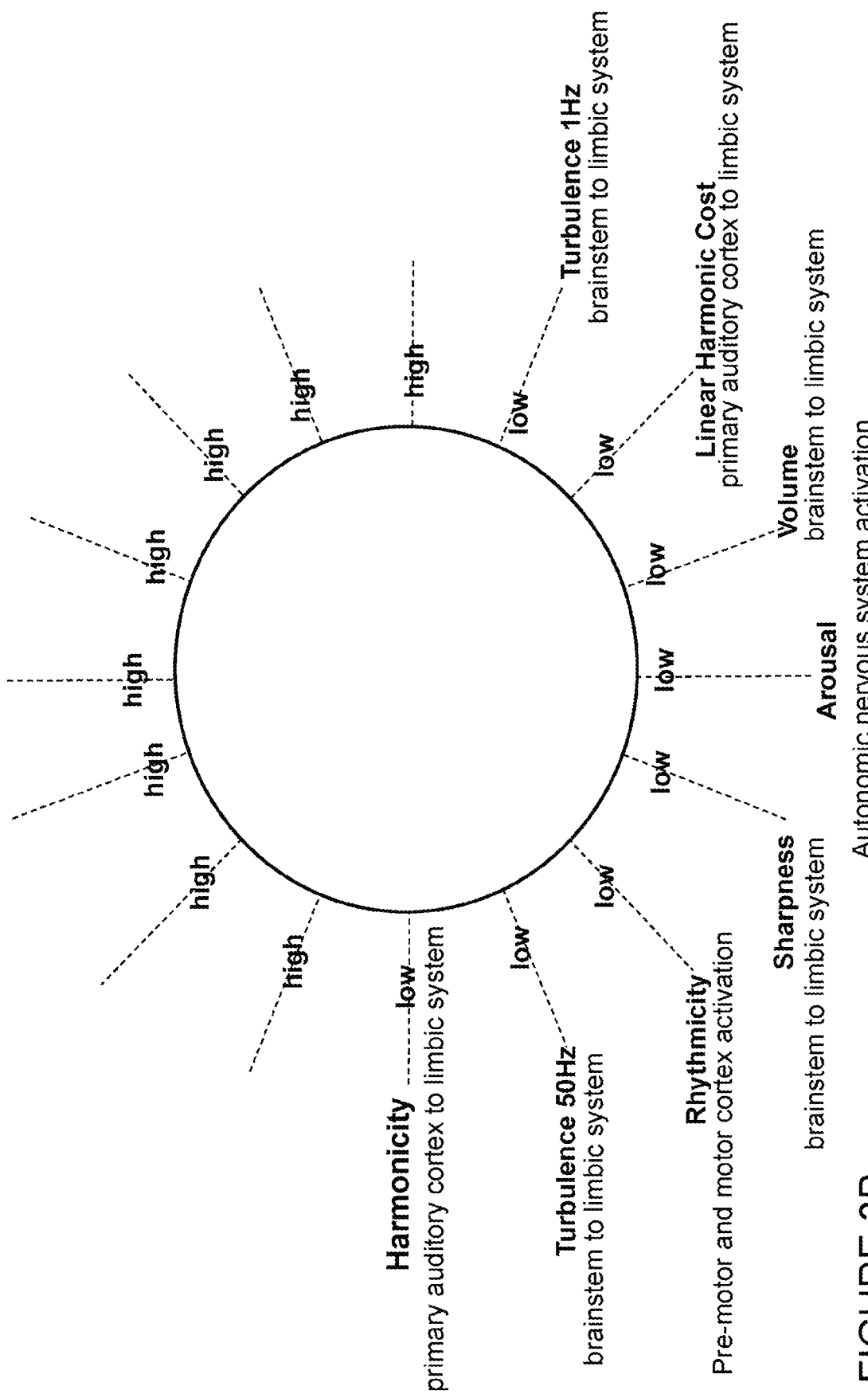
FIG. 3B shows a two-dimensional emotion-mood space with examples of parameters analysed by X-System.

FIGS. 3A and B illustrates how X-system combines brain-based parameters into a single model where emotions and moods are ascribed to areas of the emotion-mood space. X-System analyses a number of parameters (for example arousal, harmonicity, turbulence, rhythmicity, sharpness, volume, Linear Harmonic Cost (LHC)) in order to model the musical brain and predict how its organs and pathways respond to different kinds of music.

The X-System parameter values for a track, for example, with high arousal, high harmonicity, high rhythmicity, low-to-medium harmonic cost, medium-to high sharpness, medium-to-high volume, high 50 Hz turbulence and low 1 Hz turbulence intersect in the happy-excited area of the emotion-mood space.

Similarly X-System may search for given emotional qualities in music by the ranges of values that intersect in the given area of the space. For example a search for "sad" music would search for tracks with low arousal, medium-to-low harmonicity, low rhythmicity, medium harmonic cost, low sharpness, low volume, low 50 Hz turbulence and medium-to high 1 Hz turbulence.

The different parameters are now described in detail. Reference may also be made to Appendix A.

X-System models the most ancient and primitive reactions to sound and to music in parts of the brain, such as the brainstem and amygdala. These reactions include:

Turbulence where surges and turbulences in sound are detected by the brainstem and communicated as emotional information by way of the inferior colliculus to the amygdala;

Sharpness where primitive responses to high sounds, like the hissing of snakes, are communicated to emotional centres of the brain;

and volume where loudness and changes in loudness are detected by the brainstem and transmitted as emotional information We combine existing algorithms to model the brainstem, motor cortex and Heschl's Gyms respectively, but these are not separate algorithms.

The following algorithm cluster incorporates turbulence, sharpness and volume in a model of brainstem response.

Figure 4:
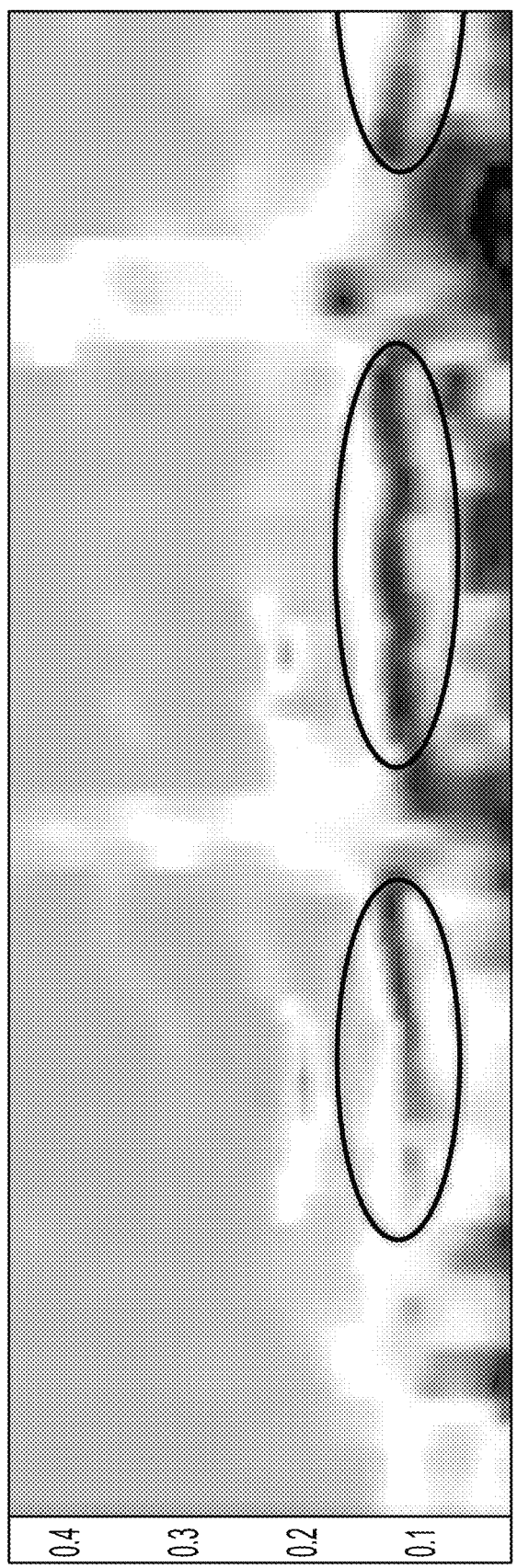
FIG. 4 shows an example of a plot of an audio track for determining rhythmicity.

X-System also models the pre-motor and motor cortex. This includes modelling of responses to:

Pulse where systems of the brain concerned with movement and preparing for movement are activated by the speed of beats per minute;

and rhythmicity where the power, density and salience of rhythm not only activates movement but also stimulates arousal and emotional change. As an example, FIG. 4 shows an example of a plot of an audio track for determining the rhythmicity.

The following algorithm cluster incorporates pulse and rhythmicity in a model of the motor cortex.

Figure 5:
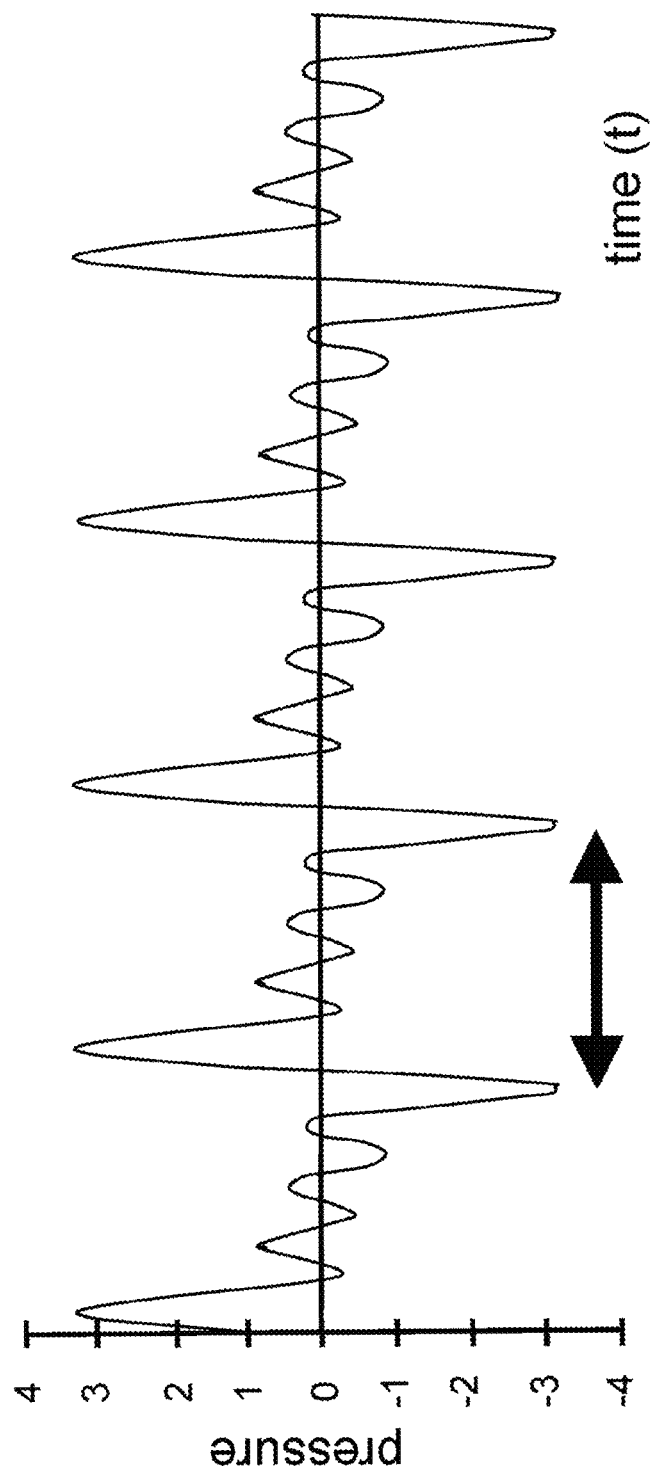
FIG. 5 shows an example of a plot of an audio track for determining the fundamental detection.

X-system also models the primary auditory cortex (Heschl's Gyms) and pathways to the limbic system (amygdala etc) including:

fundamental detection where it models Heschl's Gyms to establish which is the most important frequency in a single sound, note or chord. FIG. 5 shows an example of a plot of an audio track for determining the fundamental detection.

harmonicity, where it further models Heschl's Gyms to establish the vertical "harmonicity" of the spectrum of sound at any given moment.

The following algorithm cluster incorporates fundamental detection and harmonicity: in a model of Heschl's Gyms.

Figure 6:
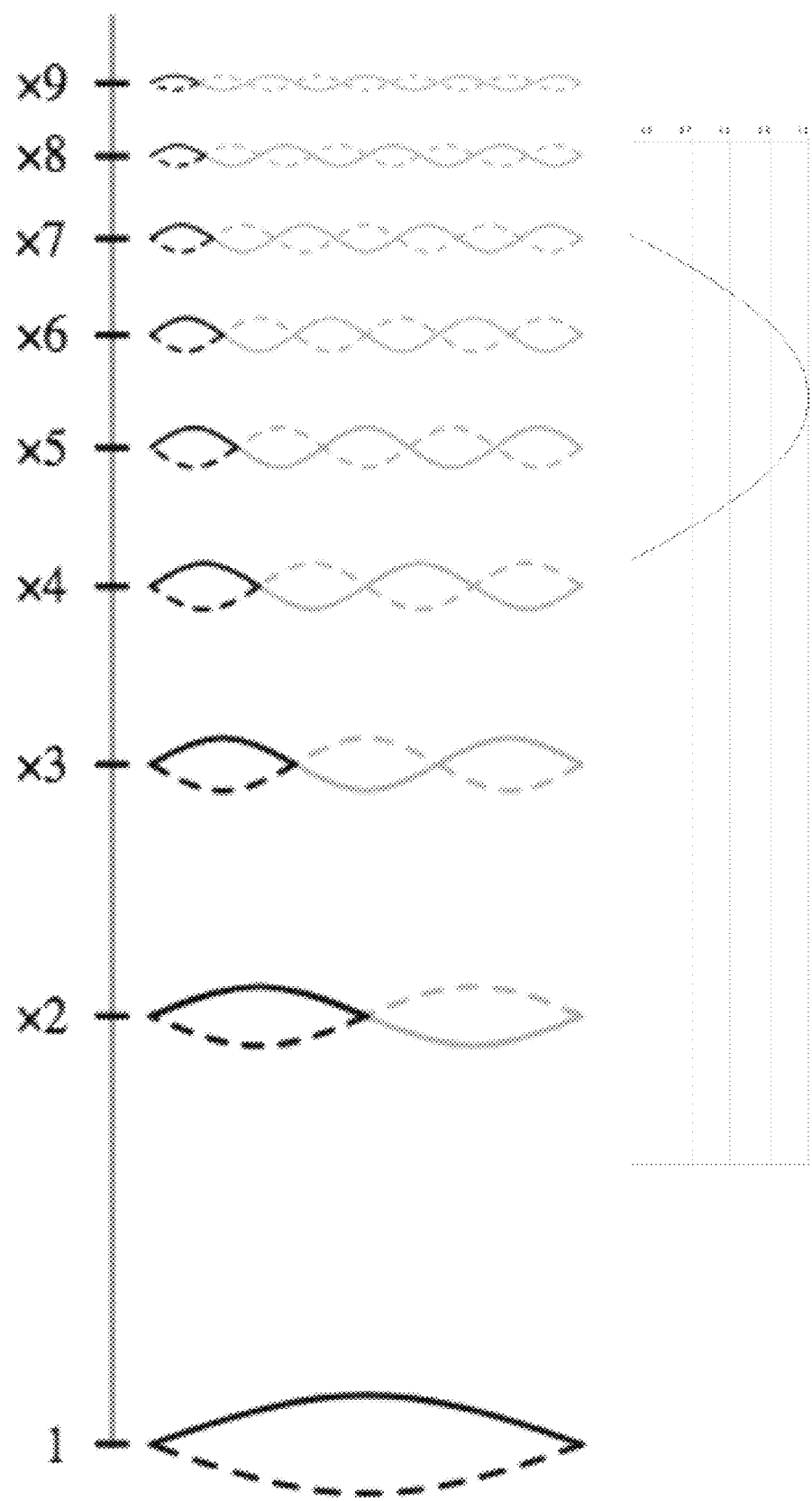
FIG. 6 shows an illustration of the vertical "harmonicity" of the spectrum of sound.

Levels of "harmonicity" are determined by how close the pattern of the spectrum of sound is to the harmonic series, as illustrated in FIG. 6—the simplest pattern of sound in nature. The higher the harmonicity of a sound, i.e. the closer to the pattern of the harmonic series, the more relaxing and soothing the effect on the limbic system and emotional centres of the brain; the lower the harmonicity, the more arousing the effect. The pattern of the first six partials of the harmonic series, starting on the note C, is G C G C C E.

and linear harmonic cost, where the system models the way that movement from one note or sound to another affects emotional centres of the brain. The more "harmonic" the step, the lower the harmonic cost and the greater the calming effect. The less "harmonic" the step, the greater the harmonic cost and the higher the arousal.

Figure 7:
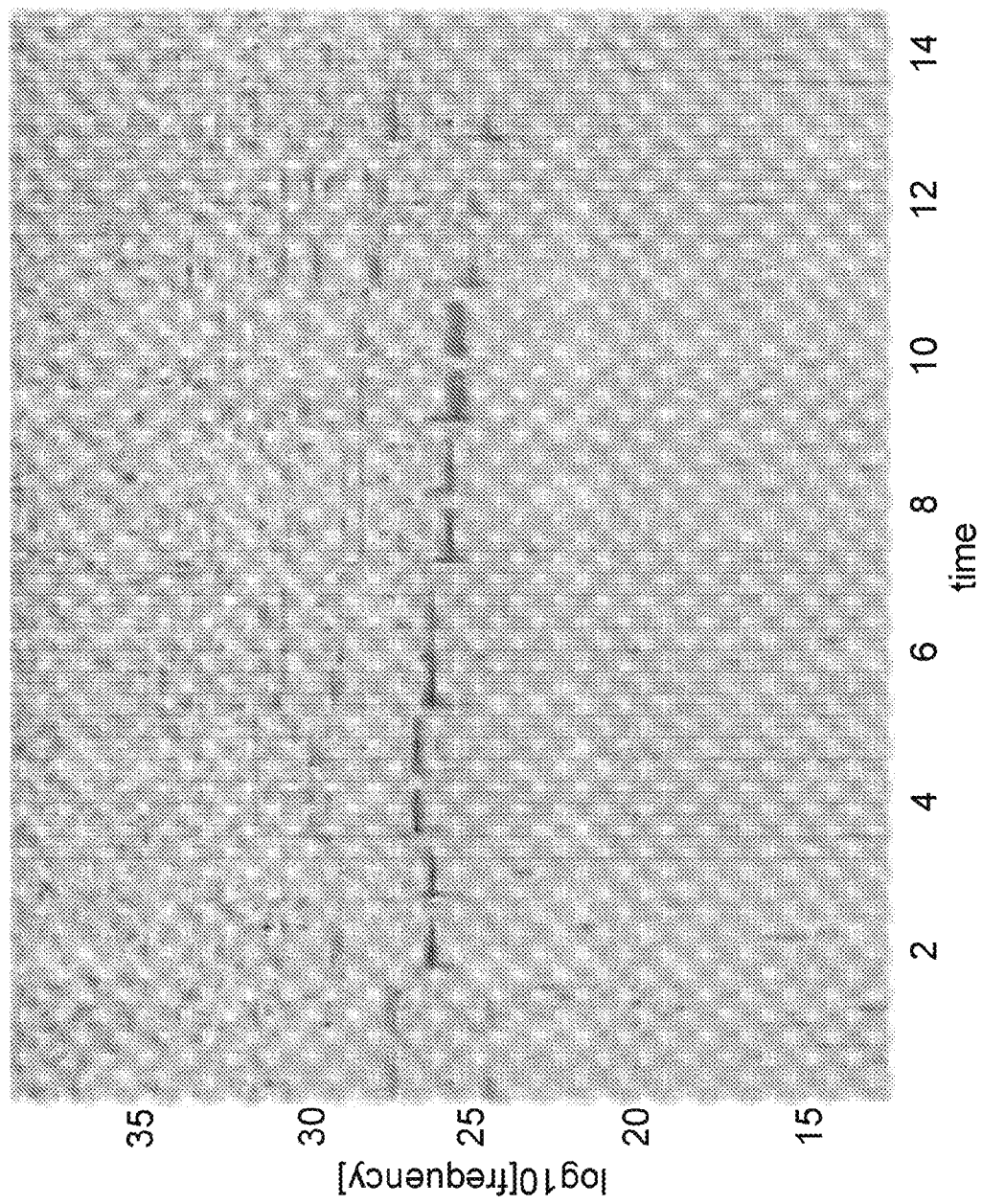
FIG. 7 shows an example a spectrogram of the first phrase of Twinkle Twinkle Little Star.

FIG. 7 shows an example a spectrogram of the first phrase of Twinkle Twinkle Little Star. The first four notes of the melody—CCGG (Twinkle, twin-kle) are very "harmonic", i.e. they fit perfectly into the pattern of the first four partials of the harmonic series—see above. The next notes—AA (lit-tle) do not appear until much further up the harmonic series and are therefore less "harmonic" and a little more "arousing". It is noticeable that the melody returns to the very harmonic G (star) after the disruptiveness of the two A's.

Prediction of Emotion and Mood

X-System defines emotion and mood in the following ways:

Emotion is an altered or heightened state of mind or body that may precede or follow a real or imagined action. For example: "I say goodbye to a friend, I am sad"; or "I am about to run a marathon, I am excited"; or "I made a mistake, I am ashamed".

Mood is a sustained state of mind and body, which may be related to an action, or may be spontaneous. For example: "Your letter arrived in the post today, and I have been happy all morning"; or "For some reason I have been 'down' all day".

Feelings are our reflections on or intimations of emotions and moods. For example: "First I was ashamed, now I just feel bad about making that mistake"; "Please don't hurt my feelings, I already feel bad about it all"; or "I have a really good feeling about all of this".

X-System is a computer implementation that is based on the theory that the emotional/mood qualities music may communicate are limited to basic states of mind and body; they are propensities and potentials for more cognitively/strategically filtered emotional expression. For example music may communicate a state of mind and body close to "joy"; it may also embody "sadness", even a sense of "loss", but it cannot embody "guilt". Music may induce something close to the general states of mind and body within which more cognitively driven emotions like "guilt" may take place.

X-System is also a computer implementation that is based on the theory that emotions and moods as described by language are like islands in a fluid ocean of musical emotion. Music does not land on the island of "joy" or "guilt"; it floats around in the sea of neural substrates that surround the island.

X-System does not engage with valence directly, but is a computer implementation that is based on the theory that some emotions—like "joy"—may be described as positive—and others—like "sadness" as negative. It predicts emotion and mood by combining arousal and valence.

How does X-System Predict Arousal?

X-System combines values provided by its modelling of the musical brain to predict levels of autonomic arousal for individual tracks.

Figure 8:
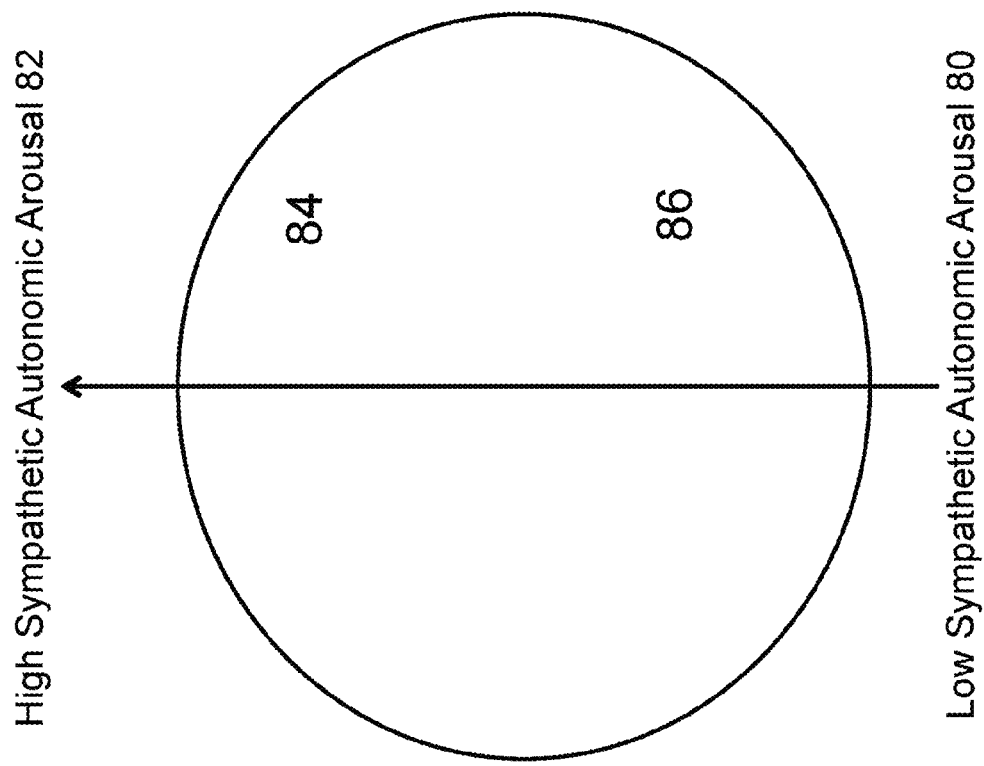
FIG. 8 shows a plot of a two-dimensional emotional-mood space.

FIG. 8 is a plot of a two-dimensional emotional-mood space, and where predictions of emotions to be experienced by a listener, are automatically calculated and plotted. The predictions of emotions are arranged in a circular fashion with low sympathetic autonomic arousal 80 located at the bottom and high sympathetic autonomic arousal 82 located at the top of the wheel. As an example, Kool and the Gangs Hollywood Swingin is automatically plotted on the wheel 84 and is predicted to stimulate high autonomic arousal and high motor activation. The Adagio from Rachmaninov s Piano Concerto no 2 in C minor is automatically plotted on the wheel 86 and is predicted to be of low arousal and generally calming.

X-System verifies these results by both subjective categorisation and physiological measurements.

Figure 9:
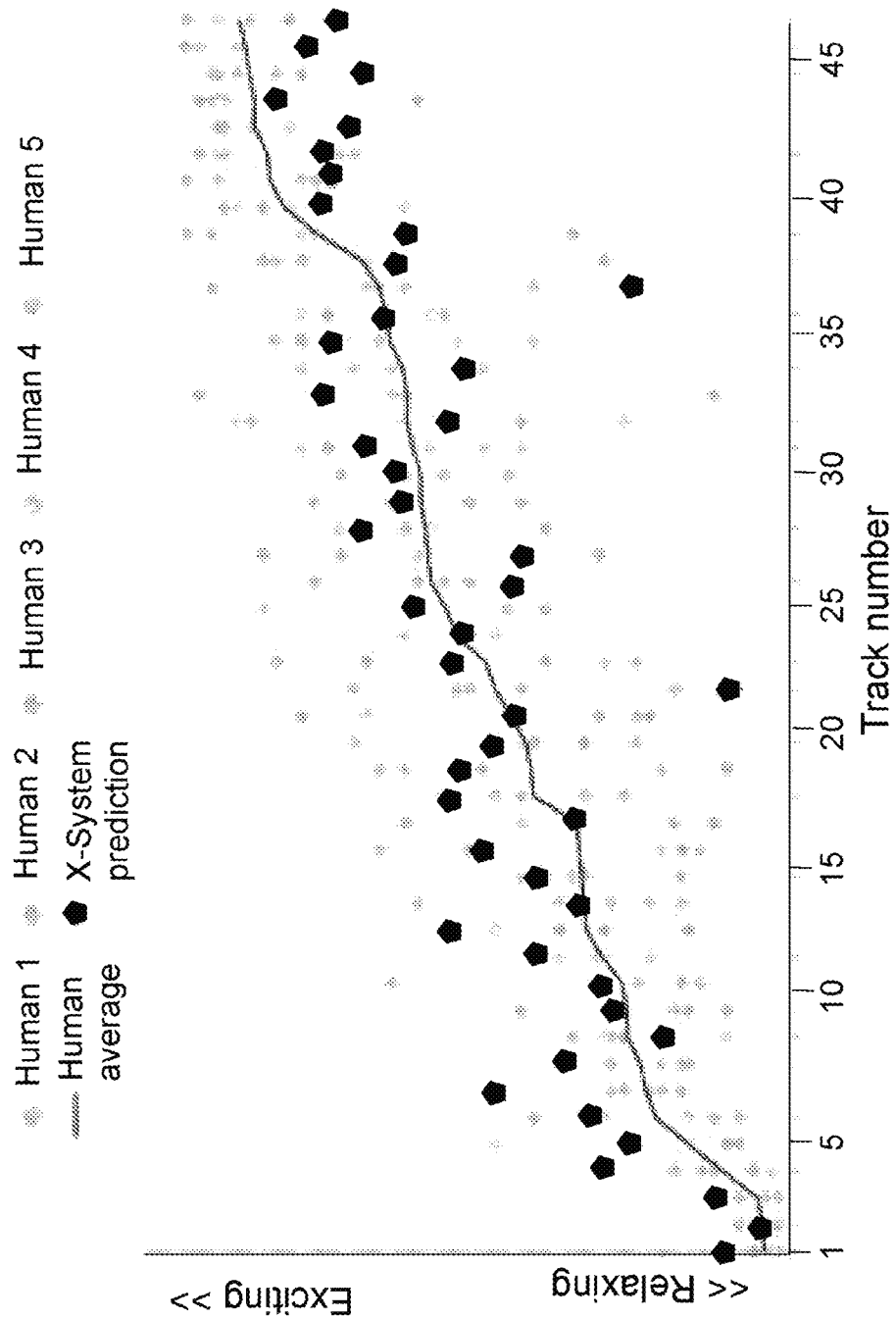
FIG. 9 shows X-System predictions of levels of arousal as a function of 47 music tracks compared to the predictions of 5 different experts musicologists.

FIG. 9 shows X-System predictions of levels of arousal as a function of 47 music tracks compared to the predictions of 5 experts musicologists. The 47 tracks are played to a listener in ascending order of arousal. The predictions are then compared to the average heart rate (BPM) of the listener, which is known to give a good indication of arousal or counter-arousal in the autonomic nervous system. The results show that X-System is capable of outperforming expert musicologists in predicting levels of arousal over a broad music repertoire.

In a clinical psychology experiment, subjects were stressed by a track of music identified by X-System as being highly arousing, and de-stressed by two tracks identified as relaxing.

The protocol of the experiment is the following:
Connect to X-System;
Habituation period;
Baseline (B);
"Anxious" track (A1);
Quiet rest (QR1);
"Relaxing" track 2 (R2/1);
"Relaxing" track 1 (R1/2).

Figure 10A:
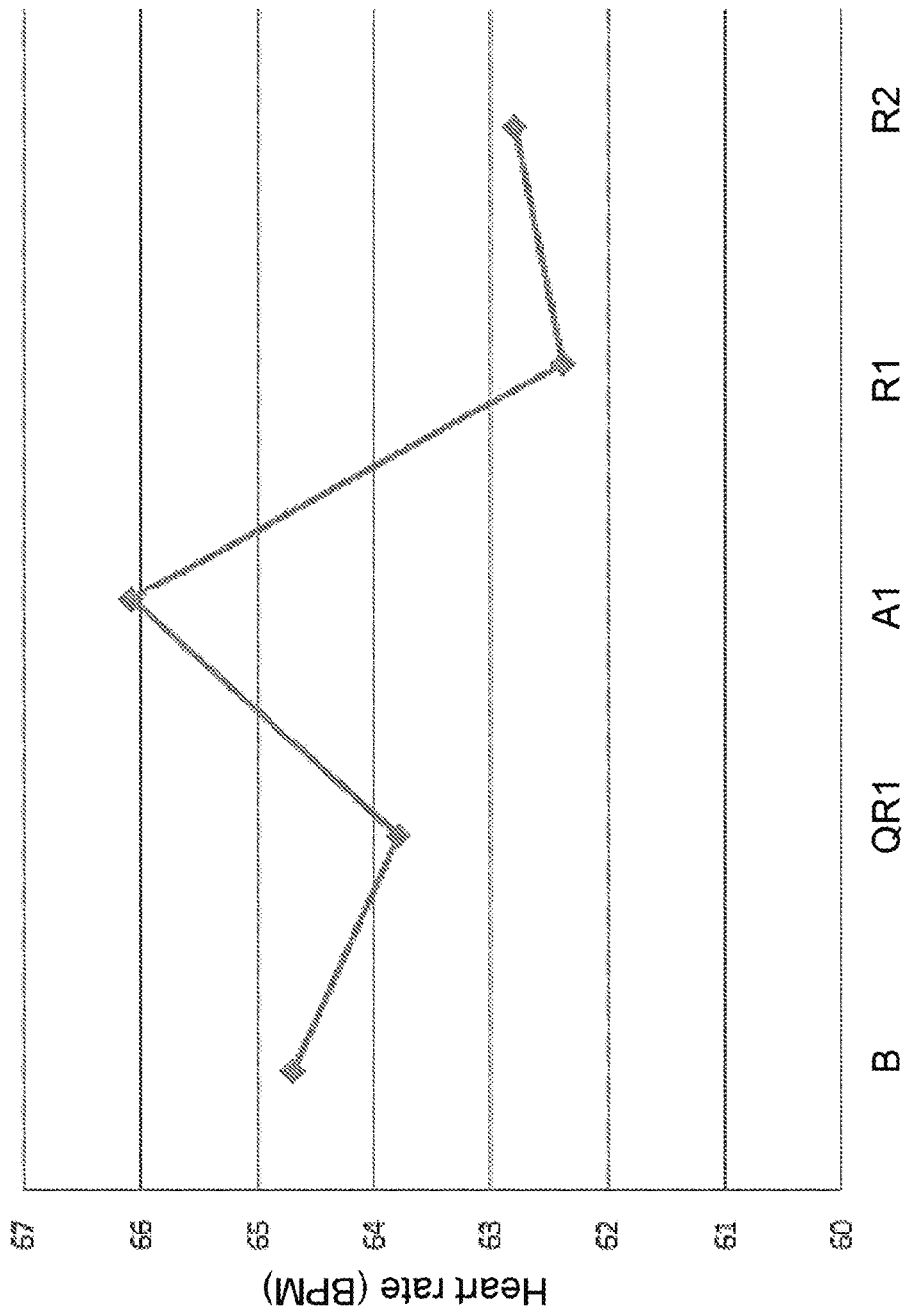
FIG. 10A shows results of the physiological measurement with a plot of average heart rate of a first subject to a specific playlist.
Figure 10B:
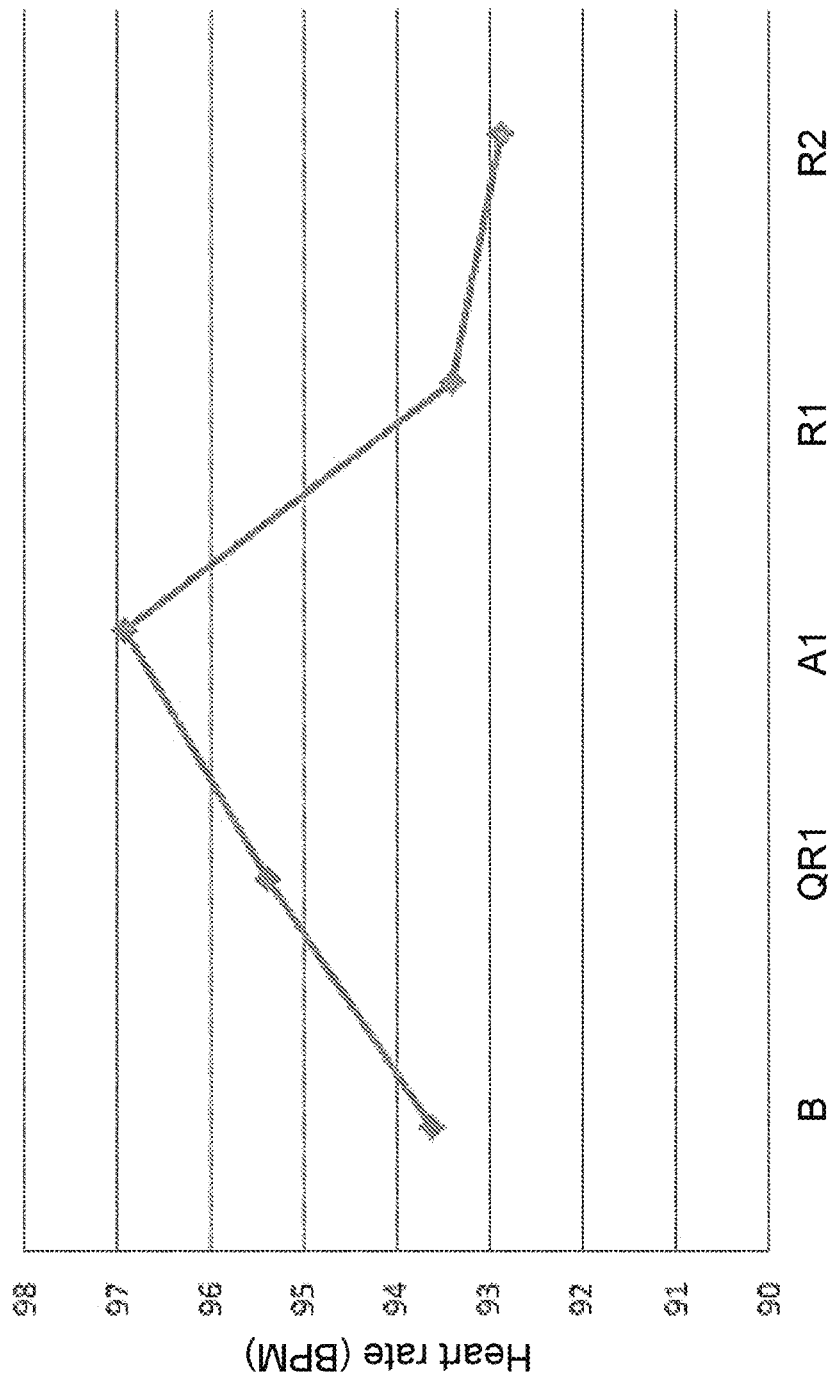
FIG. 10B shows results of the physiological measurement with a plot of average heart rate of a second subject to a specific playlist.

FIGS. 10A and 10B show results of the physiological measurement with a plot of average heart rate of two different listeners as a function of a playlist including a baseline track (B) and a quiet rest (QR1), followed by an arousing track or anxious track (A1) and two relaxing tracks (R1 and R2). The track with the higher arousal index as automatically predicted by the X-system results in higher heart rates, whereas the track with the lower arousal index results in lower heart rates for both listeners.

Prediction of Valence, Emotion and Mood

X-System combines its parameters to automatically predict positive and negative moods and emotions. These predictions are plotted in a two-dimensional emotional-mood space.

Figure 11:
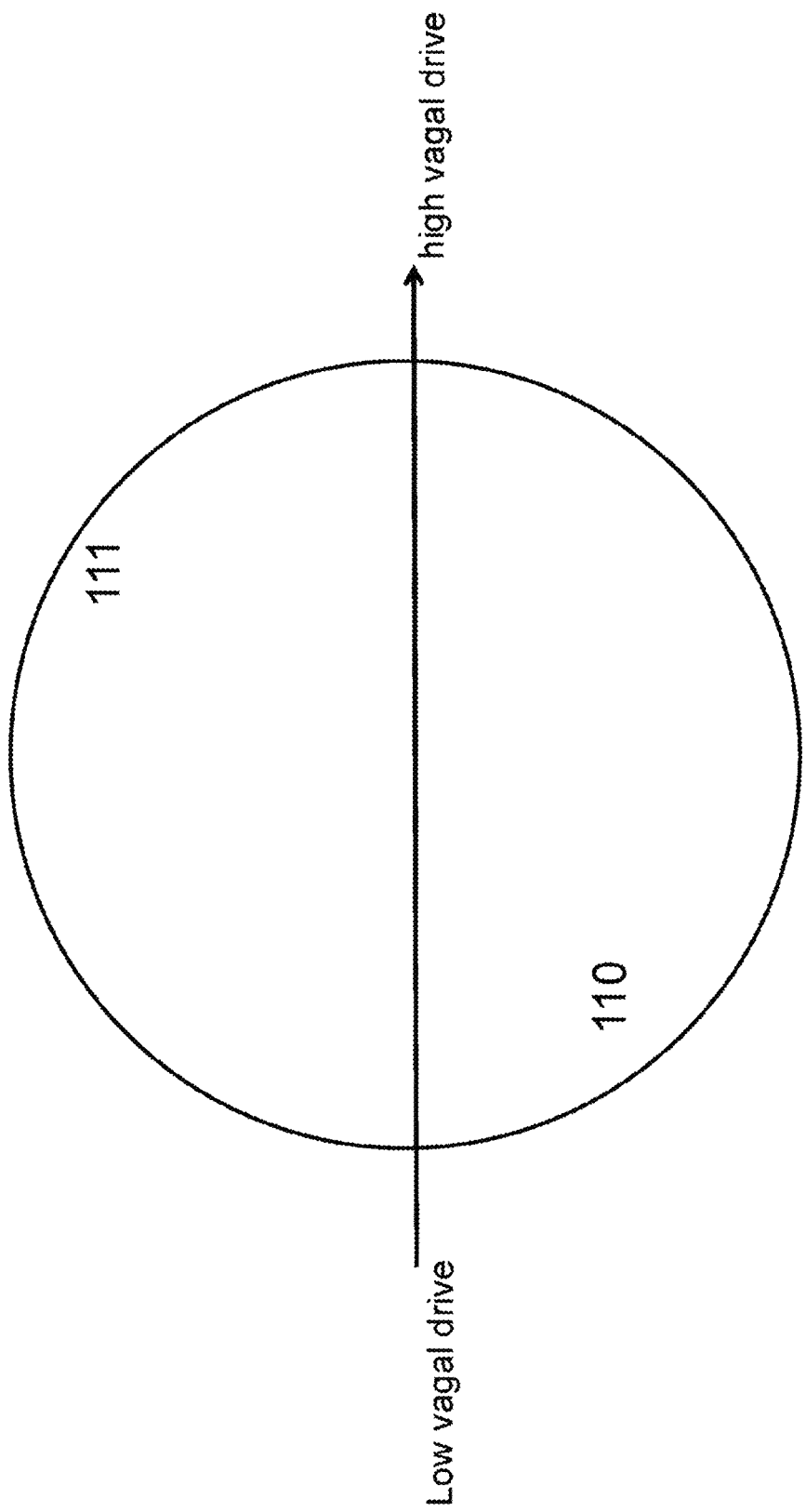
FIG. 11 shows plots of predictions of audio tracks and their locations in the emotional-mood space.

FIG. 11 shows plots of automatic predictions of audio tracks and their locations in the emotional-mood space of the following tracks. Clannad's Theme from Harry's Game 110 is predicted as "sad", and Katrina and the Waves' Walking on Sunshine 111 as "happy".

X-System Verifies these Results by Subjective Categorisation and by Employing Neural Networks and Linear Regressions Whereas linear regression models can be restricted by their nature, i.e only producing lines, neural network are able to continuously improve. However, each technique may provide better results for a specific type of music. By combining multiple machine learning approaches to estimate arousal and valence, the results provided are more accurate and less prone to overfitting.

The neural network, for example a standard feed-forward neural network, outputs both arousal and valence, as results have shown that by forcing the neural network to learn arousal at the same time as valence provided better results for valence predictions.

Physiological verification has been performed using Heart Rate Variability (HRV) as an indication of vagal power (directly related to positive and negative emotions). In a recent experiment involving physiological measure of HRV in the responses of 6 listeners, the total vagal power for Theme from Harry's Game was 904, and the total power for Walking on Sunshine was 1165; this data verifies X-System's prediction.

Linear Regressions, Neural Networks and a Linear Hypothesis

Figure 12:
FIG. 12 shows a diagram illustrating the key elements of the system.

A number of algorithms are used to predict valence and arousal, as shown in FIG. 12 with a diagram illustrating the inputs and outputs of the different algorithms.

The system comprises stacked layers of analysis: at the base we have hand engineered features—these are either musical features or more general signal processing features, such as linear harmonic cost, volume, sharpness, rhythmicity, 50 Hz turbulence, 1 Hz turbulence, harmonicity and fundamental From these features we calculate arousal and valence each in multiple ways which are then finally combined into a result, such as by a simple mean average.

For arousal we use two methods: a linear regression and a neural network, both of which take as inputs one or more of the base features: linear harmonic cost, volume, sharpness, rhythmicity, 50 Hz turbulence, 1 Hz turbulence, harmonicity and fundamental.

The linear regression for arousal is trained on a large dataset of audio tracks, such as a dataset of 100 songs, where each song was listened to by a group of human experts, each of whom gave an estimate of its arousal rating.

The neural net outputs a neural net arousal, which is then combined, with the output of the linear regression arousal to determine the combined arousal.

For valence the same neural network is used, and combined with a valence hypothesis algorithm written by a human expert. The valence hypothesis algorithm uses the base features as well as the output of the linear. The valence hypothesis algorithm, as described below, is based on subjective evidence as well as a large number of experiments, performed on a large number of listeners, in which physiological measurements, such as HRV measurements, were taken. Physiological measurements may also include respiratory sinus arrhythmia (RSA) measurements.

The neural net also outputs a neural net valence, which is then combined with the output of the valence hypothesis algorithm to determine the combined valence.

The neural network outputs for both valence and arousal are predicted together by a single network working from the base features. This network was trained on a dataset of some 60,000 or so songs with ground truth values for arousal and valence provided by human experts.

Finally to produce, the combined arousal and combined valence, our most accurate predictions of arousal and valence we take a mean average across the outputs for each feature. That is to say for arousal we return the midpoint between the linear regression and the neural network, and for valence we take the midpoint between the neural network and the parameter valence hypothesis.

The combined arousal and valence values are then plotted on the X and Y axes of an arousal-valence 2-D space.

Valance Hypothesis and the Averaging Process

A detailed description of the parameter valence hypothesis and the averaging process follows. The approach combines our current Neural Network Arousal Index (NNAI) and Neural Network Valence Index (NNVI) with our Net (Parameter) Arousal Index ((NAI) or (N(P)AI)) and a Parameter Valence Hypothesis. The Net (Parameter) Arousal Index corresponds to the output of the linear regression algorithm.

We shall work through examples of how this currently functions. At the moment it is an automated mixture of simple arithmetic and look-up tables.

Taking the example of Ain't No-body

| Harm | 1 HzT | LHC. | NNVI | Ryh. | Shrp | NAI | Vol. | NNAI | Fund | 50 HzT |
|---|---|---|---|---|---|---|---|---|---|---|
| 0.11 | 0.46 | 3.12 | 0.60 | 0.25 | 2400 | 0.69 | −17 | 0.74 | 593 | 0.33 |

The above parameters represent the base features as well as the outputs of the X-System algorithms averaged over the whole track.

Step 1

Look up the NNAI

For this example, the index is 0.74

Multiple the index by 10 (i.e. move the decimal point back one place) to create a consistent scale of 10.

The NNAI is now 7.4 on a scale of 10

Step 2

Look up the NNVI

For this example, the index is 0.60

Look up the index in the following table:

| Value | 1 | 2 | 3 | 4 | 5 | 6 | 7 | 8 | 9 | 10 |
|---|---|---|---|---|---|---|---|---|---|---|
| Index | 0.52 | 0.53 | 0.54 | 0.55 | 0.56 | 0.57 | 0.58 | 0.59 | 0.30 | 0.61 |

In this case the higher the valence index, the higher the values generated by the look-up table on a scale of 1 to 10

Step 3

Look up the N(P)AI: for this example the index is 0.69.

Multiply the Index by 10 (i.e. move the decimal point back one place).

The N(P)AI is now 6.9 on a scale of 10.

In the case of classical music only add 0.6 to the value of the N(P)AI. The hypothesis algorithm includes an adjustment for Western classical music, but is otherwise not genre sensitive, and universal in its application.

Step 4

Look up the arousal level of the N(P)AI in the following table:

| Low | Medium | High |
|---|---|---|
| 0 to 4 | 4 to 6 | 6 to 8 |

The N(P)AI level is in this example high arousal.

This value is used to help calculate the Parameter Valence Hypothesis (PVH). Choose the appropriate look-up table, as shown in the Table in FIG. 13. X-System parameters predict valence in different ways, depending on the level of arousal and calculate the valence PVH index in the following way:

Look up the Harmonicity in the X-System analysis chart: in this case the value is 0.11.

Look up the equivalent value in the high arousal table: the Harmonicity now has a value of 6.5 on a scale of 10.

Look up 1 HzT: in this case it is 0.46.

Look up the equivalent in the high arousal table: the value is now 7.6 on a scale of 10.

Look up Rhythmicity: 0.25.

Look up the equivalent: the value is now 6.4 on a scale of 10 (NB reverse scale).

Average the 3 above values: the combined Parameter Valence Hypothesis index is now 6.8.

(Follow similar look-up procedures for medium and low arousal tracks. Values that exceed the range simply become the final value at the appropriate end of the scale)

Step 5

Average the two arousal indices (NNAI and N(P)AI): in this case, the resulting arousal value is 7.15.

Figure 14:
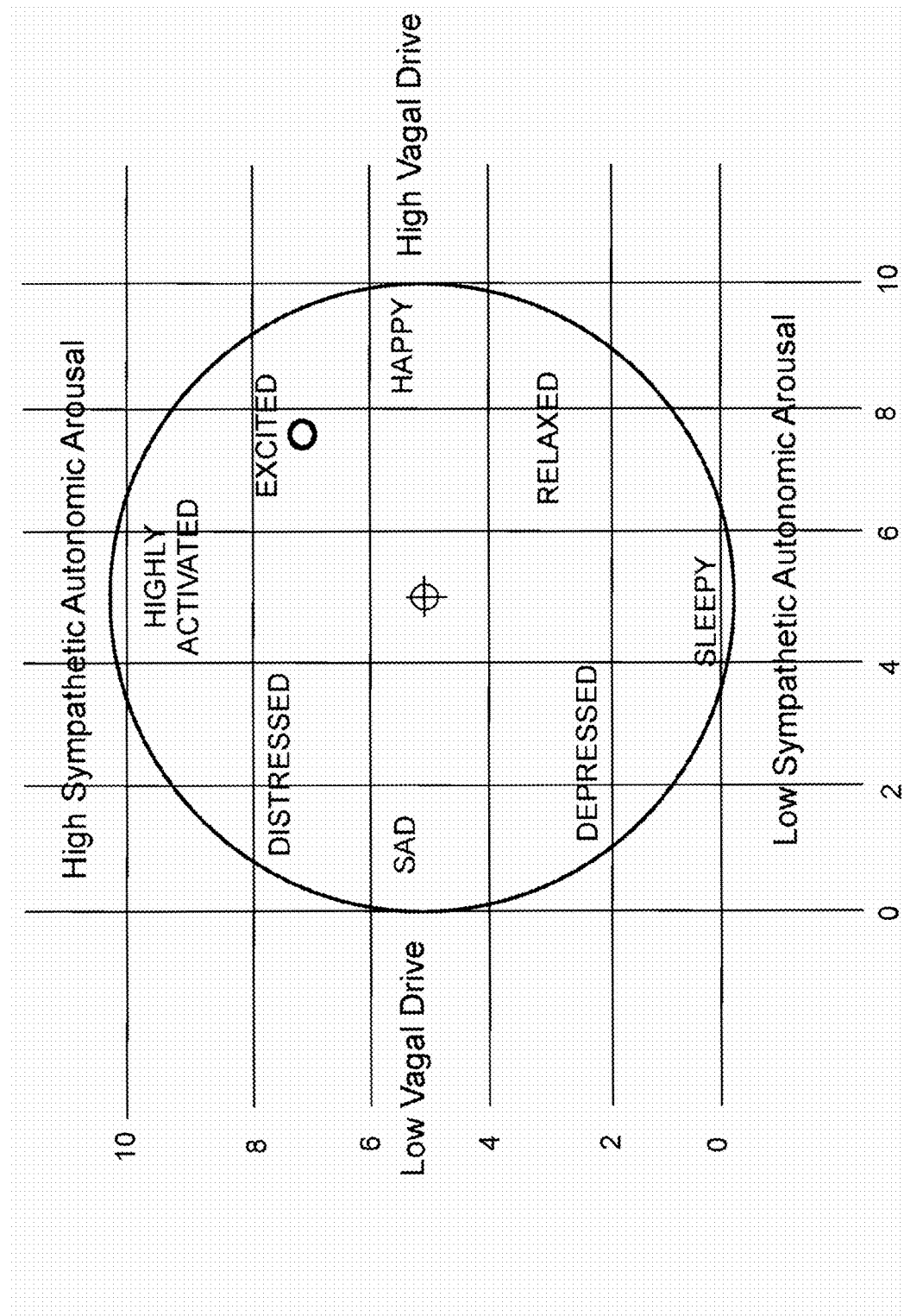
FIG. 14 shows location of an audio track in the emotional-mood space.

Average the two valence indices (NNVI and PVHI): the resulting valence value is 7.9. Plot the values on the colour circle as shown in FIG. 14.

Figure 15:
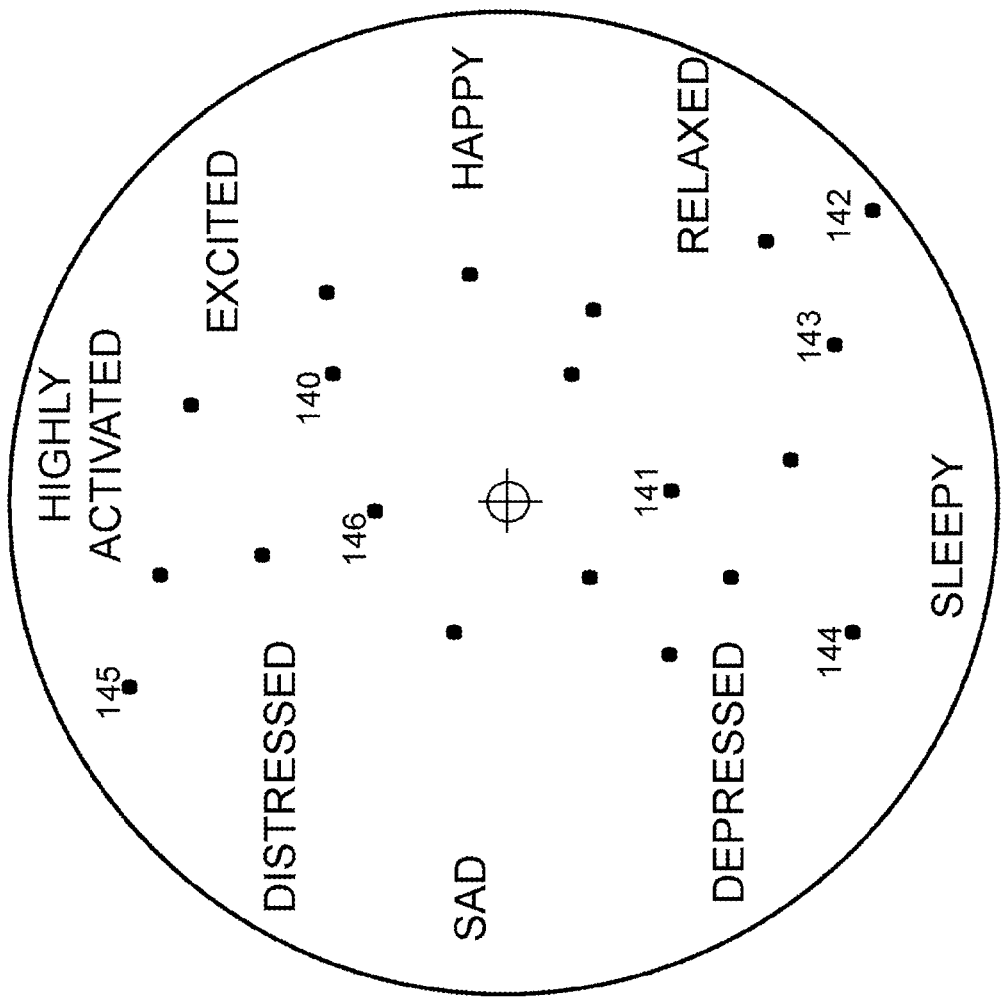
FIG. 15 shows locations of audio tracks in the emotional-mood space.

FIG. 15 shows some examples of X-System predictions and their locations in emotion-mood space. Pharrell Williams Happy 140 for example is located, where it may be expected, on the borderline of happy and excited. But it is also quite close to the borderline with more negative emotions. This reflects the edgy, and for some listeners, slightly ominous character of the song, generated in part by its haunting, unexpected combination of minor, modal and major chords (with contradictory major and minor sevenths and even a fierce de picardie). The opposite is true of Johnny Cash s Hurt 141. The sad, minor character of the verse pushes the song where it may be expected, in a negative direction. But in spite of the words, which X-System does not process, the chorus is quite bright, and this places the song as a whole at the far, negative edge of relaxed. This X-System prediction was verified by measurement of HRV in listeners, where the song showed a medium-to-high vagal power of 1150.

The most relaxing track in this selection of music is Gustav Holst s Venus 142 from the Planets Suite, with the Sanskrit, Vedic chant from Hanumat Panchashat 143 close by. Interestingly the Adagio from Beethoven s Moonlight Sonata 144 is relaxed/sleepy but leaning towards more negative emotions. Indeed, many listeners find that there is an elusive darkness in the piece.

Nirvanas Aneurysm 145 is the most arousing track, located between high activation and distress. Much heavy metal music appears to play with the ambiguity between constructive and destructive high energy. Led Zeppelins Whole Lotta Love 146 is lower down the arousal scale than might be expected. This is because of the extended abstract, Theremin section in the middle of the track.

X-System is capable of automatically predicting arousal with high accuracy and emotion and mood with improving accuracy in all world repertoires of music. It may automatically select music to sustain a particular level of physiological arousal, emotion or mood, or to help the listener navigate journeys and adventures through different states and experiences of mind and body.

An Example of Mood and Emotion Prediction Applied to a Specific Repertoire

As an example, Serbian Pop music is analysed: SERBIAN POP. It is well known that Serbian popular music is "hyper", due to a combination of cultural and historical reasons. What is interesting is that the X-System analysis shows a dense cluster of tracks, leading from the middle of the circle of emotion to "excited" and "highly excited" with increasing positive valence.

Figure 16A:
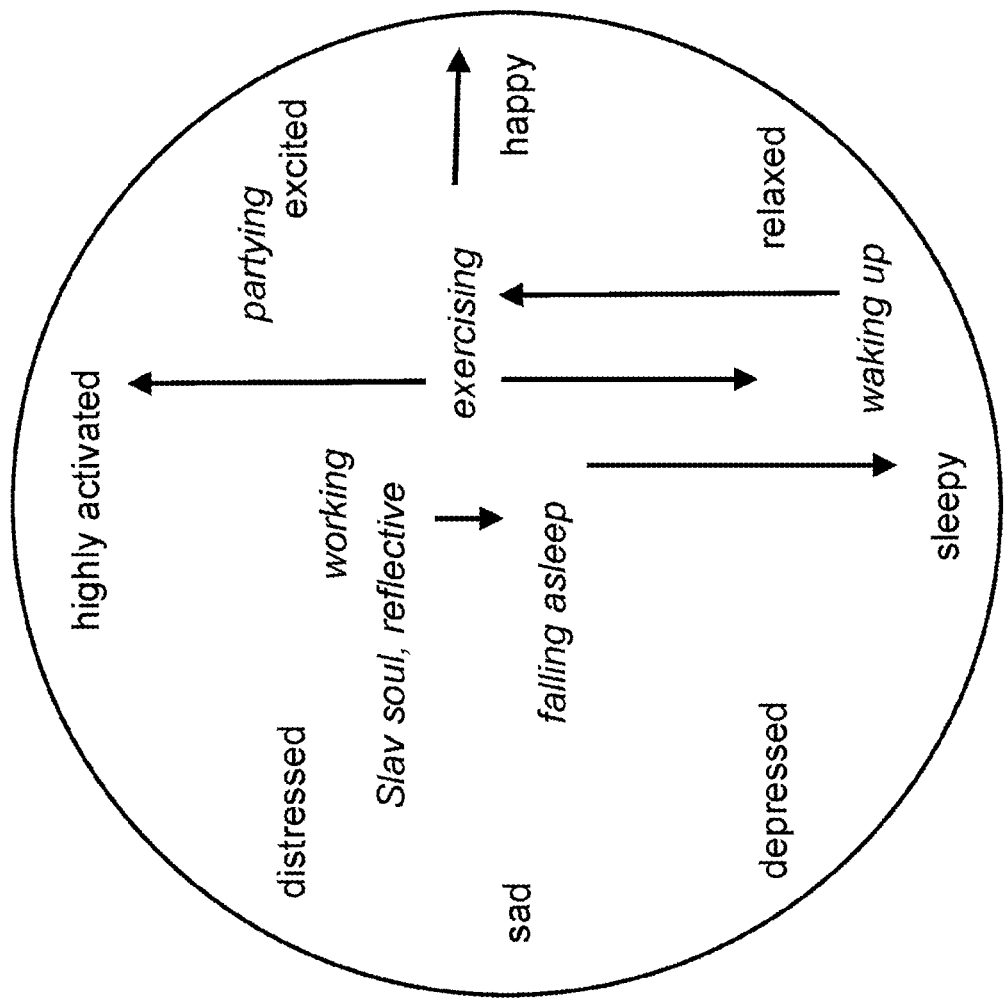
FIG. 16A shows how the emotions relate to physical activities on the emotional-mood space.

FIG. 16A shows how the emotions may relate to physical activities on the circle of emotions.

Figure 16B:
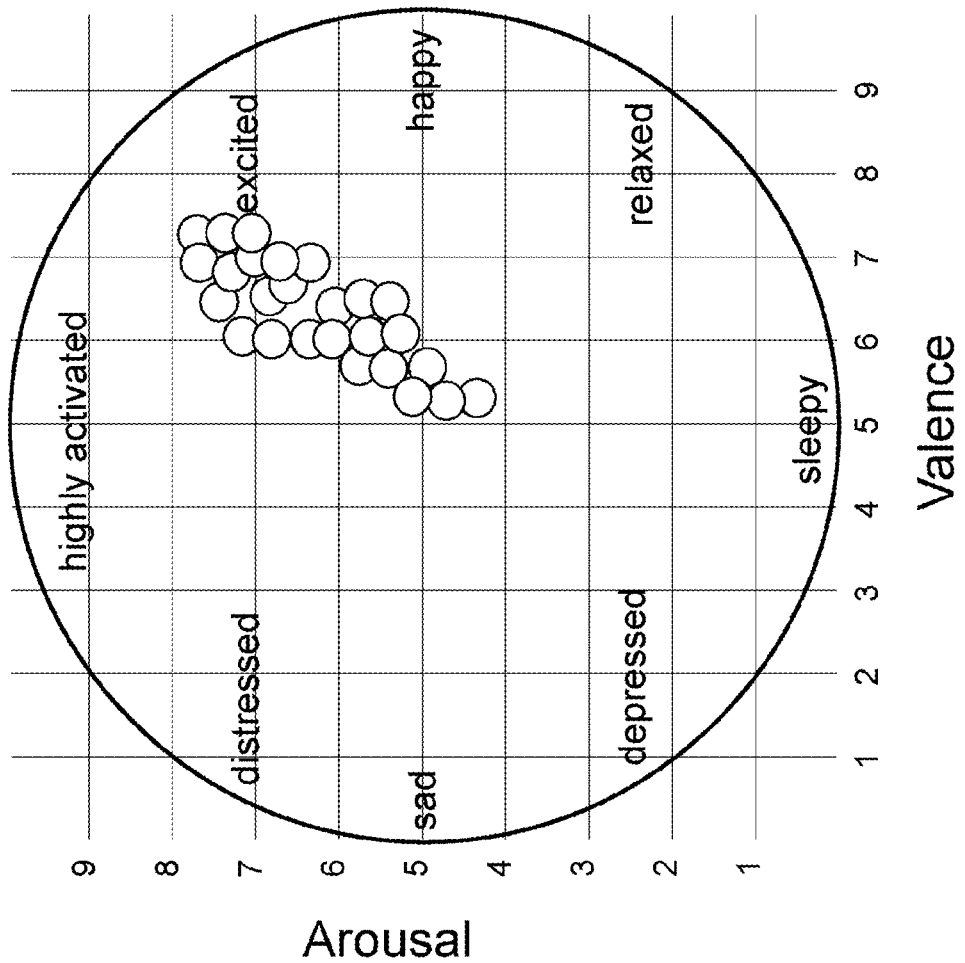
FIG. 16B shows a cluster of Serbian popular genres audio tracks located on the emotional-mood space.

FIG. 16B shows and how Serbian popular genres may be located within the circle of emotions. The cluster appears to fall into two parts—a high arousal cluster corresponding to "partying", and overlapping in part with "working", and a cluster gathered around "reflective", also overlapping with "working".

The high arousal, "partying" cluster is made up of a mixture Turbo-Folk, Dance Music influences and some Pop and Rock. Turbo-Folk is a Near/Middle Eastern, Roma-like form which ironically and paradoxically rose to popularity during a period of extreme nationalism and xenophobia in Serbia.

The lower arousal, "reflective" cluster is a mixture of styles and influences. There are songs in a popular style which could be described as "Slav soul", both sad and whimsical at the same time, There are less frantic versions of Turbo-Folk, the influence of "Gradska" music (the cabaret-like music of former Yugoslav towns) and Sevda (Sevdah, Sevdalinka), the music of unrequited love of Bosnia and South Serbia. Many of the songs have sad words: Nocas mi se ne spava (At night I do not sleep), On ne voli me (He does not love me), Casa Greha (A glass full of sin), Kuda idu ostavljene devojke (Where do abandoned girls go to?), but X-System correctly places these tracks in the middle of the colour circle: the sadness is self-conscious and self-indulgent; it is love-sick and bitter-sweet. It plays with sadness rather than entering it in full like, say, Gary Jules' Mad World or Gorecki's Symphony of Sorrowful Songs.

What can X-System offer to do with these classifications?

1. X-System can automatically categorise music in terms of arousal and valence (i.e. in terms of emotion) and relate these classifications to physical activities; for example high arousal and positive valence to "partying", or very low arousal to "falling asleep".

2. It can automatically edit existing playlists, removing outriders and ordering sequences in terms of X-System parameters (arousal, valence, rhythmicity, harmonicity, turbulence etc.).

3. Using arousal, rhythmicity and BPM, it can automatically sequence "partying" track playlists to increase or decrease arousal and dance-ability; it may also create more sophisticated sequences—for example, high arousal/dance-ability to low arousal, back to even higher arousal/dance-ability, then back to low arousal and intimate dancing for the end of the evening, like an automated DJ. A simple Turbo-Folk partying sequence of increasing arousal could, for example, be: Casa greha (arousal 6.04)-Hej kafano (arousal 7.2)-Kada odem (arousal 7.59).

4. It can use arousal and rhythmicity to automatically sequence music for work, once again either rising or falling in energy, sustaining effort at the same level, or indeed following more complex profiles of energy change.

5. Using arousal, rhythmicity, BPM and valence, it can automatically stream music for exercise, for example accelerating from jogging to sprint, preparing a swimmer for a burst of energy, or maintaining a rhythm for cycling on the flat. Here, for example, is a short sequence leading from a jog to a slow run: Ko mi to uspavljuje-Samo jedno-Samo tebe znam.

6. It can automatically sequence falling asleep and waking up sequences. In this particular repertoire there are unfortunately insufficient options for this.

The only remotely "sleepy" song is Kuda idu ostavljene devojke, sung by Ceca (pronounced Tsetsa), wife of former ice cream salesman and ethnic cleanser, Arkan.

7. X-System may automatically sequence simple journeys in both arousal (relax me, excite me) and emotion, for example musical journeys leading from sad to happy, or from depressed to relaxed (once again the latter would not be available within this particular repertoire). An almost sad to almost happy sequence could be: Jos pomislja na najgore-Hajde vodi me odavde-Odnesi me.

8. X-System may automatically select tracks or sounds that have a desired effect on how someone interacts with a web site, or web advertising, or search results from a search engine. For example, specific tracks or sounds can be selected to optimise the likelihood of a web user watching a video advert, or clicking through on a link, or buying a product or service online. For example, it might be that with some products or services, the objective could be to maximise the chance of a web user entering a 'happy' mood, and appropriate music tracks could then be selected and played. Because the automatic track or sound selection does not depend on lyrics but is language and culturally agnostic, the system is scalable to work automatically for any country or nationality.

X-System may therefore be used for the following use case applications:

automatically classifying music in terms of arousal and valence (mood/emotion).

automatically classifying music in terms of physical activities.

automatically constructing a playlist in terms of preselected desired mood or emotion to be experienced by a listener.

automatically constructing a playlist in terms of a preselected sequence of mood and emotion to be experienced by a listener automatically constructing a playlist in terms of preselected physical activity.

automatically streaming music depending on the listener's activity, such as working, exercising, driving, seeking pain relief, seeking relaxation, seeking mood enhancement.

selecting sound or music to stream or otherwise provide to someone viewing online content.

selecting sound or music to stream or otherwise provide to someone viewing or listening to online content to optimize the likelihood of that person reacting in a desired way to that content, such as reading or viewing or listening to that content, or purchasing goods or services advertised or promoted by that content.

APPENDIX A

A full description of a version of X-System is in PCT/GB2012/051314, the contents of which are incorporated in this Appendix.

Method and System for Analysing Sound

Background of the Invention

1. Field of the Invention

The present invention relates to a method and system for analysing sound (e.g. music tracks). Tracks from a database of sounds, for example music, can be analysed in order to predict automatically the effect or impact those sounds will have on a listener.

2. Technical Background

It is well established that there are specific levels of neuro-physiological arousal (related to mood, states of mind and affect) best suited to particular activities such as study, relaxation, sleep or athletic performance. However, because these levels of arousal result from complex interactions between the conscious mind, environmental stimuli, the autonomic nervous system, endocrine activity, neurotransmission and basal metabolism, it is difficult to control and sustain them.

It is also well established that there is a universal human response to music based on a complex set of functions ranging from perceptual systems, by way of cerebral cortex and other processing, to activation of core emotional centres of the brain and the somatic systems. It is similarly well established that these functions reside in parts of the brain such as, for example, the cochlea, primary auditory cortex, pre-motor cortex, amygdala and the periaqueductal grey (and so on). Rhythm, for example, has a measurable effect on the pre-motor cortex, autonomic nervous system, somatic systems, the endocrine system and neurotransmission. Other aspects of musical structure and experience may also influence human neurophysiology, as described below.

3. Discussion of Related Art

Three ways are known of analysing music for arousal and counter-arousal using humans (for brevity, the term 'arousal' will at times be used to include counter-arousal in this document). The first method entails the judgment of an individual, who might be either an expert or the subject him or herself. The second method is by testing many people and asking them how they feel in response to different music tracks. Neither is reliable because each is too subjective.

The third method is to analyse metrics computed as a function of the music itself (usually tempo, but may also include a measure of average energy), and relate such metrics to the desired state of arousal of the subject. There are several such systems, some of which are cited below. Most rely on either 'entrainment' (in the Huygens sense, namely the tendency to synchronise to an external beat or rhythm) or on the association of increased tempo (and in one known case, energy) with increased effort or arousal (and the converse for reduced tempo and energy).

Examples of prior art systems that use music selected according to tempo to manipulate arousal and counter-arousal include U.S. Pat. Nos. 282,045, 191,037, 113,725, 270,667, WO 151116, U.S. Pat. No. 5,267,942). This art may use beats per minute as calculated to predict entrainment or may, as in U.S. Pat. No. 060,446, modulate tempo in order to improve entrainment. Although this art may be directionally correct, and by extension of Huygens' entrainment principle, it is likely to work to some extent with some repertoire, tempo is both difficult to detect automatically and on its own may best be used to calculate neuro-physiological effect in the limited circumstances where the tempo is both easily and accurately detected and where it is close to the current heart rate of the listener (see next paragraph). Any significant divergence and the entrainment effect is likely to be lost. Most significantly, as discussed below, effective rhythmic entrainment depends on more than beats per minute, and is inseparably synergetic with and dependent on other musical generators of arousal, such as, for example harmonicity and turbulence.

U.S. Pat. No. 5,667,470 relies on the fulfilment or denial of expected outcomes in music in comparison with established patterns in the repertoire, while U.S. Pat. No. 4,883,067 introduces the concept of training the brain to replicate positive patterns of neurological activity by association with certain sound signals. One patent, U.S. Pat. No. 5,267,942, cites the iso-moodic principle documented by Altshuler in 1948 as evidence for its assertion that for the tempo of music to have any effect in entraining heart rate it must lie within the 'entrainment range' of the individual's actual heart rate, i.e. close to it. This introduces the notion that the neuro-physiological effect of a piece of music depends on the initial state of the subject, which means that the effect of any given piece of music is relative rather than absolute. Reference may also be made to US 2007/0270667 attempts to use biometric feedback to manipulate arousal.

Reference may also be made to psychoacoustics. Psychoacoustics has been extensively used in music compression technology (e.g. MP3), but another application is documented in U.S. Pat. No. 7,081,579, which describes an approach to song similarity analysis based on seven measured characteristics: brightness, bandwidth, volume, tempo, rhythm, low frequency noise and octave. These techniques can identify 'soundalike' music (of which there is much these days) but cannot be used to predict the effect of music in neuro-physiological terms.

Summary of the Invention

The invention is a computer implemented system for analysing sounds, such as audio tracks, the system automatically analysing sounds according to musical parameters derived from or associated with a predictive model of the neuro-physiological functioning and response to sounds by one or more of the human lower cortical, limbic and subcortical regions in the brain;

and in which the system analyses sounds so that appropriate sounds can be selected and played to a listener in order to stimulate and/or manipulate neuro-physiological arousal in that listener.

The model is a 'predictive model of human neuro-physiological functioning and response' because it predicts how the brain (e.g. structures in the lower cortical, limbic and subcortical regions, including the related autonomic nervous system, endocrine systems, and neuro-transmission systems), will respond to specific sounds.

In one implementation, tracks from a database of music are analysed in order to predict automatically the neuro-physiological effect or impact those sounds will have on a listener. Different audio tracks and their optimal playing order can then be selected to manipulate neuro-physiological arousal, state of mind and/or affect—for example to move towards, to reach or to maintain a desired state of arousal or counter-arousal, state of mind or affect (the term 'affect' is used in the psychological sense of an emotion, mood or state).

We can contrast this system with conventional psycho-acoustics (underlying for example MPEG MP3 audio compression algorithms) because psychoacoustics in general deals with how incoming pressure waves are processed by modelling the signal processing undertaken by, for example, the cochlea and primary auditory cortex, whereas the present invention deals with the effect of sound—e.g. the neuro-physiological functioning and response to sound in the lower cortical, limbic and subcortical regions of the brain. Also, the science of psychoacoustics is not concerned with selecting specific sounds for the purpose of stimulating and manipulating desired states of arousal in a listener.

We can also contrast this system with a trivial model of musical effect, such as increased tempo leads to greater arousal. Missing entirely from such model is a generalised understanding of neuro-physiological functioning and response to sound; furthermore, in practice, such a model is so weak as to have no genuine predictive property and, for the reasons given above, is not a general solution to the technical problem of selecting different sounds so as to stimulate and manipulate arousal levels in a listener, unlike the present invention.

The musical parameters derived from or associated with the predictive model may relate to rhythmicity, and harmonicity and may also relate to turbulence—terms that will be explained in detail below. The invention may be used for the search, selection, ordering (i.e. sequencing), use, promotion, purchase and sale of music. It may further be used to select, modify, order or design non-musical sounds to have a desired neuro-physiological effect in the listener, or to permit selection, for example in designing or modifying engine exhaust notes, film soundtracks, industrial noise and other audio sources.

The invention is implemented in a system called X-System. X-System includes a database of music tracks that have been analysed according to musical parameters derived from or associated with a predictive model of human neuro-physiological functioning and response to those audio tracks. X-System may include also a sensor, a musical selection algorithms/playlist calculator for selecting suitable tracks and a connection to a music player. Once the sensor is activated, the system diagnoses the subject's initial level of neuro-physiological arousal and automatically constructs a playlist derived from a search of an X-System encoded musical or sound database that will first correspond to or mirror this level of arousal, then lead the listener towards, and help to maintain her/him at, the desired level of arousal. The playlist is recalculated as necessary based on periodic measurements of neuro-physiological or other indicative signals.

Measurement of neuro-physiological state may be done using a variety of techniques, such as electro-encephalography, positron emission tomography, plasma, saliva or other cell sampling, galvanic skin conductance, heart rate and many others, while prediction of response may be achieved via any suitable set of algorithms that are first hypothesised and then refined through testing. Any given set of algorithms will be dependent on the stimulus being modelled and the biometric by which the effect of the stimulus is to be measured, but, even given constant parameters, there are a number of valid mathematical approaches: the specific algorithms we describe in this specification themselves are therefore not the most fundamental feature of the invention, even though most algorithms in the system are unique in conception and implementation. Nor are the particular biometrics chosen to measure neuro-physiological state, though galvanic skin conductance and heart rate are both suitable for general use because they enable measurements to be taken easily and non-invasively, while both give a good indication of arousal or counter-arousal in the autonomic nervous system, which is in turn largely synergetic with endocrine activity and related neurotransmission.

X-System represents an improvement upon existing art in that it: a) describes the bio-active components of music (beyond tempo and energy) by reference to the brain's processing of audio stimuli, including music, and b) describes how any given sound source may be calibrated to the initial state of the subject in order to have the maximum entrainment effect. It offers the advantage over many other systems that it requires neither the modulation of tempo (tempo modulation is known from US 2007/0113725, US 2007 0060446 A1, US 2006/0107822 A1) nor the composition of psycho-acoustically correct, synthetic music (known from U.S. Pat. No. 4,883,067) to achieve its effect. X-System offers the possibility of harnessing the entire world repertoire of music to the modulation of affect without needing to manipulate the rendering of the music in any way.

X-System is based on a paradigm we shall refer to as the 'Innate Neuro-physiological Response to Music' (INRM—we will describe this in more detail below), and a unique informatic modelling of one or more of lower cortical, limbic and subcortical functions related to these responses. X-System has a unique capacity to analyse music tracks automatically and establish the potential to generate levels of arousal and counter-arousal in the listener. This unique method of analysis is a human universal and may be applied to music of all human cultures as well as to environmental and other sound sources. X-System is capable of categorising databases of music and sound according to core emotional effect. X-System may implement automatic categorisation remotely, for example for personal repertoires. X-System may also have the capacity to detect the state of mind and body of the user, using a unique radio electrode and microphone based conductance/heart rate sensor and other devices. X-System may use this sensor data to subselect music from any chosen repertoire, either by individual track or entrained sequences, that when listened to, will help the user to achieve a target state of excitement, relaxation, concentration, alertness, heightened potential for physical activity etc. This is achieved by analysing music tracks in the user's database of music (using the musical parameters derived from the predictive model of human neuro-physiological response) and then automatically constructing a playlist of music, which may also be dynamically recalculated based on real-time bio-feedback, to be played to the user in order to lead her/him towards, and help to maintain her/him at, the desired target state.

As noted above, X-System models the effect of music on specific parts of the lower and middle brain, including the limbic system and subcortical systems, but these are not the only parts of the brain that respond to music. Other centres govern a more personal experience involving preference, culture, memory and association, the meaning of the lyrics, the historical context in which they were written, the knowledge of the circumstances of the performer or composer and other factors. These too have a significant effect, so it is important not to expect any piece of music to have an absolute effect on any one individual. INRM describes an important part of, but not all, musical effect. A prediction that certain pieces of music will calm the listener, or even induce sleep, is not like a drug or an anaesthetic, where the effect of a certain dose can be predicted with reasonable accuracy and where that effect cannot be resisted by conscious effort. Nevertheless, tests confirm that each of the elements of the brain that the INRM model is based on are strongly linked to arousal and counter-arousal. Music though, has its greatest effect when selected appropriately to accompany a desired state or activity and X-System offers an automated means of selecting music that is always appropriate to what the listener is doing, which can be very effective in a host of situations from treating anxiety to enhancing relaxation or concentration, or stimulating creative 'flow', or in bringing power and fluency to athletic activity. The brain modelling that underpins X-System offers a further capacity offered by no other existing categorisation system: it is universal; X-System may accurately predict levels of physiological arousal for all music of the world repertoire, whether it be Western classical and pop, Chinese or Indian classical or folk music, African pop or roots, or avant-garde electronica or jazz.

X-System has proven to be capable of outperforming expert musicologists in predicting, over a broad repertoire, a general index of arousal/counter-arousal based on the biometric parameters of heart rate and galvanic skin resistance, but were these biometric parameters to be different the equations, which we will describe later in this document, would almost certainly need to be modified; equally, there are many mathematical techniques familiar to those skilled in the art that could have been used to predict the neuro-physiological effect of a piece of music and any one of many might produce equally satisfactory results. A key feature of this invention therefore lies in the identification of the patterns in music that are neurophysiologically active ('bioactive') and that may have a predictable effect on human neurophysiology, including arousal and counter-arousal.

Other Aspects of the Invention

We list fifteen further aspects of the invention below, each of which may also be combined with any other:

1. A computer-implemented method of categorizing sound (such as any piece of music regardless of genre or cultural origin) (e.g. according to musical parameters derived from a predictive model of human lower cortical, limbic and subcortical neuro-physiological functioning and response to the pieces of music) in such a way that it may be selected (e.g. automatically based on biometric data captured by a sensor) to entrain neuro-physiological arousal towards a target level; this may occur while directing the listener towards one or more among a number of pre-assigned states of mind and/or affect, or in order to direct the listener towards one or more among a number of pre-assigned states of mind and/or affect.

2. Automatic categorisation of sound (such as pieces of music) in a remote database (e.g. according to musical parameters derived from a predictive model of human lower cortical, limbic and subcortical neuro-physiological functioning and response to the pieces of music). This includes the idea that we can search/discover music that has similar X-System deep structures and cross match conventional categorisation schemes (Gracenote® etc) to X-System. As an alternative to, or in addition to, automatic categorisation, X-System provides selection and 'push' for commercial or promotional purposes, or a methodology for description or detection of particular music, for all applications, not only entrainment. An example is a computer-implemented method of categorizing any piece of music regardless of genre or cultural origin according to its Innate Neuro-physiological Response to Music for the purpose of search, navigation, music discovery, retrieval and selection.

We now expand on the concept of search/discovery, in which X-System provides for automated search of musical remote or local databases and of X-System encoded services. In this application, users may:

Search for music that has similar signatures to the music they tag that they like, by pressing a 'find more' or 'I like' key on their computer or Smartphone X-System device App. This will cross-match X-System encoding of universal arousal information with other individual features within an App (such as favourites, or frequently listened to) in order to create a new level of personalisation;

Search by and for patterns of listening preferences amongst social network groups, such that by sharing my preferences and choices and communicating them to my friends, they will see the relationships between my emotional response to particular tracks and comparisons with others in the network;

Search by musical or experiential journey, such that a particular sequence of music can be stored, for example, on my Smartphone and repeated when I press 'I liked that sequence, store it so I can play it again';

Search by finding patterns and relationships between tracks users tag as 'I like', such that similar combinations of say genre, musician, activity and X-System encoded arousal data can drive recommendations. So, for example, X-System will generate a playlist suggestion that will combine jazz, particular Miles Davis tracks, writing an essay, concentration and arousal levels, if a similar combination has been tagged from an earlier listening sequence (the tagging of activity being part of the Smartphone App); and Search on Google and other web sites for X-System encoded information, such that, for example, music, video or other web content is categorised and tagged, either automatically; or in collaboration with search engine providers such that it 'advertises' X-System arousal or mood states; or according to visitors who tag web sites automatically as they view pages.

3. An automated diagnosis of the level of lower cortical, limbic and subcortical neuro-physiological arousal of an individual and expressing it as a value in order to correspond to the musical effect of any one of a theoretically unlimited number of pieces of music in a database. Alternatively or additionally, there may be provided a method of trial and error of self-diagnosis e.g. by song selection as described above.

4. A computer-implemented method of creating a playlist of tracks generated by automatically (or indeed manually) analysing musical parameters derived from a predictive model of human lower cortical, limbic and subcortical neuro-physiological functioning and response to the pieces of music in order to entrain arousal and direct state of mind and/or affect. Optionally, this may include:

a) choosing a subset of the music in a database by reference to existing descriptive metadata, if available, such as genre or user-created playlist; b) selecting from this subset of music a number of pieces that will correspond to the user's initial level of lower cortical, limbic and subcortical neuro-physiological arousal by matching it to music contained in the relevant row of the musical effect matrix (we will explain this matrix in more detail later); c) selecting a target state of mind and/or affect; d) selecting a series of ascending or descending musical effect values which correspond to the expected entrainment path from the initial to the required level of neuro-physiological arousal; e) on the basis of this series of values, selecting qualified content from the music database; f) choosing at random a playlist from the qualified content subject to other rules such as genre preference, the anti-repetition rule (see 'Musical Selection Algorithms' below) or the Unites States' Digital Millennium Copyright Act (DMCA) rules; g) repeating the calculation of the playlist at intervals, based on continual biometric feedback—for example, the playlist may be recalculated once per minute, based on biometric feedback including the most recent feedback.

5. A method of determining the sufficiency of a (e.g. personal) database of music for the entrainment of affect and of then displaying information to the user with regard to sufficiency or insufficiency.

6. A method of recommending a complement of musical content for a personal database of music in order to ensure sufficiency, by using musical parameters derived from a predictive model of human lower cortical, limbic and sub-cortical neuro-physiological functioning and response to that music.

7. A method of selecting music which has a similar musical effect, (e.g. according to musical parameters derived from a predictive model of human lower cortical, limbic and subcortical neuro-physiological functioning and response to the pieces of music). This may include a search by X System code.

8. A method of categorising music according to its musical effect rather than its descriptive attributes.

9. A method of ordering a series of pieces of music in a playlist by matching the musical effect of each piece with a temporal series of values described by a musical effect vector.

10. A method of manipulating the arousal of a user by using any of the above methods or systems.

11. A method to modify the properties of ambient sound in any given environment, in order to produce a desired neuro-physiological response in the listener, by using any of the above methods or systems. And the use of this as a selection, control or design tool to define such responses.

12. A system adapted to perform any of the above methods.

13. Software (whether device-resident, network resident or elsewhere), firmware, SoCs or audio stacks programmed or adapted to perform any of the above methods or to form part of the system described above.

14. A computing device, such as a smartphone or tablet, adapted to manipulate the arousal of a user by using any of the above methods or by using or including any of the above systems, software, firmware, SoCs or audio stacks.

15. Sensors adapted to work with the computing device defined above.

Some more generalised observations now follow:

It is the identification of which structural and experiential phenomena in music activate which parts of the primitive brain, the development of techniques to measure them using digital signature analysis and the construct of a series of generic models that use relatively simple equations to predict levels of activation of relevant regions and organs of the brain, and in turn their effect on biometric indices, that are some of the key aspects of this invention.

Examples of the present invention may work with all musical genres and do not depend upon there being any pre-existing metadata in a database of digitised music. The database may be assembled by the user from his or her own collection and stored on a local playback device, in which case the music on the database may be profiled remotely, it may be supplied pre-analysed on a digital storage device, or it may be streamed from a central server. In these latter cases, the music may be associated with other data and/or digital media in order to enhance the user experience, or signature excerpts may be profiled and included in order to accelerate the desired effect.

The invention may be implemented as application software on either a remote server, on the music playback device itself or on another device that is connected to the music playback device either directly or via either a local or wide area network, or firmware or embedded in a chip; it may form part of an audio stack or may be used as part of a set of design tools. These implementations may enable real-time analysis of music tracks and other sounds, all done locally within a portable computing device such as a smartphone or tablet, or remotely on a server, or some combination of distributed local and server based processing. All such deployments will also support a consistent API to enable application vendors and service providers to access system capability, for example, to enable new application to be constructed and deployed.

If the necessary metadata are available, a preferred musical style may be chosen among those on the music database; if not, the system may select from the whole music database rather than a chosen subset.

The following terms are taken to have specific meanings in this document:

'Level of neuro-physiological arousal': an index calculated, for example, as a function of galvanic skin conductivity and pulse rate, though other parameters may also be selected including where more complex measurement is required. Different levels of neuro-physiological arousal facilitate different activities, states of mind and affect.

'State of mind': the dynamic relationship between functional areas of the brain associated with different types of thought such as creativity, learning, meditation, imagination etc.

'Affect' (noun): as used in psychology to mean feeling or emotion and in psychiatry to mean expressed or observed emotional response. Mood.

'Musical Effect': the state of mind or mood that is provoked by a given piece of music and the influence it has upon neuro-physiological arousal.

'Sound': includes any sound, including music as that term is conventionally understood but also extending to other sounds such as the ambient or background noise in a workplace, cinema, home, shop, vehicle, car, train, aircraft: anywhere where sound can in theory effect listener arousal. For example, tuning car exhaust notes would be one example; modifying engine sounds another. Sounds of nature (wind, ocean etc.), sounds of animals, sonifications (planets, stars, flowers, trees, financial markets, cell activity etc.) are other examples of 'sounds'. In this document, we will refer to 'music', but that term should be expansively construed to include not merely music in the sense of the art form in which voices and/or instruments are combined to give harmony, beauty or self-expression, but also all other forms of sound, as that term is expansively defined above.

A note on terminology: The primary auditory cortex is situated in the temporal lobes of the neo-cortex—the most "evolved" part of the brain, but it is essentially "low" in the system and hence 'lower cortical'. Organs critical to X-System, such as the hippocampus and amygdala are generally described as "limbic" (from the Latin "limen, liminis", meaning "threshold", i.e. at the lower limit of the neo-cortex). These are close to emotion-related areas such as the nucleus accumbens, and periaqueductal grey, sometimes also regarded as limbic. The limbic system may also be described as the archicortex and paleocortex—the "main, initial or ruling" and "old" cortex. Finally, many X-System areas related to rhythm, core emotion and movement are sub-cortical, for example the basal ganglia and cerebellum.

X-System therefore relates primarily to lower cortical, limbic and sub-cortical areas of the brain, concerned with fundamental and universal responses to music, as opposed to more cognitive-related, culture-related and reflective areas of the neo-cortex.

Detailed Description

This Detailed Description has the following sections:
A. High Level Concepts
B. The Innate Neuro-physiological Response to Music (INRM) in more detail
C. How X-System is used
D. The Sensor or Sensors
E. Musical Selection Algorithms
F. The Music Player
G. Diagnostic and streaming software
H. Manual categorisation
I. Manual categorisation vectors
J. Social Networks
K. Opportunities for Expansion/Enhancement
L. Benefits of X-System A. High Level Concepts There is scientific evidence that music entrains and shapes arousal, state of mind and affect through direct neuro-physiological engagement; this invention concerns the discovery and general method of determination of the Innate Neuro-physiological Response to Music, and includes a novel method of harnessing this phenomenon. As noted above, this invention is implemented in a product called X-System. X-System harnesses the potential of music to effect neuro-physiological changes in listeners, in particular in relation to arousal and counter-arousal and associated states of mind, working at the level of the most fundamental, innate, neuro-physiological functioning and response of the limbic, lower cortical and sub-cortical regions of the brain.

It differs from other approaches to music categorization in that it is not concerned with musical similarity, either by semiotic labelling or the analysis of acoustic characteristics. It also differs from standard therapeutic approaches, such as classification of mood.

Figure 17:
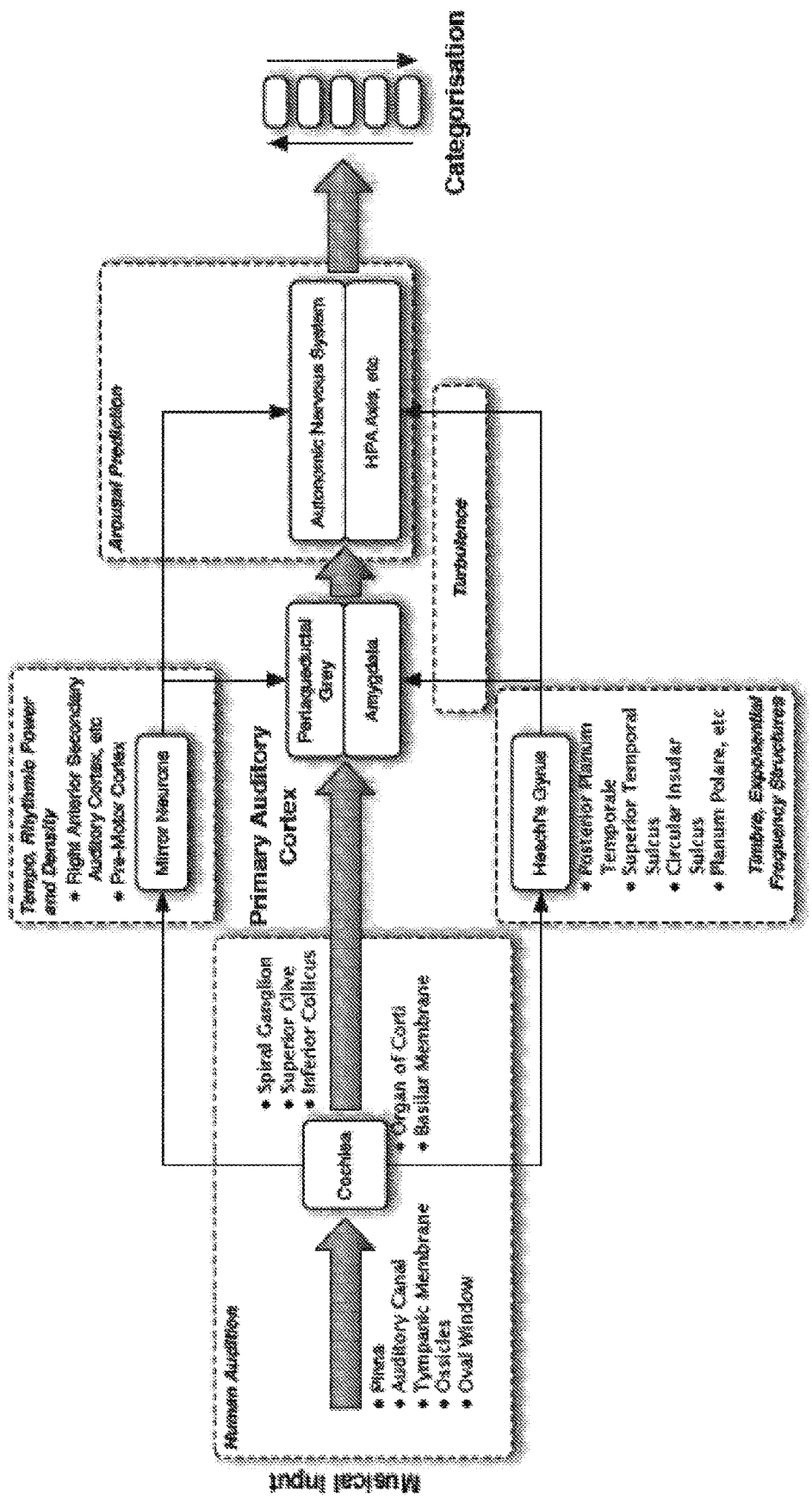
FIG. 17 shows a graphical representation of the neural elements involved in audio processing applicable to the X-System. Elements enclosed within the solid boxes are part of the current model; elements contained in the dashed boxes may be included in the model.

X-System works through predictive, deterministic modelling of INRM (Innate Neuro-physiological Responses to Music) (Osborne 2009, unpublished), see FIG. 17, and the structuring of pathways towards target states of body and mind. Section B explains INRM in more detail. In brief, the INRM paradigm assumes a standard interpretation of audition, from the auditory canal to the oval window of the cochlea. The cochlea itself is modelled to reproduce the characteristics of human audition. The paradigm further assumes neural pathways to the inferior collicus and primary auditory cortex. Levels of arousal related to pulse and rhythmicity are predicted through a simple modelling of mirror neuron and pre-motor related systems, including tempo induction and indices of rhythmic power and density. Other bio-active characteristics of music may also be modelled such as the identification of rhythmic patterns in the right anterior secondary auditory cortex, among others.

X-System additionally models the functioning of Heschls gyrus, the posterior planum temporale, superior temporal sulcus and circular insular sulcus to predict arousal-related qualities of timbre and exponential series-related frequency structures, including octave equivalences. There are other modelling possibilities such as arousal-related effects among chroma (individual notes of melodies) in the planum polare using, for example, harmonicity indices.

Finally, general levels of 'turbulence' are calculated as a prediction of arousal and counter-arousal in core emotional locations and organs such as the periaqueductal grey and amygdala.

The predictive arousal and counter-arousal values calculated are combined to model the process of arousal and counter-arousal in the autonomic nervous system, and associated systems such as the HPA (hypothalamic-pituitary-adrenal) axis.

A sensor may optionally be used to establish the state of arousal of the user, and music categorised by predictive modelling of the INRM paradigm can then be streamed/played back to achieve the target arousal state for that user. In an alternative implementation sensors are not provided. Instead, both initial and target states are self-selected, either directly or indirectly (such as, for example, by selecting a 'start song' which has an arousal value relative to the user's true current state). For example, where the user makes a poor initial selection, he/she might skip from song to song initially until one is found (i.e. by trial and error) that is both 'liked' and 'fits' with their initial state. From there, X-System, in a sensor-less implementation, may create a playlist tending towards the desired arousal state based on expected normal human response.

In another alternative, an implementation is provided for a group of people as a system with software but no sensor, reliant on average expected response. An application is for 'crowd' applications, where an automated disc jockey (DJ) would be able to manipulate the mood of a crowd at a party.

Other alternatives include applications controlling the personal audio environment by sending emotional cues to the system via sensors, and polling group emotion via either sensor or sensorless inputs, in order to entrain the person or group towards a desired response.

Other alternative applications include the search, selection, description, detection, sharing or promotion, of music based on its neuro-physiological content.

As in the case of all systems and activities related to music and arousal, there are variations in response among individuals, and variations as a result of extreme or unusual states of body and mind, medication etc. The strength of X-System is that it works on the basis of the most fundamental physiological responses, which may act in an ethical and democratic synergy with conscious and unconscious consent of the user. A further strength of the INMR-based categorisation system is that it may be applied to the music of any human culture, and indeed both to sound design and sounds of the natural world.

B. The Innate Neuro-Physiological Response to Music (INRM) in More Detail

FIG. 17 shows a simplified model of the neural structures related to auditory processing and interpretation. The X-System example of the invention may model the functioning or behaviour of these systems in response to sound (e.g. musical) stimulus as described in the following sections.

The Innate Neuro-physiological Response to Music Paradigm is a predictive, deterministic model of the mind and body's most fundamental response to music. Although responses to music are profoundly influenced by culture, personal history and context, there are basic neuro-physiological reactions that are universal to all musical experience. A substantial body of recent research in neuro-physiology and neuroscience, including evidence from functional Magnetic Resonance Imaging, EEG and Positron Emission Tomography, as well as studies related to endocrine and autonomic activity has made it possible to build a predictive model of how the lower cortical, sub-cortical and limbic parts of the brain react to sound.

X-System makes use of the following protocols for audio input. Input is taken from uncompressed WAV files or any other suitable format (X-System can use lower quality file formats when undertaking remote categorisation—e.g. categorising music tracks on a remotely held server or personal device. Equally, higher quality file formats may be more appropriate in other circumstances). If the track is in stereo, we combine both channels by averaging them. This is particularly important, for example, for 1960s tracks, where some loud instruments were positioned full left or right. This should not cause interference unless the audio has passed through faulty stereo equipment (e.g. a misaligned tape head). The track is split into sections of a given length, and the analysis is carried out independently for each section.

Figure 23A:
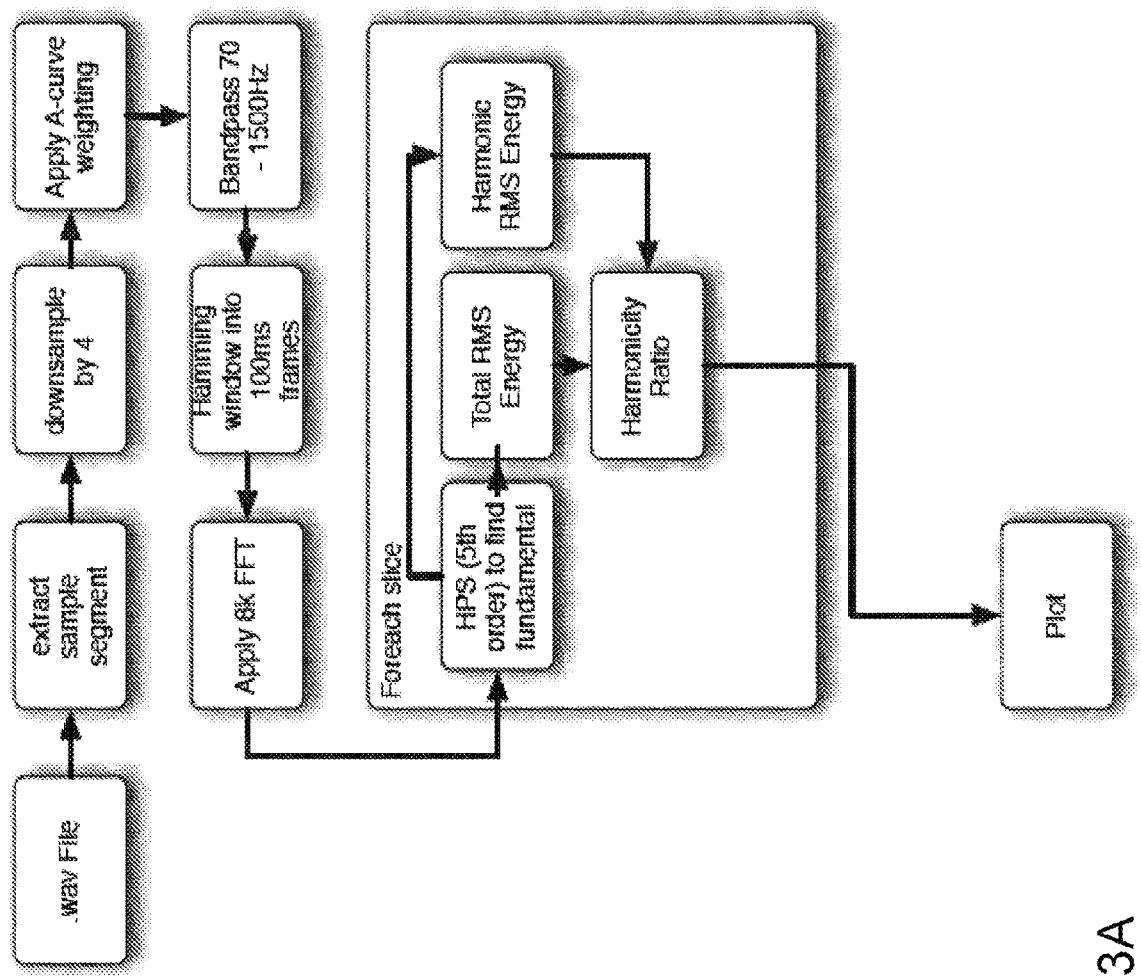
FIG. 23A is a detailed block diagram showing the major components of the X-System audio analysis tool used in analysing harmonicity.
Figure 23B:
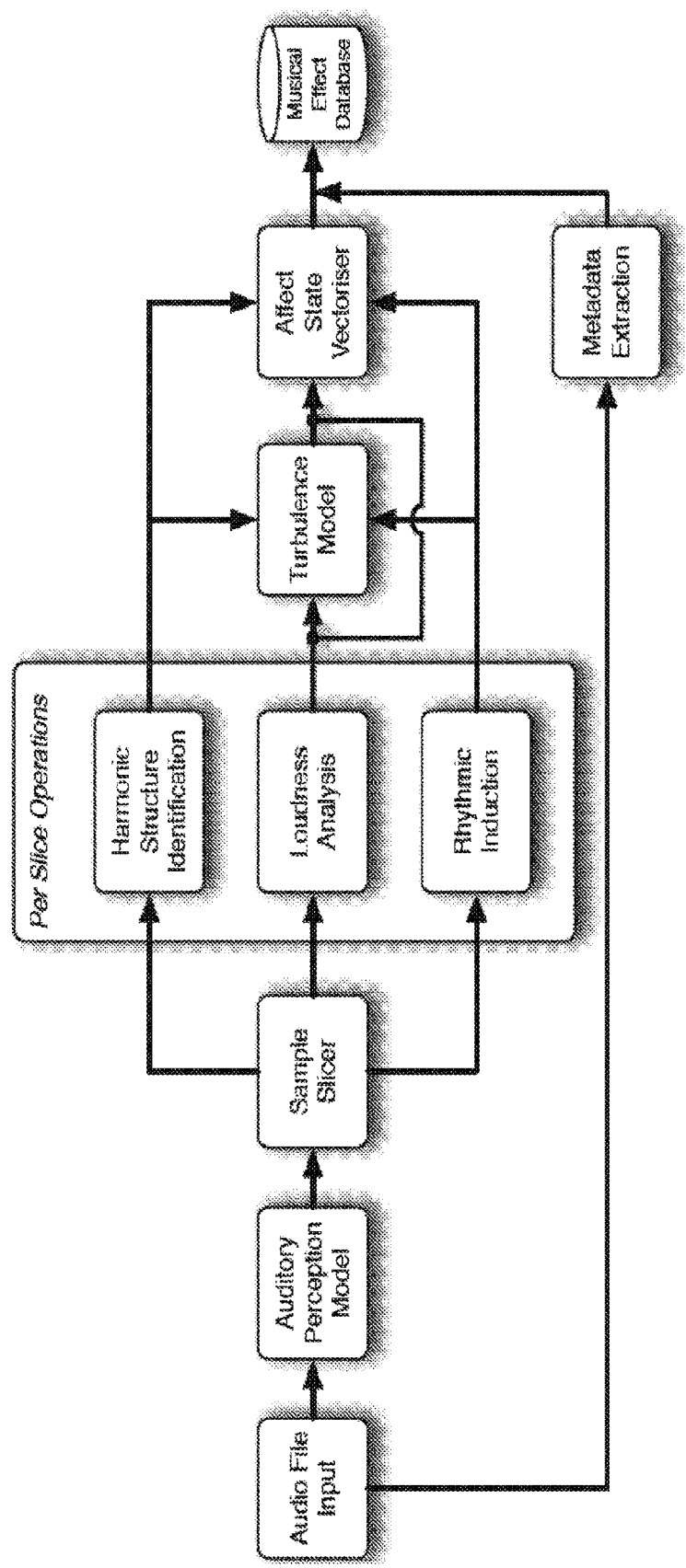
FIG. 23B is a detailed block-diagram showing all of the major components of the X-System audio analysis tool.

FIG. 23A is a block diagram showing the major components in X-System for analysing harmonicity and FIG. 23B is a block diagram representation of all of the major components of the musical analysis tool. The operation of the major components will be described in the remainder of this Section B.

B.1 the Cochlea and Primary Auditory Pathways

Figure 26:
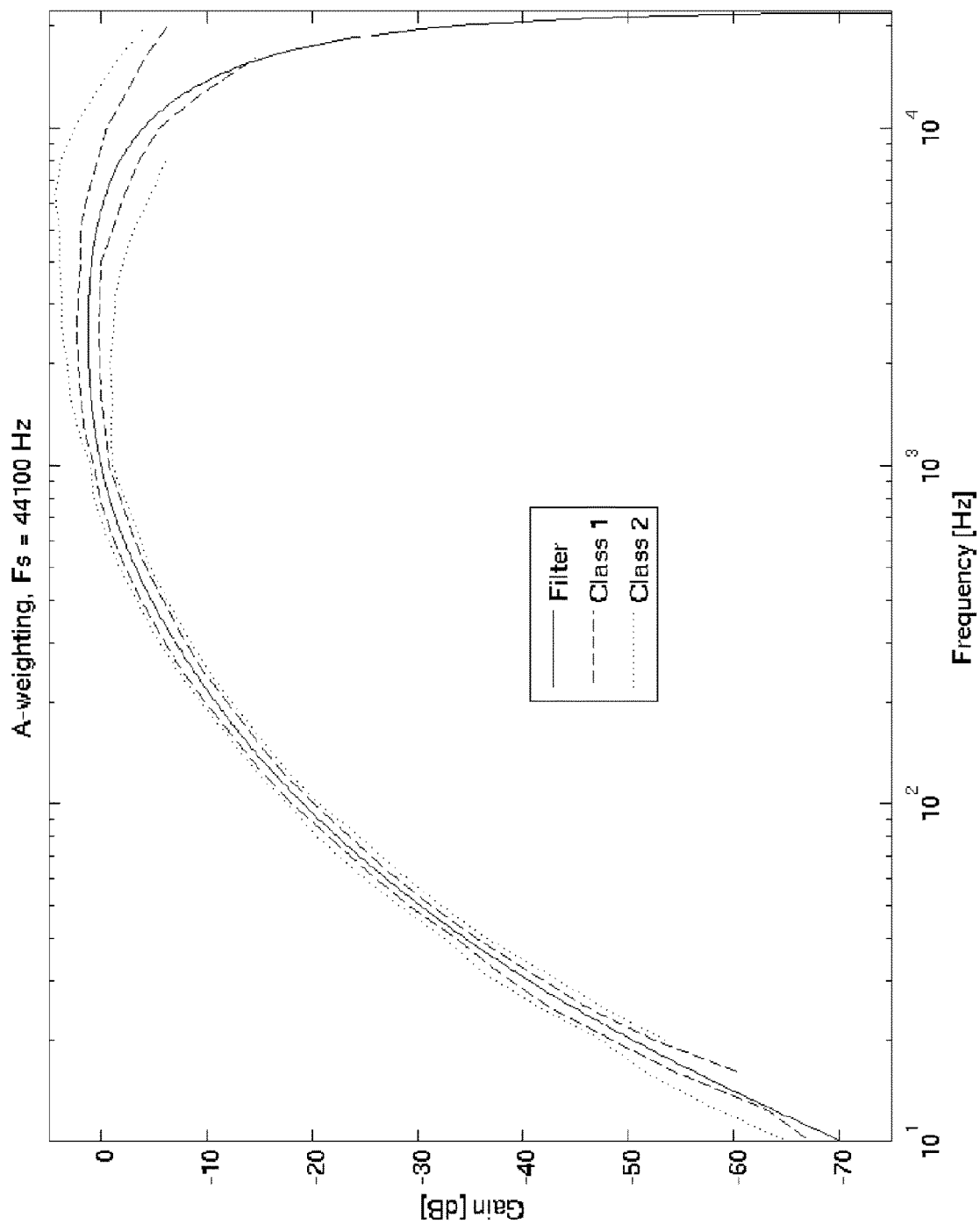
FIG. 26 shows the modelling of the cochlea and primary auditory pathways is achieved through the use of an A-weighting filter. This attenuates lower frequencies and amplifies higher frequencies, dropping off again quickly towards the upper frequency limit of human hearing.

Modelling of the cochlea and primary auditory pathways is achieved through the use of an A-weighting filter, as specified in IEC 61672. This attenuates lower frequencies and amplifies higher frequencies, dropping off again quickly towards the upper frequency limit of human hearing; the filter 'knee' is at around 6 kHz. This weighting is required to ensure that (as in human audition) high energy lower frequency sounds do not overwhelm other spectral information. See FIG. 26.

B.2 Harmonicity: Heschl's Gyrus and Associated Tonotopic Maps

"Harmonicity" describes the correspondence of sound (e.g. music) to the pattern of the harmonic series (harmonic series are present in the sound you hear when the winds blows through a hollow tree, run your finger lightly up the string of a violin or guitar, or blow progressively harder on a single note on a flute). The harmonic series is a universal pattern of concentrations of sound energy in symmetrical resonating objects: a fundamental tone f, sounds together with its harmonics f2, f3, f4 etc. This pattern has been important throughout the evolution of sentient life forms, from the harmonic resonance of the primal cell, through the perceived "safety" of harmonic sounds in the environment, to the pleasing harmonic resonances of musical instruments and the human voice. "Harmonicity" or correspondence to the pattern of the harmonic series is detected by Heschl's Gyms, located in the primary auditory cortex of the brain. Harmonicity activates centres of counterarousal and pleasure in core emotional centres of the brain. Inharmonicity, or lack of correspondence to the harmonic series activates systems of arousal.

X-System models the functioning and response of Heschl's Gyms to sound by determining levels of harmonicity and inharmonicity. This may be a complex process. Musical structures may involve several fundamentals each with their own harmonic or inharmonic spectrum.

X-System is unprecedented in that it combines all emotional processing of pitch and timbre in two harmonicity-related algorithms. Timbre (the internal structure "colour" of a sound), harmonicity (the extent to which the internal structure corresponds to the pattern of the harmonic series) and individual pitches are initially processed in the primary auditory cortex. The main area for processing timbre is the posterior Heschl's gyrus and superior temporal sulcus, extending into the circular insular sulcus (McAdams et al 1995; Griffiths et al 1998; Menon et al 2002). Pitch is processed progressively deeper in areas surrounding Heschl's gyrus: chroma (or differences of pitch within the octave, as in most conventional melodies), activate bilateral areas in front of Heschl's gyms and the planum temporale, while changes in pitch height (octave transpositions and the like, as in the difference between a man and woman singing the same tune) activate bilateral areas in the posterior planum temporale (Brugge 1985; Pantev et al 1988; Recanzone et al 1993; Zatorre et al 1994; Warren et al 2000; Patterson et al 2002; Formisano 2003; Decety and Chaminade 2003; Jeannerod 2004; Talavage 2004). Harmonicity and pitch structures activate areas of the amygdala and hippocampus, and in turn the autonomic nervous system, core emotional centres, and endocrine and neurotransmission systems (Wieser and Mazzola 1986; Blood and Zatorre 2001; Brown et al 2004; Baumgartner et al 2006; Koelsch et al 2006). X-System predictively models the neurophysiological sensing of simple timbre (Heschl's gyrus, superior temporal sulcus, circular insular sulcus) by analysing windows of vertical harmonicity: X-System detects a principal fundamental through calculation of the harmonic product spectrum, then establishes degrees of harmonicity both within and among the spectra of different fundamentals. This analysis is applied both "vertically" to instantaneous moments, and "horizontally" to progressions of pitches and spectra in time (related to the tonotopic mapping of the area around Heschl's Gyms) and expressed in terms of linear harmonic cost.

In one very simple implementation, the mean values of linear harmonic cost (C) and instantaneous harmonicity (H) are combined to calculate the inharmonicity (I) of a piece where:

$$I=C/10-H$$

Figure 28:
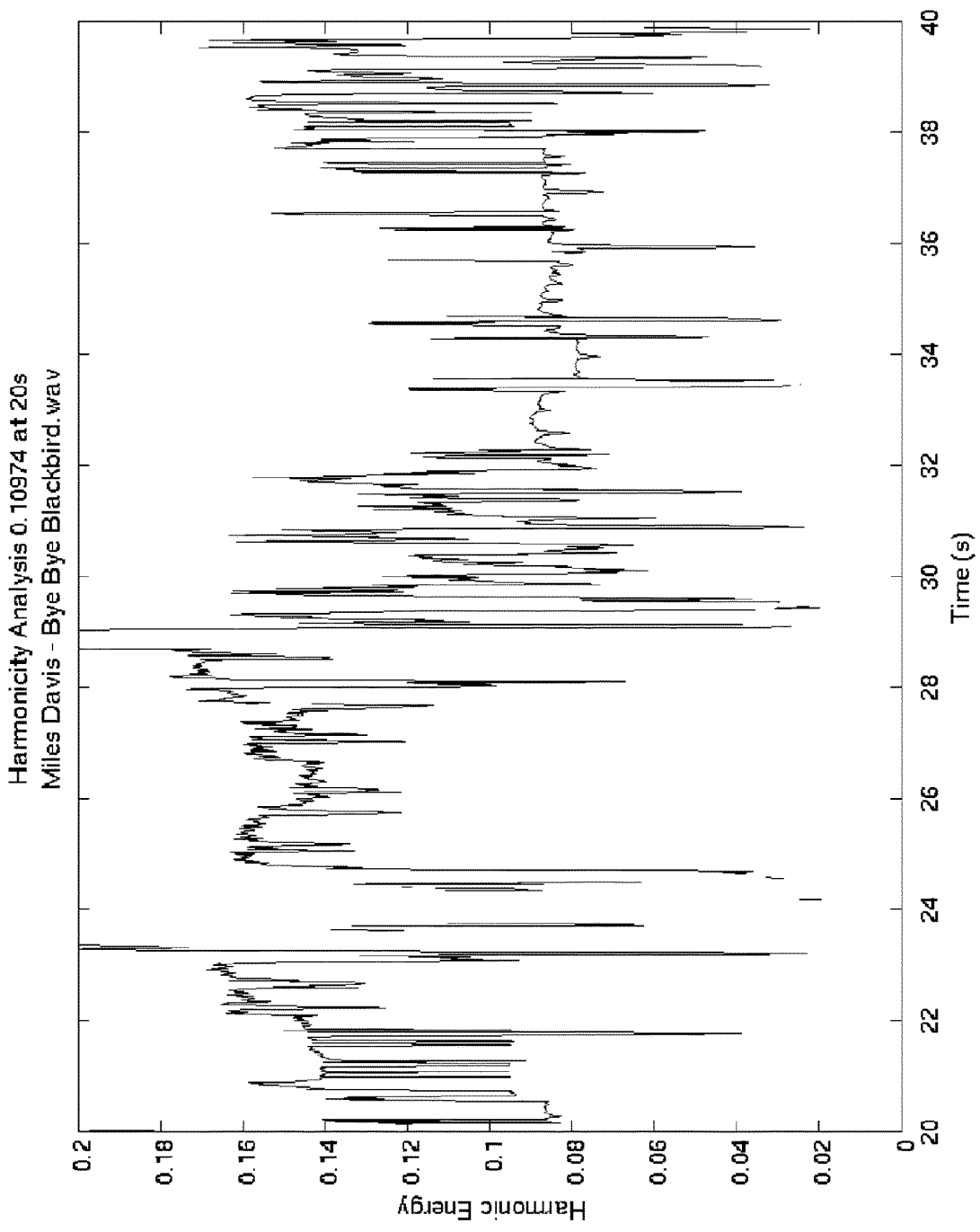
FIG. 28 shows Harmonic Energy as a function of time.
Figure 29:
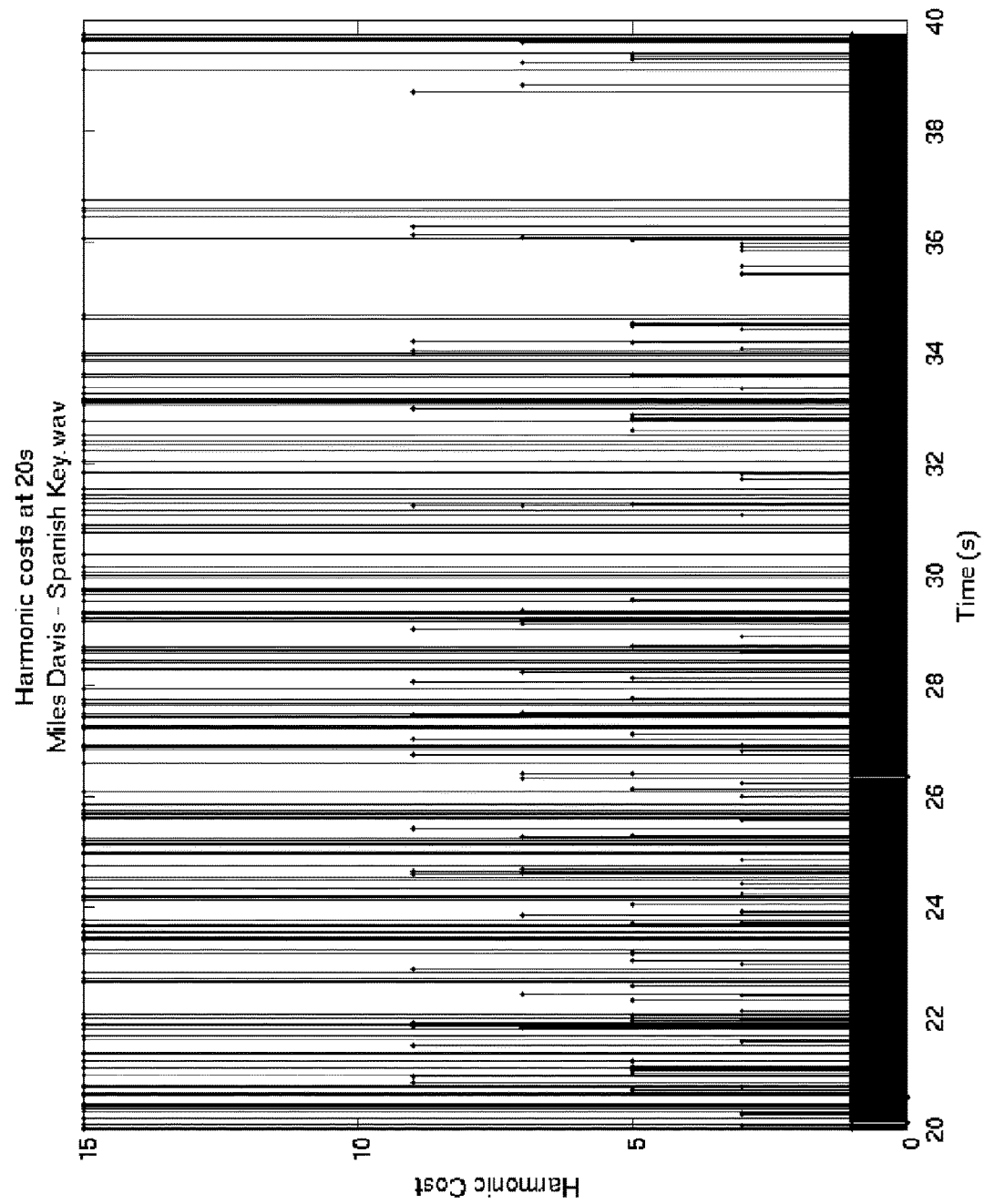
FIG. 29 shows Harmonic Cost as a function of time.

This equation is a non-limiting example of how inharmonicity can be calculated and other ways of linking I to C and H may well be appropriate; furthermore, I may be defined in terms of other or additional variables, as may C and H. See FIGS. 28 and 29, showing harmonic energy and cost as a function of time.

More details on Harmonicity calculation now follow:

B.2.1 Spectral Analysis

First the STFT of the audio is taken with a window length of 8192 samples and an interval of 2250 samples (0.05 seconds). This produces a 2D array of time vs frequency.

B.2.2 Cochlear Modelling

As in the case of rhythmic processing, analyses are performed on a transformed instance of the input sample data, which accounts for certain aspects of the auditory pathway, primarily the cochlea pick-up. The behaviour of the cochlea is well understood and accurate models have been developed. We apply a frequency-dependent gain function to the input signal, which attenuates bass signals and amplifies treble components, with a filter "knee" at around 6 kHz. The exact transform used is the "A Weighting" as specified in IEC 61672.

B.2.3 Fundamental Frequency Detection

For each time slice of the STFT array, the fundamental frequency is determined using the harmonic product spectrum method, as follows:

Take the frequency spectrum, and produce copies of it compressed along the frequency axis by factors of 2, 3, 4 and 5.

Multiply all 5 copies (including the original)

The fundamental frequency is the maximum value of the resulting spectrum.

B.2.4 Mean Harmonicity

For each time slice of the STFT array, the mean harmonicity is the ratio of harmonic energy to the total energy present in the slice. Harmonic energy is energy found in the following harmonics of the fundamental, as well as of ½ and ¼ of the fundamental: [1 2 3 4 5 6 7]. For each of these harmonics, we sum the energy found in the closest STFT bucket, plus 3 buckets on either side.

B.2.5 Linear Harmonic Cost

Predictions of activity in, and progression through, areas surrounding Heschl's Gyms (planum temporale, posterior planum temporale) including chroma, octave changes and chord progression etc. are combined in a single operation, described as "linear harmonicity" or "harmonic cost".

This is entirely unprecedented: it analyses all melodic and harmonic progressions in terms of how far each step deviates from the simple ratios of the harmonic series: Linear harmonic cost arises from STFT time slices whose fundamental frequency differs from that of the previous slice. Time slices with no change in fundamental have a cost of zero. The fundamental frequency is first normalised by rounding it to the nearest musical note value under the A440 tuning, then shifting it to a single octave. The (normalised) fundamental is then compared to the previous one: If they are identical, the cost is zero. If the new fundamental is one of the following harmonics and sub-harmonics of the previous (normalised) fundamental (1/9 1/7 1/6 1/5 1/3 3 6 7 9) then the cost is defined as equal to the multiplier of the harmonic or divisor of the sub-harmonic. Otherwise the cost is defined as 15.

Linear harmonic cost is expressed in terms of cost per second. The metric therefore represents both the rate at which the fundamental is changing, and the harmonic distance of the changes. Higher numbers indicate a more stimulating effect.

Linear harmonicity activates similar emotional systems to vertical harmonicity (Wieser and Mazzola 1986; Blood and Zatorre 2001; Brown et al 2004; Baumgartner et al 2006; Koelsch et al 2006).

B.2.6 Harmonicity and Valence

Both vertical and linear harmonicity are powerful indices of valence (Fritz 2009), or whether a sound is "positive" or "negative", "pleasing" or "not so pleasing". Linear harmonicity may track the evolution of valence indices over time—the principle is simply the more harmonic, the more positive valence, the less harmonic, the more negative valence.

It is conceivable that the Heschl's gyrus-related equations may be reconstituted with a different mathematical approach. It is highly unlikely that the planum temporale function could be approached in any different way.

B.3 Rhythmicity: Mirror Neurons, the Auditory and Pre-Motor Cortex

Human responses to musical rhythm involve a complex set of activations of mind and body systems (Osborne 1. 2009; Osborne 2. 2009; Osborne 3. 2012) including perceptual systems, the dorsal cochlear nucleus, inferior colliculus and spinal systems (Meloni and Davis 1998; Li et al 1998) the primary and secondary auditory cortices (Peretz and Kolinsky 1993; Penhune et al 1999), mirror neurons (Rizzolati et al 2001; Gallese 2003; Molnar-Szakacs and Overy 2006; Overy and Molnar-Szakacs 2009), pre-motor and motor cortices, basal ganglia, vestibular system and cerebellum (Zatorre and Peretz 2001; Peretz and Zatorre 2003; Turner and Ioannides 2009), the autonomic nervous system (Updike and Charles 1987; Iwanaga and Tsukamoto 1997; Byers and Smyth 1997; Cardigan et al 2001; Knight and Rickard 2001; Aragon et al 2002; Mok and Wong 2003; Lee et al 2003; Iwanaga et al 2005), and finally somatic and core emotional systems (Holstege et al 1996; Gerra et al 1998; Panksepp and Trevarthen 2009). Some of these may be related in particular to the firing of mirror neurons capable of regenerating perceived behaviours, vitality affect and energies encoded in the sound and its manner of performance in the mind and body of the listener. Fast rhythms of high energy activate arousal in both the Autonomic Nervous System and endocrine systems such as the HPA axis. Slow rhythms activate counterarousal.

X-System detects a basic, "default" rhythmic pulse in terms of beats per minute. There are often difficulties in establishing metre, but X System approximates the arousal effect of metrical structures by averaging the accumulation of power of rhythmic events over time. The power of a rhythmic event is defined as the ratio of the energy before the beat to the energy after it. In one very simple implementation, the beats per minute value (B) is combined with the mean of the beat strength (S) to produce a value for rhythmicity (R) where:

$$R = \sqrt{B} * S^2$$

Figure 27:
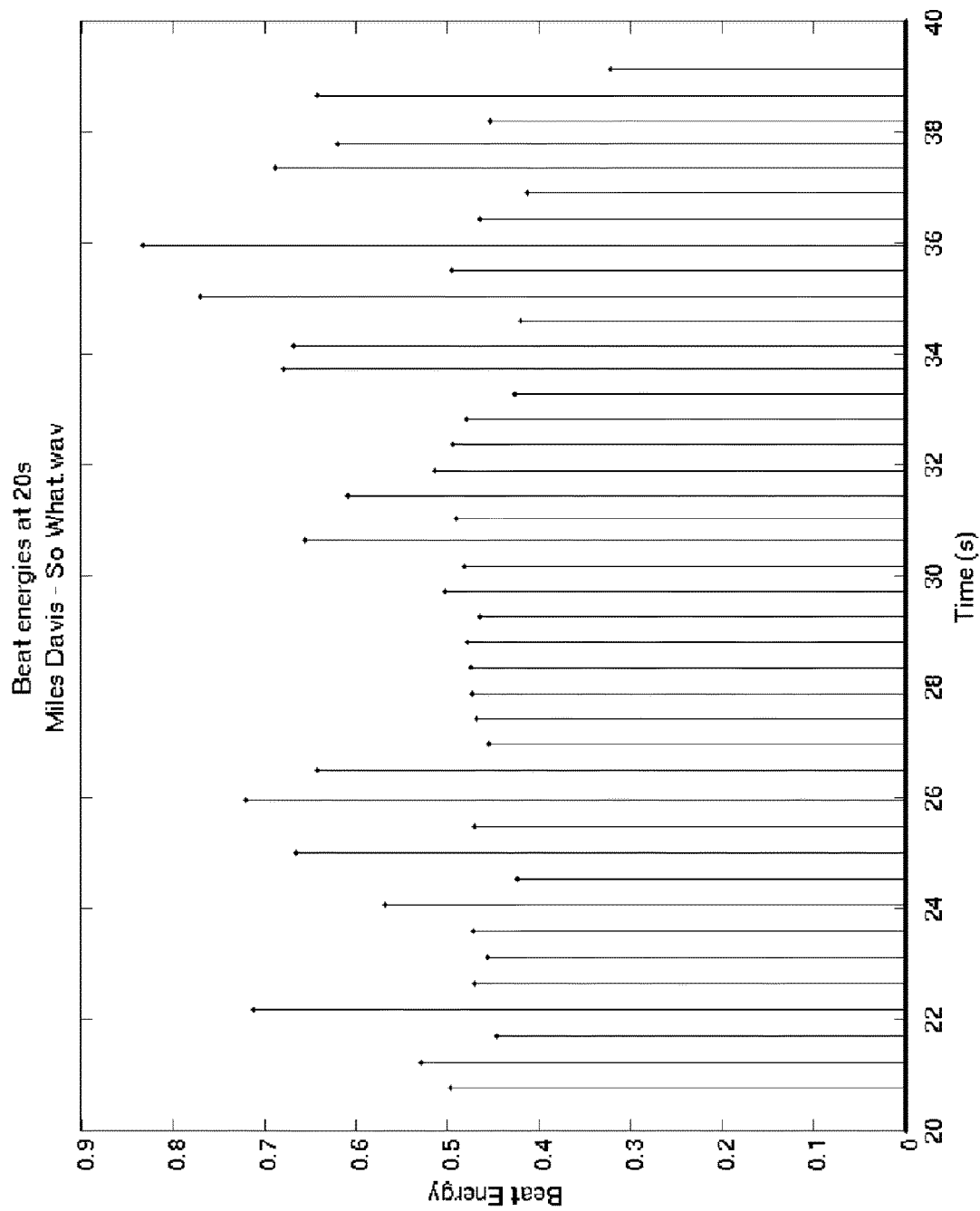
FIG. 27 shows Beat Energy as a function of time.

This equation is a non-limiting example of how rhythmicity can be calculated and other ways of linking R to B and S may well be appropriate; furthermore, R may be defined in terms of other or additional variables. R, in general, may be a function of B and S, but the optimal relationship will depend on various factors. See FIG. 27, showing beat energy as a function of time.

More details on Rhythmicity:

B.3.1 Cochlear Modelling

As explained earlier, aural perception of rhythm is predicted through conventional cochlear modelling: Following audio input, all subsequent analyses are performed on a transformed instance of the input sample data which accounts for certain aspects of the auditory pathway, primarily the Cochlea pick-up. The behaviour of the Cochlea is well understood and accurate models have been developed. We apply a frequency-dependent gain function to the input signal, which attenuates bass signals and amplifies treble components, with a filter "knee" at around 6 kHz. The exact transform used is the "A Weighting" as specified in IEC 61672.

B.3.2 Rhythmic Induction

The activations of primitive spinal pathways and the pre-motor loop (including basal ganglia, vestibular system, cerebellum etc.), all concerned with primal responses to rhythmic impulses, are predictively modelled by beat induction, using a specifically calibrated onset window.

Rhythmicity is, of course, a parameter that models the basic tempo of the sample, as well as higher order metrical structures within. It is computed by first determining note onsets, using spectral flux peak detection. These onsets are then used to generate and score a large number of metrical structure hypotheses. Candidate hypotheses are generated, filtered, and scored, using the methods of Dixon [Evaluation of the Audio Beat Tracking System BeatRoot, Journal of New Music Research, 36 (1), 39-50, 2007]. In addition to the methods described therein, we extend the process to include the magnitude of the spectral flux surrounding the onset event in order to estimate higher order structure. The hypotheses generated are filtered and scored using the same methods, with the final output comprising an estimate of the fundamental tempo of the sample, a secondary output in which the tempo is weighted according to the predicted metrical structure, in which the more distinct an accented beat is from the base beat, the higher this value. A confidence value is also expressed as the variance of the distribution of these outputs for all beat hypotheses scoring above a given threshold. This confidence value is normalised to permit comparison across samples.

B.3.3 Auto-Correlation

Rhythmic pattern recognition and retention (for example in the secondary auditory cortex of the temporal lobes) is predictively modelled by self-similarity/auto-correlation algorithms (e.g. Foote http://207.21.18.5/publications/FX-PAL-PR-99-093.pdf.)

First the audio is Hamming-windowed in overlapping steps; the log of the power spectrum for each window is calculated by means of DFTs (discreet Fourier transforms). these coefficients are perceptually weighted through Mel-scaling. Finally a second DFT is applied to create cepstral coefficients. High-order MFCCs (Mel-frequency cepstral coefficients) are discarded, leaving the 12 lower-order MFCCs, forming 13-dimensional feature vectors (12 plus energy) at a 100 Hz rate. These data are then subjected to vector autocorrelation, plotted in a two-dimensional window, where both x and y axes plot the unfolding of the track in time. Areas of "brightness", reading upwards, for example, from the first instant of the track on the x axis, indicate points of similarity, and likely metrical structures.

Density of distribution of points is also used in a predictive index of rhythm-induced arousal (the greater the density, the higher the arousal).

B.3.4 Power

Activation of mirror neuron systems, which detect, among other things, the power, trajectory and intentionality of "rhythmic" activity, is predictively modelled through indices of rhythmic power, including computation of volume levels, volume peak density, "troughs", or the absence of energy and dynamic profiles of performance energy.

B.3.5 Volume Envelope Analysis

The volume envelope is calculated as the RMS of 5 ms slices of the amplitude data.

B.3.6 Volume Level

This is simply the mean RMS level over the time period.

B.3.7 Volume Peak Density

Number of volume peaks per slice (usually 10 seconds), as found by the MATLAB findpeaks function with minpeakdistance=100 ms, multiplied by the mean height of the peaks above the volume mean, divided by the volume standard deviation.

B.3.8 Volume Differential Peak Density

As Volume Peak Density but taken on the first differential of the volume.

B.3.9 Volume Trough Length

The average durations for which the volume is lower than half a standard deviation below the volume mean.

B.3.10 Volume Trough Minima

The mean of the volume minima of volume troughs divided by the volume standard deviation.

B.3.11 Dynamic Profile

In addition, the profile of expenditure of energy (precipitous for high arousal, smooth for low) before and in between onsets, which appears to be important mirror neuron information, will in future be predicted by computation of profiles of energy flow leading to significant articulations.

For example, $\tau$ "tau" coupling (Lee 2005): $\tau_x = K x, g \tau_g$ where tau=time at origin of glide (end of previous onset), x=the gap preceding the next detectable onset, g=a patterned flow of electrical energy through an assembly of neurons, kappa=movement value determined by the brain. Profiles of energy will be determined by profiles of mean values of kappaXG.

B.3.12 Standard, commercially available software for rhythm detection may be used satisfactorily for some genres of music, but such software may fail to detect the specific bio-activating rhythm of any given piece of music and may even have difficulty in detecting rhythm at all in some. The above algorithms, which predictively model the activations of core rhythmic processing centres of the brain, have proved reliable. Some of these algorithms, for example beat detection, could in theory be replaced by other mathematical procedures. The originality of the invention lies in the unprecedented nature of the biological modelling. Thus we have a phenomenon in music (rhythm) that is known to have an effect on arousal and counter-arousal in the autonomic nervous system (as well as core emotional systems, endocrine activity and neurotransmission), which in turn is known to have a powerful influence on how you feel: relaxed, able to concentrate, wanting to dance etc. We also have a means of measuring the effect of the rhythm (our sensor). Our categorisation algorithms (above) take as an input the relevant data from the digital signature analysis and yield as an output a predicted impact on the chosen biometrics. Intense rhythms will have an arousing effect while gentle rhythms will have a calming effect, and there is no shortage of prior art based on the same principle. In modelling the innate neurophysiological response to rhythm an algorithm linking this measurement of rhythm to its expected effect on (in this embodiment) heart rate and galvanic skin conductance is hypothesised, tested and refined.

B.4 Turbulence and Core Emotional Systems (Locations and Organs)

The 'turbulence' of a piece of music relates to the speed and extent to which it changes over a period of time, in terms of rhythmicity and harmonicity as well in terms of general fluctuations in sound pressure.

'Turbulence' combines indices of change in rhythmicity and harmonicity, related to pathways described above, with auditory brainstem and cortical activity innervating the amygdala, hippocampus and core emotional regions affecting neurotransmission and endocrine systems, including the HPA axis, dopamine circuits and levels of, for example, norepinephrine, melatonin and oxytocin (Miluk-Kolasa et al 1995; Gerra et al 1998; Kumar et al 1999; Evers and Suhr 2000; Schneider et al 2001; Blood and Zatorre 2001; Grape et al 2003; Uedo et al 2004; Stefano et al 2004; Herbert et al 2005; Nilsson et al 2005). This important predictor of arousal and counterarousal may be represented as the differential of rhythmicity and harmonicity.

'Turbulence' is therefore a measure of rate of change and extent of change in musical experience. These factors seem to activate core emotional systems of the brain, such as the amygdala and periaqueductal grey, which are in turn linked to autonomic and endocrine systems. At high levels of musical energy turbulence may enhance arousal; at low levels it may add to the counterarousal effect.

The total turbulence (T) of a piece is determined as a combination of the turbulence of the harmonicity (H') of the piece and the energy present during peaks of volume of the track (P). Turbulence of harmonicity is calculated as the standard deviation of the differential of the harmonicity, divided by the mean of the differential.

In one very simple implementation, total turbulence is calculated as:

$$T = dH/dt * P$$

This equation is a non-limiting example of how turbulence can be calculated and other ways of linking T to H and P may well be appropriate; furthermore, T may be defined in terms of other or additional variables.

Figure 30:
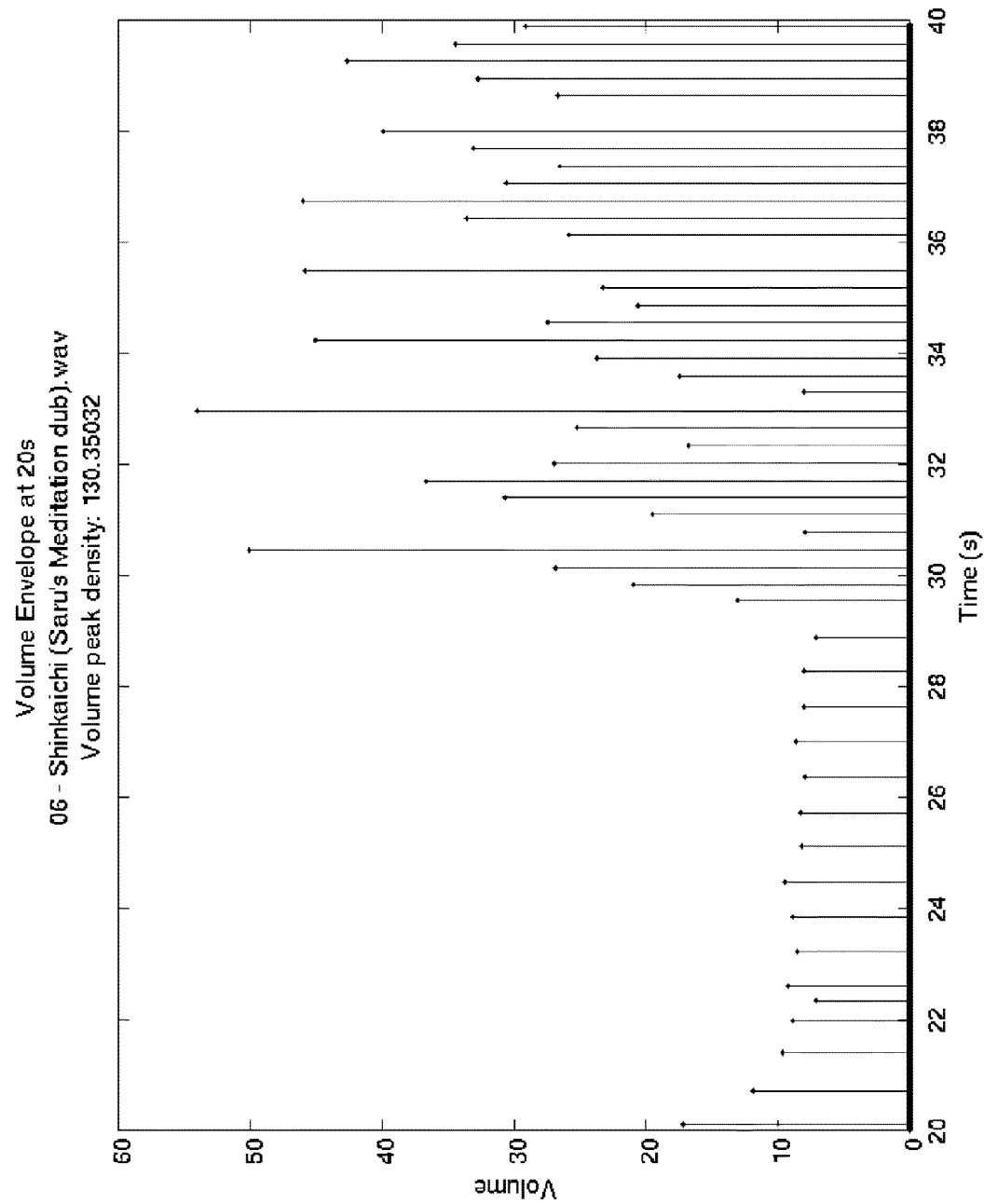
FIG. 30 shows Volume as a function of time.
Figure 31:
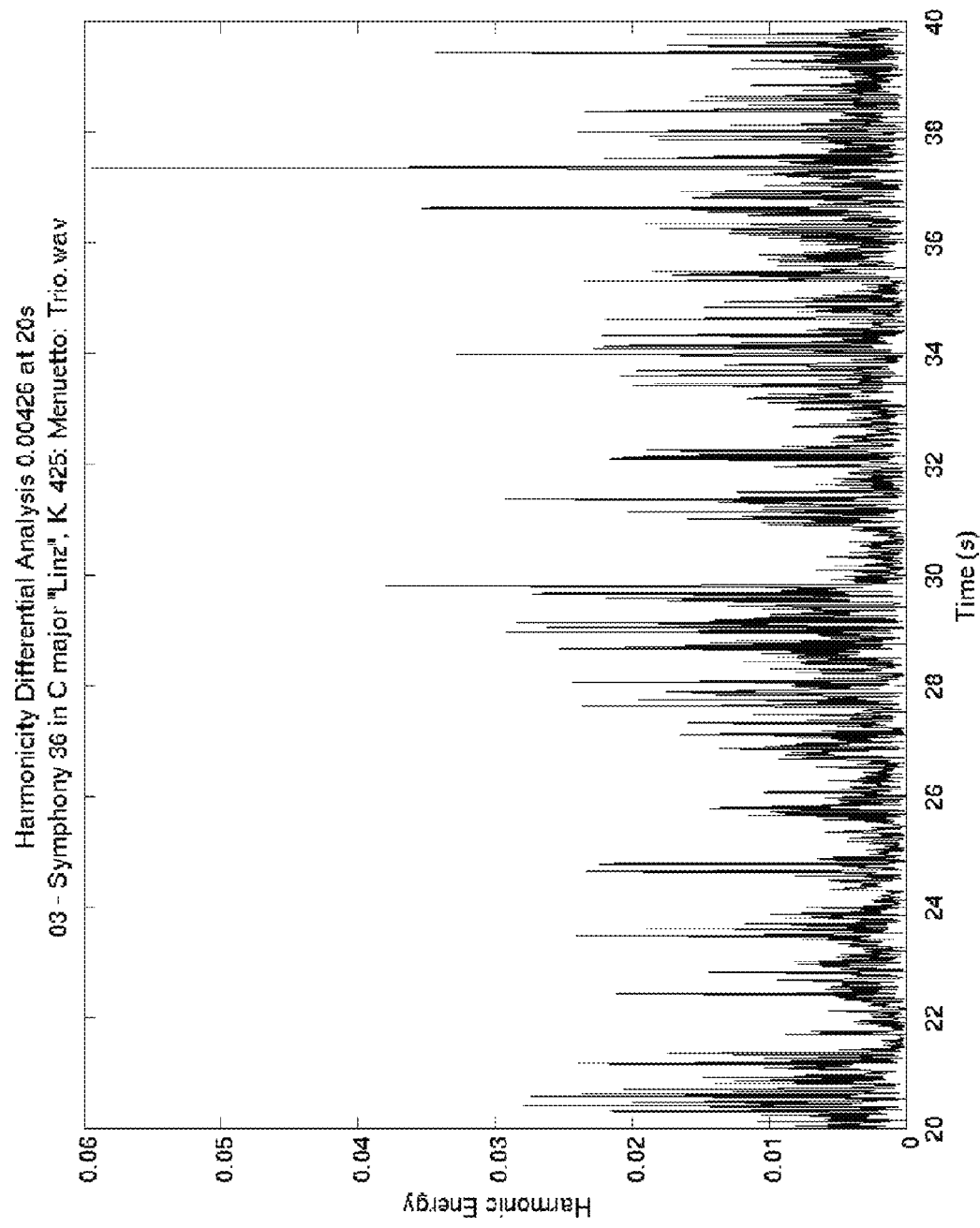
FIG. 31 shows Harmonic Energy as a function of time.

See FIGS. 30 and 31, showing volume and harmonic energy as a function of time.

B.5 Combining Values

Each of the algorithms described above, hypothesised and refined through testing, has effectively become a 'virtual organ' of the brain that helps us predict the effect on levels of arousal and counter-arousal of patterns that can be detected in music using digital signature analysis. The relative weighting of each 'organ' may be adapted using heuristic, machine learning or other techniques to calibrate the overall predictive power of the set of 'virtual organs' working in harmony.

Any subset of the above analyses may be combined together to produce a single number estimating where a piece of music (or part thereof) lies on the scale from relaxing to exciting. The formula used to perform this combination may be derived from experimental data, as follows: A number of human listeners listen to the same selection of tracks. Each listener then independently ranks all the tracks in order from what they consider the most relaxing to the most exciting. (The ranking could also be done objectively by measuring the listeners' physiological data, but this has so far given much less consistent results across listeners.) A statistical regression analysis is then carried out, with the average human ranking as the dependent variable, and the chosen subset of musical analyses as the independent variables. In other words, a single formula is produced which uses the analyses to predict the human rankings. The coefficients in this formula are chosen to give the best possible prediction, considered over all tracks. The resulting formula may then be used to produce automated predictions on a mass scale for a much larger number of tracks. Consider the following example data:

| Track | Average human ranking (0-1) | Mean harmonicity (mh) | Volume level (vol) | Rhythmicity (rhy) |
|---|---|---|---|---|
| 1 | 0.2 | 0.212 | 0.010 | 118 |
| 2 | 0.4 | 0.231 | 0.069 | 228 |
| 3 | 0.5 | 0.204 | 0.123 | 187 |
| 4 | 0.6 | 0.225 | 0.294 | 130 |
| 5 | 0.8 | 0.173 | 0.163 | 155 |

Any statistical regression method may be used to produce the overall formula. For example, if we use multiple linear regression with the ordinary least squares estimator, we obtain the following:

Predicted ranking=−6.59*mh+1.63*vol+0.0018*rhy+1.36

Non-linear transformations of one variable (e.g. logarithm or reciprocal) or non-linear combinations of multiple variables (e.g. their product or ratio) may also be used, by pre-calculating them and then treating them as additional variables in the regression.

The coefficients employed in each of the algorithms, and the relative weighting of the algorithms in combination, may be optimised for different musical styles using metadata (such as genre and artist) that are typically carried alongside music distributed in digitised formats such as the Compact Disc and over the Internet. With the accumulation of large amounts of (anonymised) human response data that may be fed back (with the consent of the listener) in networked deployments of X-System it will be possible to fine-tune the relative weighting of both the equation coefficients and their relative weighting in combination to improve accuracy. Similar optimisation of coefficients and weightings will be achieved by analysing user data in combination with the music metadata (such as genre and artist) that are typically available with music distributed in digital formats, and in due course this optimisation will be extended to both the individual user and specific recordings.

The overall arousal index calculated for each piece of music may be expressed either as a single number that describes the overall neurophysiological effect of listening to it from start to finish, or it can be displayed graphically with arousal index on the vertical axis and time on the horizontal axis. The resulting trace would effectively describe the neurophysiological journey a listener may expect as they listen from beginning to end. This latter is likely to be of particular use in longer and more complex pieces of music such as much of the classical repertoire, whereas some other repertoire such as modern Western pop music might more conveniently be represented by a single number. In either case, the effect of a piece of music is both inherent (in that it is a product of the patterns detected in the music) and dependent on the state of the listener (in that the neurophysiological effect of music is relative rather than absolute [Altshuler 'The Iso-Moodic Principle' 1948]).

As we learn to navigate the brain in greater depth and detail, and as sensor technology develops further, different equations will be developed to predict the effect of different musical structures on different measurable outputs. All these instances of the application of the Innate Neurophysiological Response to Music are intended as different implementations of the present invention, which claims a novel system and method of predicting the effect on universal human neuro-physiology of any piece of music from any musical tradition by means of analysing bio-activating patterns in music and using mathematical equations tailored to specific biometric indices to predict the effect of these musical patterns on the chosen biometric indices.

B.6 This section describes an alternative approach to combining values for rhythmicity, inharmonicity and turbulence to produce an excitement (E). In this alternative approach, E is given by:

$$E = (10 * I * R) + T$$

This equation is a non-limiting example of how excitement E can be calculated and other ways of linking E to I, R and T may well be appropriate; furthermore, E may be defined in terms of other or additional variables.

This generally produces a number from between −1 and 7, representing the range of the counterarousal-arousal scale. Currently the thresholds for five arousal categories are approximated as −1 to 0.6=1
0.6 to 2.2=2
2.2 to 3.8=3
3.8 to 5.4=4
5.4 to 7=5

An alternative is an equation where rhythmicity and harmonicity are multiplied and turbulence added. In other examples, log scales and Fibonacci progressions may be used in the analysis of auditory data.

More detail: For each of R, H and T, X-System records both a single average value (μR, μH, μT) and a profile of variation further categorized as ascending, descending or stable (ΔR>0, ΔR<0, ΔR=0; ΔH>0, ΔH<0, ΔH=0; ΔT>0, ΔT<0, ΔT=0).

The average values of R, H and T are mapped (in the simplest case the normalised mean is taken) to an n dimensional point p characterising physiological state. The variations of R, H and T are also mapped (again, in the simplest case the normalised mean is taken) to another n dimensional point q characterising the directional effect these values will have on the physiological state.

The concatenation of p and q allows each musical excerpt to be mapped onto a Musical Effect Matrix M, a 2*n dimensional matrix, n dimensions corresponding to the physiological parameters measured by E representing granular ranges into which E can fall, the other n dimensions corresponding to the effect the track will have on the physiological parameters (ascending, descending or maintaining any given physiological parameter or dimension of E).

We now describe in more detail how the Music Effect Matrix M is generated. As noted earlier, FIG. 23A is a block diagram showing the major components in X-System for analysing harmonicity and FIG. 23B is a block diagram representation of all of the major components of the musical analysis tool. The values output by the analysis are specified as functions in t, the time index of a particular measurement. These values (corresponding to R, H and T) are grouped as follows:

X(t): values for rhythmic "presence", tempo, power and density of pulse-related rhythmic structures, and harmonic rhythm-related to cerebral cortex activity, core emotional locations, and autonomic and endocrine responses.

Y(t): degree of conformity, within the limits of human perception, to exponential series-related frequency structures in melody and harmony-related to the cochlea, Heschl's gyms and cerebral cortex processing, core emotional locations and autonomic and endocrine responses.

Z(t): the rate and magnitude of variation in X(t), Y(t) and dynamic power (W(t)) which is measured using the normalized, gain adjusted volume level-related to activation of core emotional systems, and the endocrine and autonomic nervous systems.

Categorization may be preceded by aggregation, documenting provenance, genre and other data for music tracks. This may be according to an industry standard such as that provided by Gracenote®, it may be the result of individual user editorial, crowd-sourcing methods such as collaborative filtering, or may be the result of future aggregation standards based on, for example, digital signature analysis. The purpose of aggregation is to allow the user to choose a preferred musical style, though it is not strictly necessary for the proper functioning of X-System.

In order to reduce the computational cost of analysing a piece of music, only certain regions are examined. The location and length of these regions are determined dynamically, based on configurable parameters and an adaptive mechanism that recursively examines regions with a large rate of change. This produces a sparse array of values for each function, identified by a time index. Due to the recursive analysis, the step size_t will vary over the function domain t.

Algorithmically, these regions are generated by applying a windowing function to the incoming audio data. The sampling window is then "stepped" over the region, and the results of each step are aggregated to form the single output at time t. For example, a region may consist of the (absolute) time interval (0 s; 1 s), which is further windowed into 50 ms samples, with a 10 ms step size. This produces a total of 96 sample points, which are combined to form a single value X(0)=x.

The analysis of X(t) is performed by an "acoustic streaming"-based rhythmic induction, combined with pattern-recognition and an index of power and density.

Rhythmic induction is performed using two main techniques; band-limited power spectral density onset analysis, and adaptive comb filtering. The results of both techniques are then subjected to a number of heuristics based on music theory, and are combined to form a single estimate of the musical rhythm.

Heuristics include rules such as the minimum and maximum plausible tempos or some form of probability distribution of likely tempos for a given input genre if known. They may also include emphasis and de-emphasis of certain frequency bands based on the input.

Spectral Density Onset Analysis uses a sequence of short-time Fourier transforms of the windowed samples to calculate the energy present in specific frequency bands. This data is tracked temporally to observe peaks in bands, which characterise rhythmic events.

Comb Filtering involves convolution of the input signal with a variety of impulse trains of different spacing, on the basis that as the impulse spacing approximates the rhythm of the input, the overall convolution result will increase. This technique can then be used recursively to _find a best-fit impulse spacing which characterises the input rhythm.

Values for Y(t) are established by means of an adaptation of auditory scene analysis. The audio input data are passed through a gammatone cochlear filter bank, splitting them into multiple streams. For each stream, special, frequency and onset information is calculated.

Spatial information is acquired from stereo tracks of each stream, frequency peaks are calculated using a Fourier transform and onset detector maps are applied to find the starts of sound elements.

This information is combined and correlated to partition the audio data input into sound sources. For each of these sound sources a number is calculated as the ratio of sound energy within the harmonics of its fundamental frequency to the sound energy outside the harmonics of its fundamental frequency. Y(t) is the mean value of the ratios for each sound source from the excerpt.

The fundamental frequency is determined using a Harmonic Product Spectrum, in which the signal is repeatedly multiplied with down-sampled copies of itself, causing a large peak to occur in the frequency spectrum corresponding to the fundamental frequency. Standard signal-processing techniques are also applied to de-noise the resultant output.

Z(t) is measured as the rate and magnitude of variation in X(t), Y(t) and W(t).

In each of these cases (X(t), Y (t) and Z(t)) the system records both a single average value (μX, μY, μZ) and a profile of variation further categorized as ascending, descending or stable:

Ascending—An overall positive trend in the functions X(t), Y (t) and Z(t).

Descending—An overall negative trend in the functions X(t), Y (t) and Z(t).

Stable—Only minor deviations from the mean μ result over the audio input signal.

The average values of X, Y and Z are mapped (in the simplest case the normalized mean is taken) to an n dimensional point p characterizing physiological state. The variations of X, Y and Z are also mapped (again, in the simplest case the normalized mean is taken) to another n dimensional point q characterizing the directional effect these values will have on the physiological state.

The concatenation of p and q allows each musical excerpt to be mapped onto the Musical Effect Matrix M, a 2n-dimensional matrix, n dimensions corresponding to the physiological parameters measured by E representing granular ranges into which E can fall, the other n dimensions corresponding to the effect the track will have on the physiological parameters (ascending, descending or maintaining any given physiological parameter or dimension of E).

C. How X-System is Used

As noted above, X-System may use a subject's biometric data (where a sensor is available) to measure neuro-physiological arousal. It then leads the subject by stages towards a target level of such arousal, state of mind and/or affect. This is achieved with a database of music, previously categorised using predictive modelling of innate neuro-physiological responses. Categorisation in real-time or near real-time is also possible. Categorisation can be visually displayed (e.g. on the display of the computing device used for music playback); this can include a display of the E values for each music track, or how the E (Excitement) value changes during a track; R, I, H, C and T parameters can also be visually displayed. A piece of music that predicts or matches the subject's current level of neuro-physiological arousal is selected and a playlist constructed on the basis of the fundamental musical effect of each constituent piece of music. Listening to the playlist directs or moves the user towards the desired level of arousal, state of mind and/or affect by unconscious neuro-physiological entrainment with the music and enables that level to be maintained. The subject's current level of neuro-physiological arousal can also be visually represented, as can the convergence to the desired target state.

Figure 18:
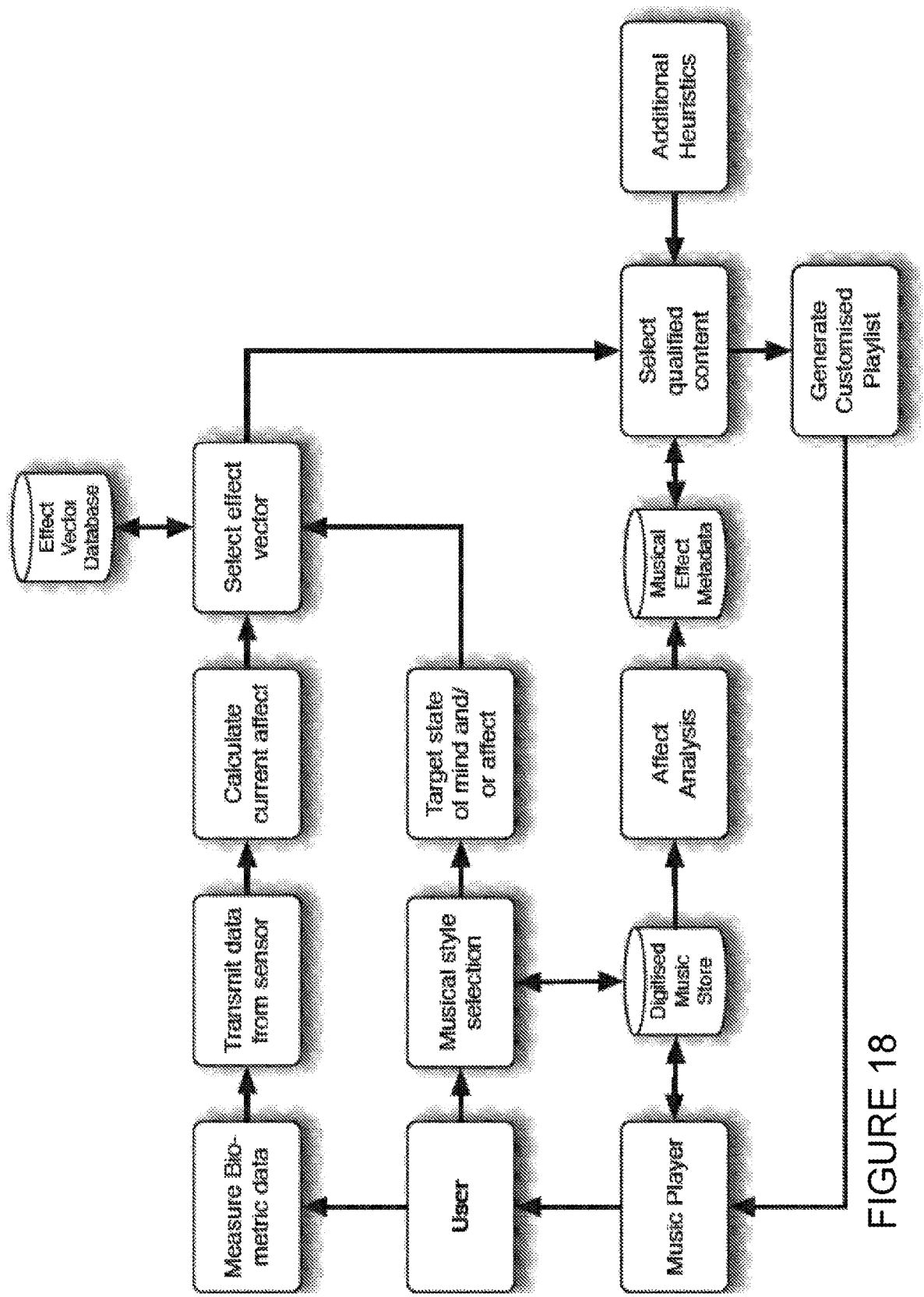
FIG. 18 shows an overall system construction where the user of the system both selects their desired affect goal and is the recipient of the generated output.
Figure 19:
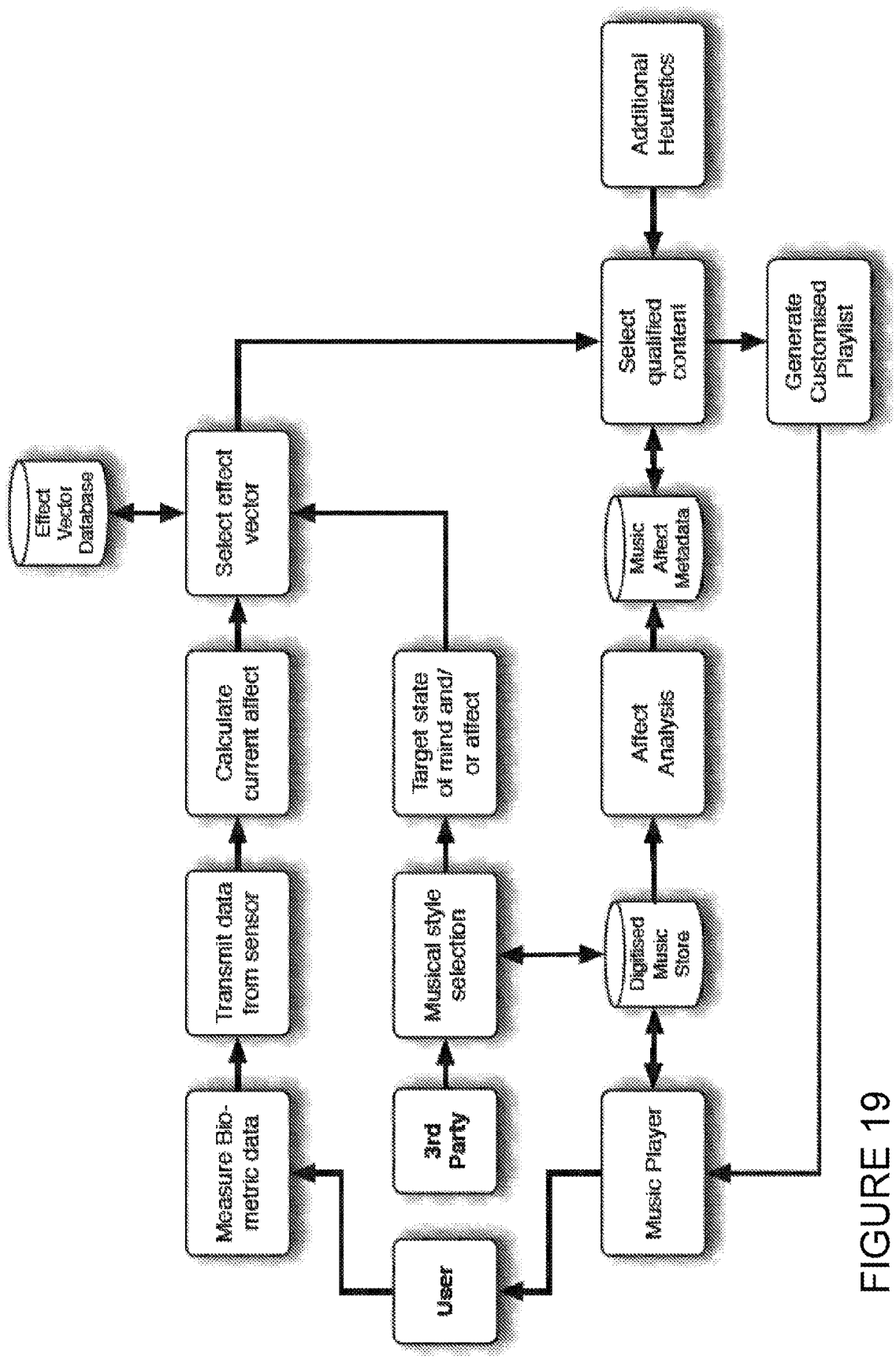
FIG. 19 shows an overall system construction where selection of target affect is made by a party external to the user of the system.
Figure 25:
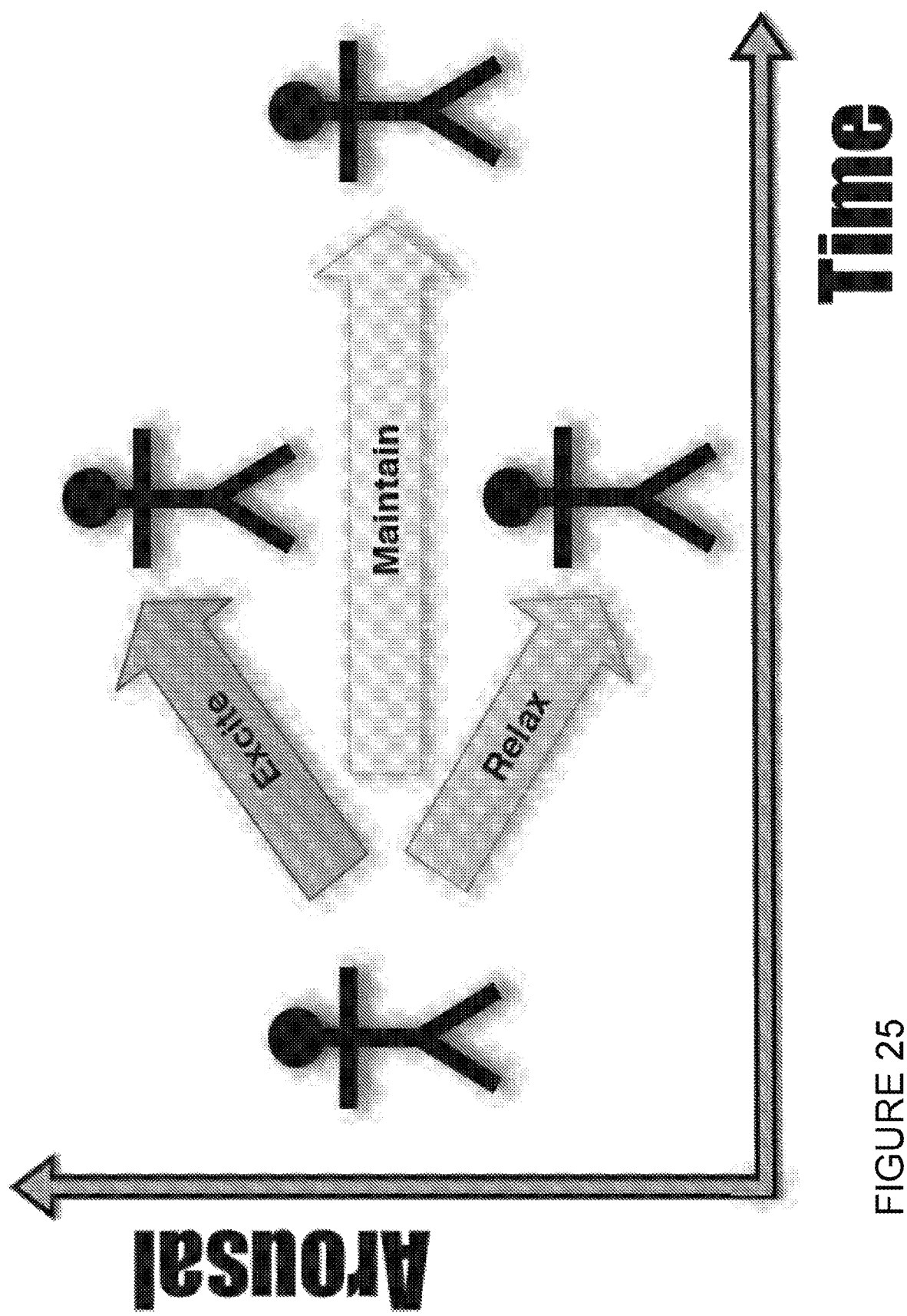
FIG. 25 shows schematically arousal as a function of time, for Excite, Maintain or Relax pathways.

X-System is, in one implementation, designed to sense the state of mind and body of the user and stream music of selected repertoires to achieve target states such as:
Excitement
Relaxation
Concentration
Alertness
Potentiation of physical activity
See FIGS. 18, 19 and 25, for example.

C.1 Components in the X-System

X-System includes:
automatic categorisation software capable of categorising music of all cultures either remotely or in proximity according to specific levels of arousal and counter-arousal; these categorisations may be offered for general use independently of the sensors and diagnostic software. This may be based on Nigel Osborne's INRM (Innate Neuro-physiological Response to Music) paradigm.
a database of music categorised manually or automatically (using the automatic categorisation software) to achieve specific levels of arousal and counterarousal
sensors to detect physiological indicators of arousal (such as excitement) and counterarousal (such as drowsiness), including heart rate and galvanic skin conductance
diagnostic software which employs sensor data to monitor levels of arousal and counterarousal in the user
music playback/streaming (eg. playlist selection) software which selects previously categorised music from a database to stream appropriate repertoire to achieve target states of mind and body by a process of step-by-step entrainment, starting from the current diagnosed "state"; progress towards these goals is monitored by the diagnostic software. Specific tracks for a listener may be selected for playback (by streaming or otherwise) according to bio-feedback from that listener; the playlist may be created locally and the music tracks requested for streaming/download etc; it is possible also for the bio-feedback and desired "state" information to be sent to a remote music server and for that server to generate the appropriate playlist and provide music tracks to the local, personal playback device. In this variant, the personal playback device need have no local music library or X-System software/firmware etc.; it needs only the ability to detect the listener's audio preferences and bio-feedback data and to relay that back to the remote server using a low capacity back-channel and to then receive the music from the remote music server.

Note that all software may also be implemented in hardware, firmware, SoC, as part of a third party audio stack and in any other convenient manner.

Appendix 1 is a more detailed description of the components of X-System.

C.2 Practical Applications of X-System

The sensor is intended to measure one or more predetermined parameters of the user's state of mind and body and to communicate this information to a processor; the processor is designed to select tracks from the music categorisation data appropriate to lead the user from her/his current state of mind and body to the intended condition of arousal or counter-arousal. This combination will allow X-System to:
Sense, in real time, the neuro-physiological state of the human mind and body;
Analyse the music collection of the consumer, or any other collection he/she has access to, such as with a cloud-based or remote/central server based music service; and
Calculate and deliver play lists as a function of a desired state of arousal.

This will enable users to direct themselves to a desired state, such as:
Excited and ready to play sports or exercise; for example, to enhance oxygenation levels for competition or reduce post-surgical recovery times;
Relaxed and able to drift off to sleep;
In a meditative state to support development of insight;
In a meditative state to support the development of creative thought; and
Maintaining focus and able to concentrate.

(for example, to provide support to overcome conditions such as insomnia, to reduce medication in post-traumatic stress disorder (PTSD) and in mania patients, to develop and to organise memory, categorised by short, medium and long term need for data retention), and to create a state in which to encourage creativity and imagination.

Figure 20:
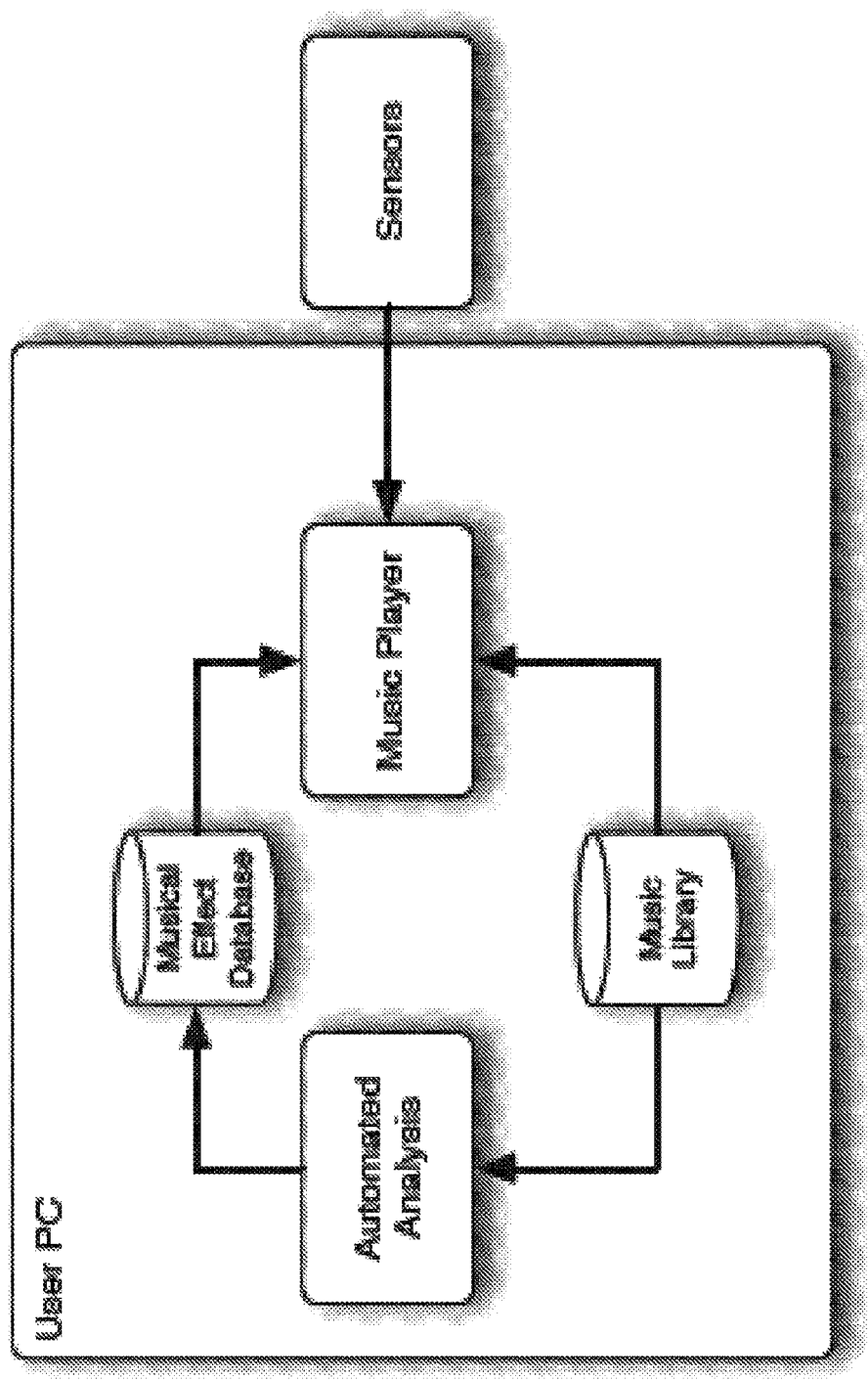
FIG. 20 shows an implementation of the X-System invention where all aspects of the software reside on the users PC (the term 'PC' should be construed expansively to cover any computing device of any form factor, including any device capable of performing computing functions).

The diagram of FIG. 20 illustrates the current project implementation of X-System. In an alternative to the implementation of FIG. 20, because ubiquitous mobile computing blurs the distinction between devices, the elements shown in FIG. 20 within a User PC (music player, music library, automated analysis and musical effect database) may be distributed over two or more computing devices. In a commercial example it may also be configured to work with portable audio devices: see FIG. 21.

While these components are key elements of X-System, its core innovative technology is a definition of the bio-active components of music (based on a predictive Innate Neuro-physiological Response to Music paradigm, Osborne 2009, eg. see FIG. 17), the algorithms used to calculate them based on digital signature analysis and the calibration methods used to tune the system to the neuro-physiological response of an individual.

D. The Sensor or Sensors

The sensor may be in the form of a wristband, a hand-held or any other device suitable for taking the required parameter measurements. The sensor may be body-mounted, or use ear buds (e.g. combining a sensor into ear-bud headphones), remote monitoring via IR or acoustic, wireless, or more generally any form of life sensing. The data captured preferably comprises biometric parameters such as heart rate (including pulse rhythm analysis), blood pressure, adrenaline and oxytocin levels, muscular tension, brain waves and galvanic skin conductivity. Alternative equipment formats include necklaces, bracelets, sensors embedded in clothing, other jewelry, sensors implanted under skin, headsets, earphones, sensors in handheld form such as covers for 'phones, MP3 players, or other mobile computing devices.

Sensors currently used in the X-System project comprise a wristband sensor which will be used to measure galvanic skin response (GSR), and a standard finger clip Pulse Oximeter for the measurement of heart-rate and blood oxygenation. For the purposes of commercialisation these sensors will be combined in a single, wearable, wireless device. Other potential bio-sensors and motion sensors may be included as they become economically viable.

The sensors must be able to measure a combination of pulse rate and skin conductivity, combined with any other possible measurements and must be resistant to disruption from movements of the user or changes in environment; it must also be possible to wear the sensor for extended periods of time without discomfort or embarrassment. Other sensors include physical bio-sensors such as oxygenation, EDA, EDC, EDR, ECG, sugar levels, BPM, EEG etc, and multi-spectrum sensors (radio, IR, UV, heat, and broad spectrum), which detect bodily radiation auras.

Figure 21:
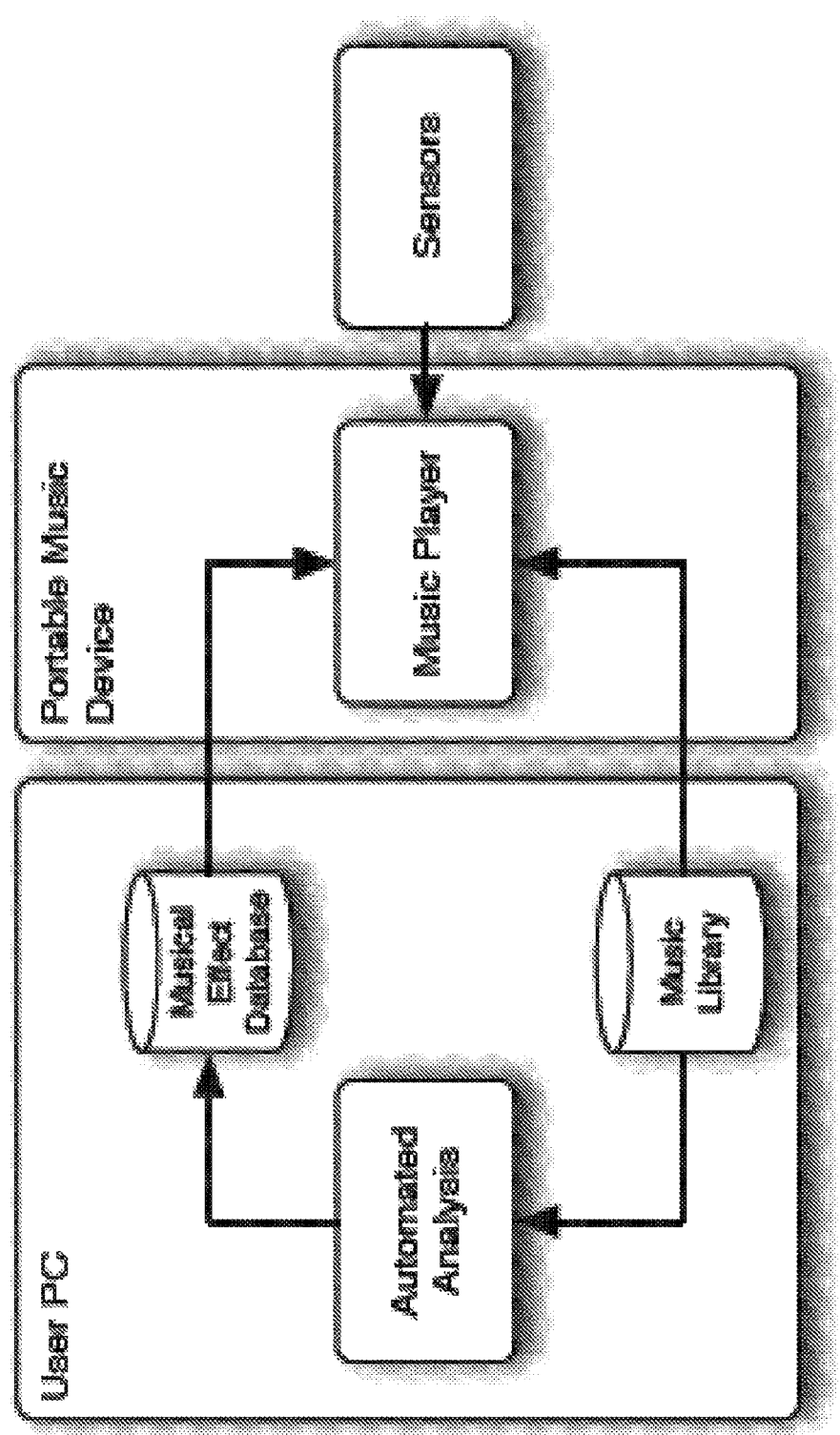
FIG. 21 shows an implementation of the X-System invention where a primary music library, and analysis software resides on a user PC, with the ability to transfer a selection of music to a personal music player device, which then generates a dynamic playlist based on the available music.
Figure 22:
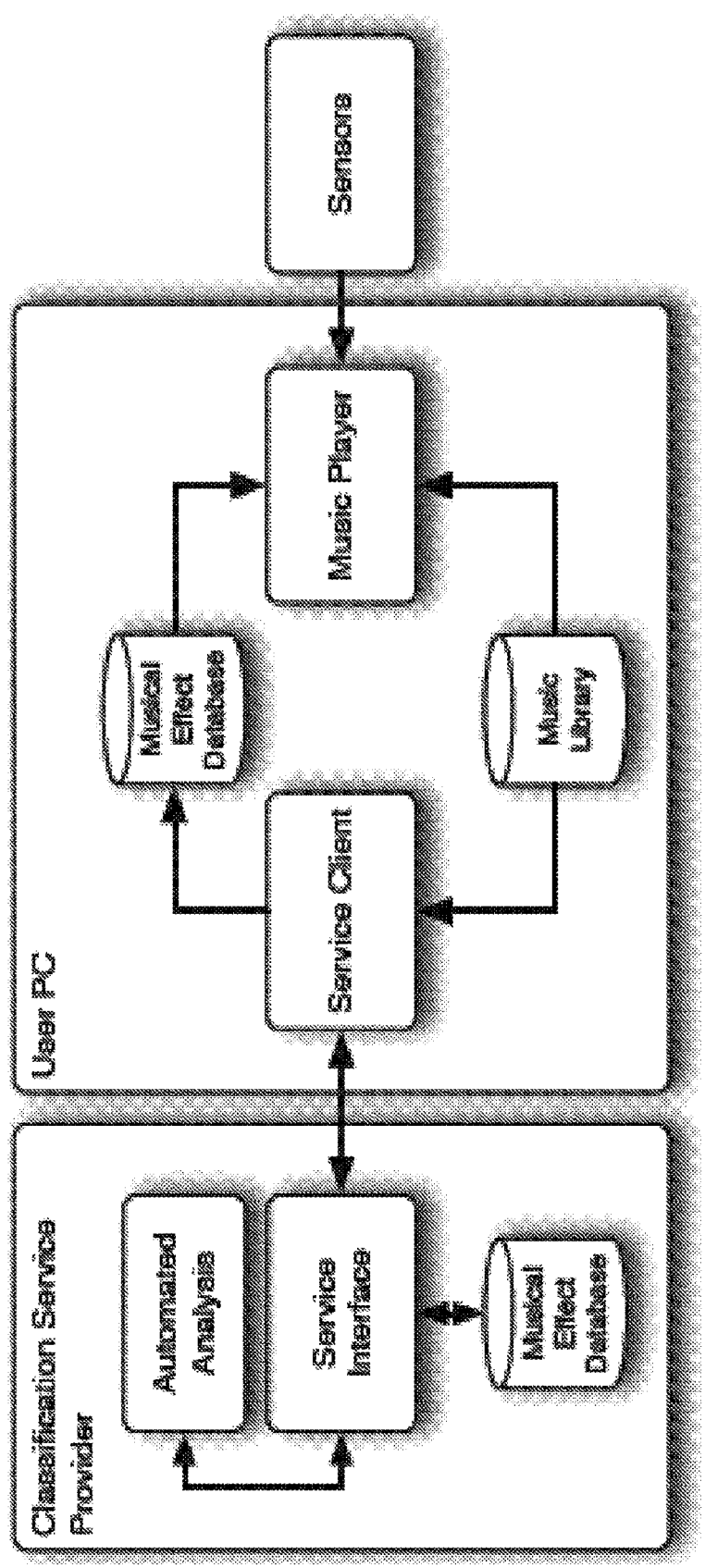
FIG. 22 shows an implementation of the X-System invention where an external service provider offers an analysis tool via a network connection. Audio may reside on either the user's PC or be "streamed" by the service provider, and a database of stored musical affect may be used to minimise track analysis.

FIG. 21 shows a desired architecture overview. FIG. 21 shows an implementation of the X-System invention where a primary music library, and analysis software resides on a user PC that is operable, remotely or locally by the listener or a third party, with the ability to transfer a selection of music to a personal music player device, which then generates a dynamic playlist based on the available music.

The X-System sensor measures certain chosen parameters of the user's physiological state and transmits the resulting data wirelessly to a processor in (or in communication with) a playlist calculator, which resides on or is otherwise connected to a music playback device (for example, a personal computer, smartphone, MP3 player or other audio device). Transmission is preferably wireless but it will be appreciated that other transmission types are possible. Indeed, the processor may be integrated with the sensor. The chosen physiological state parameters are denoted by P. A function F(P) reduces these parameters to a single, normalised point E, characterising the general physiological state of the user. In the simplest case E is a one-dimensional measurement of the user's physiological arousal (or counter-arousal). With further inputs a more complex measurement may be obtained, resulting in a point E of n dimensions. An effective prototype has been developed using pulse rate 'p' and galvanic skin conductivity 'v' to calculate a simple index of physiological arousal where $E=p+v$. Currently the prototypes use the Nonin X Pod Pulse Oximeter and a skin conductance biosensor. The pulse rate, oxygenation and skin conductance of the user are constantly monitored; heart rate may be used as to control mean variations in conductance. Both sensors currently work independently and are connected wirelessly to a controlling computer. They may be replaced with a single integrated sensor. Alternatively, any other form of wired or wireless communication of sensor outputs to player to output device is possible. Appendix 1 gives more details.

A user initially provides the system with their personal music collection (or uses an online library of streamable or downloadable music). This is analysed for level of excitement, using INRM categorisation in combination with signal processing and machine learning techniques. The user then synchronises this information with their music player and selects a level of excitement/arousal; someone other than the user may also select the excitement level. The sensor wristband provides the system with a constantly updating real-time state of excitement of the user, allowing the system to react to external effects on the user and "catch" them, using the principles of entrainment to bring them back towards the desired state. Once the user has achieved the target level of excitement, they are kept there by music determined to be effective at maintaining that state.

Although the current version of X-System's sensor is based on heart rate and skin conductance, there are strong arguments for early integration of other measures, including for example EEG, brainwave sensors. This would allow factors such as concentration, alertness, contemplation, drowsiness or creative flow to be monitored directly through sensing of frequencies of entrained firing of neurons in the brain, rather than indirectly through indicators of arousal. A second set of related challenges lies in further aspects of machine learning. Individual physiological responses vary considerably, from person to person, according to time of day, state of metabolism etc. X-System may learn from individual users the range of their physiological responses in order to identify relative levels of arousal, and individually calibrate the diagnostic software. It may also learn about their personal preferences as already articulated through their choice of repertoire. X-System may also go directly from a set of musical features, using a neural network to predict the effect of these on physiological measurements, without first reducing the features to an expected excitement/arousal level.

E. Musical Selection Algorithms

Certain levels of neuro-physiological arousal are necessary precursors of activities such as sleep, relaxation, accelerated learning and study, or increased alertness and activity. The user will preferably be presented with a user interface and choose from a menu of such activities in order for the system to establish a target level of arousal and affect that will facilitate the chosen activity.

The point E, representing the neuro-physiological state of the subject diagnosed by the sensor, is used to select music from a database of music tracks indexed by the Musical Effect Matrix M, based on a combination of the granular point r and a direction d pointing towards the physiological state towards which the user has elected to move (see preceding Section E for more detail).

The first piece of music selected will correspond to the initial neuro-physiological state of the subject, represented by E. Subsequent pieces are selected based on their values in M such that each would, played in order, be capable of progressively leading the subject's state towards the target state. The order in which the pieces of music are eligible to be included in a playlist is determined by a vector that represents a temporally-organised ascending, or descending as appropriate, series of musical effect values in M. The set of pieces of music in the database that meet the requirements of this series of effect values is known as 'Qualified Content'.

The Qualified Content is arranged into an actual playlist according to a set of rules, including but not limited to random selection, anti-repetition, genre preference or some other heuristic. In some cases it may be appropriate to comply with the US Digital Millennium Copyright Act (DMCA).

Where a sensor is used, then a biofeedback loop is established in order to ensure continual recalculation of the playlist to compensate for distraction, individual sensitivity and other factors based upon any dimensions of overall affect that are susceptible to continual measurement. Direction towards non-measured parameters of state of mind and/or affect will still occur despite the lack of a biofeedback loop because neuro-physiological arousal is a necessary precursor to state of mind and affect and establishes the conditions under which the listener is most susceptible to these other aspects of overall musical effect.

Once a piece of music has been played it is preferably removed from the list of potentially available content for a minimum number of cycles in order to avoid unnecessary repetition. This anti-repetition rule is subject to a feasibility test in order that a message of appropriate severity may be displayed to the user warning of insufficient content or variety of content in the music database to enable effective functioning of the system along with a suggested remedy such as a recommendation of further pieces of music which might be added to the database to improve its functioning.

In the case where content has been distributed pre-categorised or where it is streamed from a central server, playlists may be calculated initially in a dynamic mode where shorter excerpts are taken from the database. Once the listener has achieved the target level of arousal, longer excerpts are admitted into the qualified content pool for the purpose of playlist calculation and the system may enter maintenance mode. Any disturbance which causes the listener's level of arousal to vary by more than a predetermined factor may cause the system to re-enter dynamic mode and re-calculate the playlist based upon shorter excerpts in order to entrain the listener back to the target condition at an accelerated rate.

The anti-repetition rule as applied to shorter excerpts may be used to calculate the minimum required catalogue size on the basis of the number of separate musical styles that may be selected by the user, the average length of a shorter excerpt, the minimum number of cycles that must pass before the anti-repetition rule will admit a song or excerpt back into the selection pool and the number of shorter excerpts available that fall within the least-populated cell of the musical effect matrix.

F. The Music Player

The music player may be an adaptation of standard industry software such as the Windows Media Player which is capable of building dynamic playlists according to the Musical Selection Algorithms and of offering the user additional utility such as selection of musical style, display of associated metadata and video content.

Figure 24:
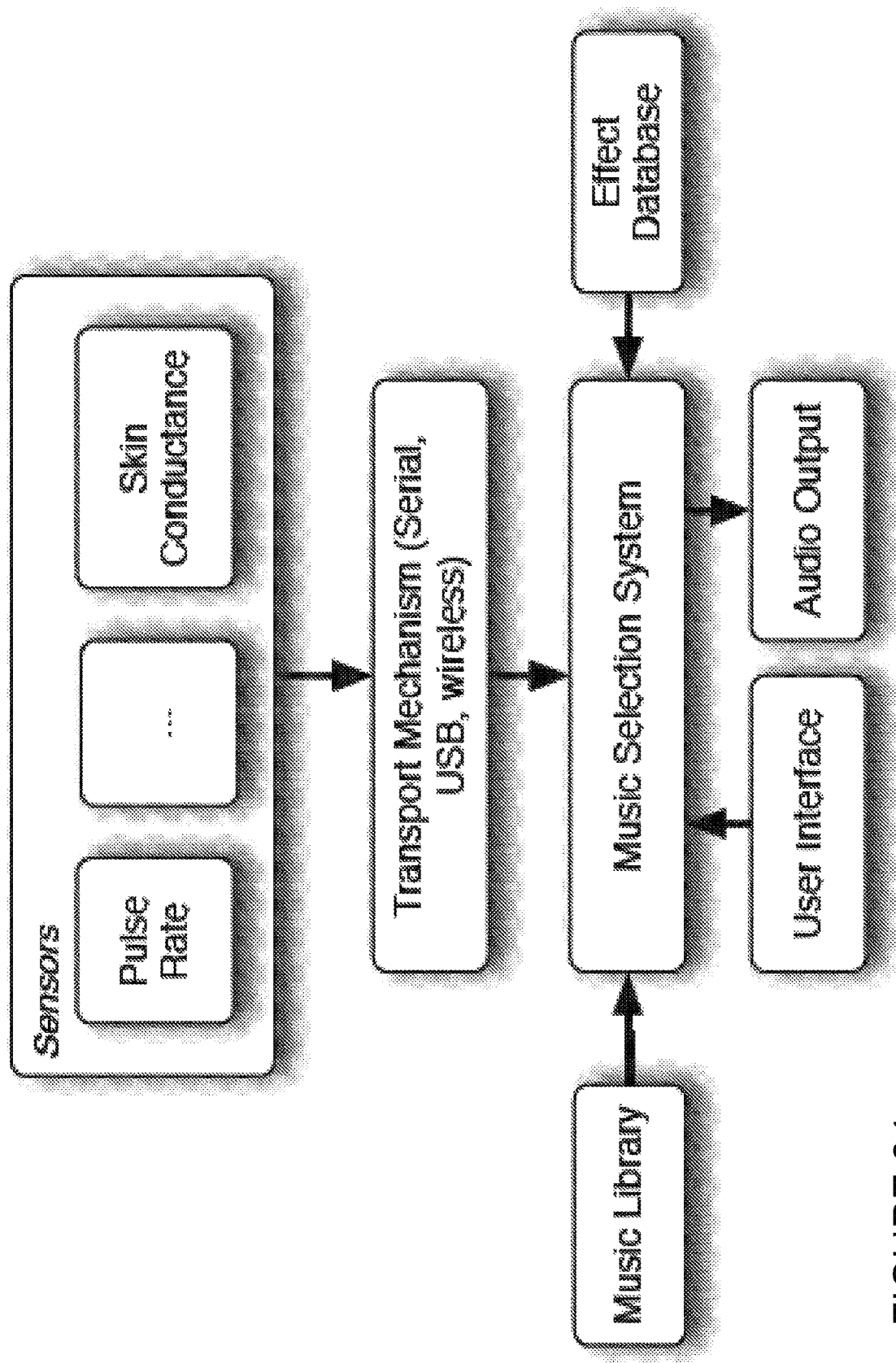
FIG. 24 is a detailed block-diagram showing the major components of the X-System music playback and monitoring application.

The music player may also be a software application which is downloadable from a software application store accessible via the internet. FIG. 24 summarises a design of the player system and the integration with the sensor subsystem. In an implementation, a player system and subsystem may be distributed across two or more computing devices; ubiquitous computing methods allied to mobile computing and personal human inputs may be employed, together with multiple ways of processing and delivering audio outputs, both private and public. So not only players, but also processors and human interaction devices, including but not limited to entrainment of interaction and control of a personal environment by emotional cues, as well as ordering or sequencing consumption may be used in an implementation.

G. Diagnostic and Streaming Software

When a sensor is used in System-X, then diagnostic and streaming software is capable of reading the values from the sensor(s) and determining a state of arousal of the user. The nature of skin conductance means that the absolute value can vary significantly due to how well it is in contact with the skin, from person to person and through normal sweating. To rectify this, the skin conductance value may be calibrated automatically based on the heart rate of the user.

The user of the system wears the system, selects a repertoire of music that they would like to listen to, decides what excitement level they would like to get to and puts on the sensors. Once a diagnosis has been made for the state of arousal of the user, this data along with the selected excitement level is used to select a program of tracks from the repertoire.

Optionally, the user selects a repertoire of music e.g. Jazz, Classical, Indian, World, Baroque), decides what their target arousal level should be (e.g. relaxed, excited, steady) and puts on the sensors. Once a diagnosis has been made of the current state of arousal of the user, repertoire is automatically selected to lead or "entrain" the listener from their current state to their chosen state of arousal. This is performed by defining a playlist, which entrains the user from the current emotional position in the multi-dimensional space defined by the INRM parameters, moving in small steps towards the defined position in INRM space defined as the desired end point.

H. Manual Categorisation

In an example, the repertoire has been categorised manually by a combination of pulse/metre detection using a metronome, and intuitive predictive judgements concerning levels of arousal and counterarousal associated with various musical parameters including rhythmicity, harmonicity, turbulence etc. e.g., the faster the pulse/metre the higher the arousal, the higher the harmonicity the lower the arousal. In the sample categorisation of FIG. 32 (from the Miles Davis repertoire) tracks are placed in one of five categories corresponding to levels of activation/arousal.

I. Manual Categorisation Vectors

By way of example, in other manual categorisations tracks are further sorted into stable, rising and falling vectors, e.g. "category 4 rising" will be selected if the user chooses a target state of high activation/arousal; "category 4 stable" would be selected if the uses wishes to remain in a state of moderate activation. For an example, see FIG. 33.

In the example of FIG. 34, movements from Beethoven symphonies have been categorized according to the vectors. Note that no movement was identified as appropriate for 4/stable or 2/stable.

Examples of the present invention have been described with reference to its effect upon human beings. However, the effect of music on animals is well documented. This almost certainly depends on simple psychoacoustic effects of sound environment, rather than a musical/biological discourse as such, but examples of the present invention may see applications in animal husbandry or veterinary medicine in addition to both general consumer, professional, athletic, wellness, healthcare and other markets.

J. Social Networks

In this application, X-System is adapted to facilitate the communication of neurophysiological state, arousal, affect and valency data, determined by X-System's algorithms, to friends via short range wireless and Bluetooth networks, as well as more widely to social networks such as Facebook and Twitter, and to health and care workers, as a diagnostic, monitoring or entrainment tool.

This application enables a range of navigational and communication applications on smartphones and other devices, allowing users to 'communicate and navigate innate states of arousal' (mood or emotion) and 'communicate and navigate experience'. It enables individual X-System users not only to see displays showing their own innate states, but to allow others to 'read' their true or unconscious states as they experience a variety of activities, from listening to music, to sports and recuperation and post-surgical care in health care settings.

A system and method for communicating X-System diagnostic capacity to decode neurophysiological states, adapting it to facilitate deeper, more direct communication about states of arousal and valency whilst engaging in a wide range of activities (including but not limited to music), between individuals and groups in social networks.

A system and method for generating information requests based on actual states of arousal (as measured by X-System), to search engines such as Google—this arousal information can then be used as an input to the search algorithm and also to the algorithms that control which advertisements are displayed (so for example, web users may be more receptive to advertisements for certain products when in specific arousal states and search results and advertisements can be tailored for maximum relevance using arousal state information. The arousal information can be used also to indicate 'presence' status information ("I am in a good mood, listening to Beethoven" etc.).

X-System categorises the innate neurophysiological 'state' of individuals in terms of both an unbroken continuum of data and discreet categories, ranging from 1 (high arousal) to 5 (counter-arousal). This is linked in core X-System applications to music selection.

In this 'social networking' or 'sharing' application, the innate 'state' arousal/counter arousal and valency data of an individual is transmitted over a variety of standard communication networks (including but not limited to Wi-Fi, Bluetooth, GSM, and other Mobile networks and fixed-line Internet) both directly and via wider social network systems (such as Facebook), to enable peer to peer and one to many communication of arousal, together (optionally) with coding that indicates concurrent music or other entertainment selection, or self-declared activity ('this is me watching a movie; responding to an advertisement; walking in the country; running, cycling'), all in real time, or near real time. For example, X-System detects emotional arousal parameters information of an audio track and then embeds this information into the audio track or into an electronic link to the audio track or as metadata associated with the track.

The X-System 'state' data can be distributed in real time snapshots (arousal and valency now); in real time streams (continuous flow); as history (arousal and valency yesterday), with or without data about the music selected at the time. This might be termed "a personal verve index" (verve: vivaciousness; liveliness).

The data will then be displayed as graphics, as colour codes, or in a variety of statistical forms. Users will be able to annotate the data and music with 'activity labels' (I was running at the time, or doing homework), which will open up other forms of analysis of the relationships between arousal, valency, music, other entertainment experiences and activity.

This application will enable individuals to search for people in their social networks who are in a similar mood, or engaged in similar activities, such as 'find people in my network who want to talk' or feeling down and yet keen to talk. This can be indicated by mood boards or to augment presence information on Facebook and other social networks.

With large volumes of users expressing their mood automatically generated by people who opt in (subject to say anonymity rules and permissioning about sharing), the data can indicate overall states of arousal amongst groups and larger communities.

The application will be extended to provide graphical and network maps showing patterns and cluster of moods amongst social groups, creating a 'social emotion' landscape for groups either engaged in their own individual activities, or groups together, in a social setting, such as at a party, or listening to a concert, or dancing.

This contrasts with early examples of social network analysis, which are limited by data mining and pattern matching derived from language and semantic analysis and so limited in their accuracy. X-System will generate more authentic and accurate interpretations of both individual and group arousal by capturing true innate neurophysiological state information.

This application will also be used to optimise web sites by linking X-System users to web cookies, such that if I am looking at a site and agree to the use of X-System readings of my innate state information, the cookies will generate analysis of the emotional impact of the site, or particular pages. This will enable web designers to experiment with a variety of textual, film, music and screen displays, layouts and experiences and get immediate feedback about users' emotional response.

This information will then be available to be matched to advertising and marketing metrics, such that responses to web experiences can be aligned with brand values and with the desired moods or desires that particular products and services aim to create. So, for example, the feedback mechanism might be used to match the emotional response to an advertisement about a particular car.

This extension of X-System's core algorithms creates a new form of communication, operating at a deep level, beyond culturally bound, linguistic expressions of mood, optionally linking it to current activity including choices of music, other entertainment and other activities.

This communication of unconscious, pre-linguistic levels of arousal, affect and valency opens up a new paradigm for social networking and health care diagnostics. In care settings, for example, monitoring patients' 'state' information will provide insights otherwise not possible using conventional diagnostic techniques. X-System may be integrated with a variety of conventional medical, care and diagnostic devices and applications to create a more holistic picture of patient condition and emotional state.

The X-System core data about innate arousal, valency and music selection is transmitted via standard interfaces to widely available social networks such as Facebook and Twitter and direct to Smartphones in local networks.

X-System will be embedded in Smartphones and other devices, in a variety of combinations of software, firmware and chip hardware. The X-System API will enable specialist App developers to create a variety of tools and techniques to leverage the flow of 'state' information, creating feedback and monitoring services.

There are many protocols and systems for the transmission of data and interfaces to social networks and Smartphones. This application of X-System is unique in that it enables these systems to be extended with new data that is otherwise not available. X-System is extended to target communication of innate arousal and valency with accompanying data indicating concurrent music, other entertainment or self-declared activity to individuals and groups in local, wide area and social networks.

X-System can also share arousal values, associated with a user interacting with a search engine such as Google®, with that search engine. The search engine can then use those values to optimise search and/or advertisement selection by the search engine.

X-System can also share arousal values associated with a user browsing a specific website or pages in a website with a website optimisation system so that the website optimisation system can use those values to optimise the website and/or specific pages (content, layout, sounds etc.).

K. Opportunities for Expansion/Enhancement

The main directions of product improvement and expansion are as follows:

Identification of emotional responses to music stimulated by memories or response to lyrics or other aspects of a song or piece of music rather than biology—developed by filtering out the expected physiological responses.

Sensor development and accessories, such as new generations of miniature Electroencephalography (EEG) brain scanning sensors. One possible approach is to include sensors (measuring any of the parameters discussed above, such as pulse, skin conductance etc) in earbuds or in gloves.

Advanced music search, navigation and discovery systems.

Advanced music search, navigation and discovery systems, including promotion, ordering, selection, and control interfaces.

Specialist medical applications.

Analysis of music to determine innate emotional responses; and

Capture and analysis of sensor data from early adopters to fine-tune level of arousal.

There are two further strategies for refining analytical functions. The first is through large-scale usage of the system. It is proposed to recruit one hundred volunteers to test the system in five phases. Their physiological data during listening, including heart rate and skin conductance readings, will be compared with automatic categorisation data and the results of manual categorisation, as a means of identifying strengths and weaknesses in the automatic analysis process, both in the capture of data and in the combination of values.

The second strategy for refinement is through machine learning, making use of linear regressive and/or neural network approaches. Training phases will follow each of the five testing phases. This approach will have the value of both scrutinising existing values and their combinations, and building up an evolving resource of learnt information and procedure. It may not be possible to refine the automated classification significantly. If this proves to be the case, machine learning processes and statistical analysis will be used to generate the necessary refinement. Additionally, weaknesses in the automatic classification system can be corrected through gathering and analysing the actual measurements of the effects of specific tracks on users. Those skilled in the art will appreciate that both artificial intelligence (AI) and heuristic rules-based approaches, and iterative automation and testing methodologies, may be employed.

X-system could also be used to create and adjust 'mood' in retail environments, and/or in online communities, through the playback of suitable music. Individuals could be connected via web interfaces to generate a common response/reading.

Similarly, X-System could be used in the understanding of and the matching of emotional responses to brands—essentially using X-System as a tool by which to diagnose and then shape emotional responses to brands by associating those brands with exactly the right kind of music for the target audience. X-System can be used in judging the response of different social groups to brand music.

Using polling or similar crowd-sensing techniques, X-System can also be used as a dynamic group entrainment tool in group environments, to select music which heightens arousal, for example at sports or entertainment events, and to reduce group tension and frustration in public environments such as transport, hospitals and government buildings.

L. Benefits of X-System

This technology is anticipated to have broad social, psychological and biological benefits in the reduction of stress, the treatment of insomnia, in optimising concentration and learning, in improving creative thought, and in facilitating optimal exercise patterns, whether for the general population or to support training regimes for elite athletes, and enhance event competitiveness.

X-System may be applied in therapeutic approaches to specific medical conditions. There is a large body of literature that provides evidence of the efficacy of music medicine and music therapy as complementary support in the treatment of conditions such as chronic pain, dementia, Parkinsons disease, depression, post-traumatic stress disorder and aphasia, and in palliative, post-surgical, post-stroke care. Possible benefits include reduction of bed rest after surgery, and reduction of drug use.

As an example, Jane would like to be able to concentrate better on the task at hand, so she slips on the wireless sensor wristband, touches the "concentrate" symbol on her iPhone and listens as she gets on with her work. The system will monitor her state of mind and body and play music suitable for maintaining an appropriate level of concentration.

It should be noted that in addition the automatic categorisation algorithms of X-System have considerable potential market value as a "stand alone", independent of the sensor technology, capable of offering an "emotional" navigation capacity for music streaming systems.

The invention may be used beneficially to select and categorise music according to its neuro-physiological effect, including but not limited to the ordering/sequencing, use, promotion, purchase and sale of music according to its neuro-physiological impact. The invention may also be used beneficially to link such categorisation to other categorisation schemes in common use.

Other potential uses of this system could be for selecting appropriate pieces of music from a database of library music for the soundtrack in films where a specific mood of the viewer is desired. It could also be used in visual arts, where a specific mood of the viewer is desired. Hence these applications would be visual applications or audiovisual applications, rather than just audio applications.

Related products and services will be generated from both of these areas to generate market intelligence about future trends in markets, i.e. products and services relating to analysis of music to determine innate emotional response, and capture and analysis of sensor data from early adopters to fine-tune level of arousal will be generated to generate intelligence about trends in future markets. Examples may include services to the computer game industry to assist in sound track selection to enhance the emotional experience of interactive gaming technology or as an aid to music composers seeking to elicit a particular response to either the whole of, or part of, a proposed musical composition.

APPENDIX 1

X-System Technical Outline: Component Overview

Fundamentally, the X-System is comprised of 3 components, two of which are software, and one which is hardware.

One piece of software (the "Music Analyser") is used in an offline (not directly linked to the real-time operation of the system) mode to analyse the candidate music files, and to build an estimation of their excitement/affect influence.

The second software part is the playback component. This is responsible for actually playing the music files, and also for receiving data from the sensor hardware, and using it to update its internal model which determines subsequent tracks to play.

Finally, the hardware component consists of a number of sensors which gather real-time data from the local environment, primarily from the actual user.

Detailed Descriptions

Music Analysis

The analysis aspect of the music analysis subsystem has been described in detail elsewhere, and is not covered here. This section covers only the integration aspects. As mentioned, this is expected to operate primarily in an offline, non-interactive fashion. It will be run periodically against a batch of music inputs, which will result in a set of values describing certain properties of the track. These values can also be combined to produce a single 'excitement' figure for the track, which is used by the playback system. The benefit of storing the components individually is that as data is gathered and used to tune system, excitement values can be recomputed with different coefficients without the need to re-analyse the entire track, greatly reducing overhead.

All outputs of the analysis will be stored in a database, indexed on a number of parameters, including at least track and artist identifiers, and some form of acoustic signature which is relatively tolerant of encoding differences or background noise.

These indexes will be used when a user 'imports' their music collection to the system. If any tracks already exist in the database, their values do not need to be recomputed.

The feedback process will be an opt-in system in which users agree to provide anonymised information about their usage of the system in order to improve it.

Automated features such as normalised change in arousal, replay/skip of suggested tracks, and aggregate sensor data can be used. Explicit feedback in the form of like/dislike acknowledgements, and occasional randomised questionnaires may also be used.

Use of feedback to guide system parameters may be on both a global and per-user basis. Large scale data mining, pattern recognition, machine learning systems will be used to improve affect/arousal estimation of music.

The analysis component will be operated as an internet accessible service, either in conjunction with some music streaming service to provide the audio, or purely as a control system operating with the users personal music collection.

Where fast & reliable internet service is available, significant fraction of the processing can be offloaded to the hosted X-system service. This allows more intensive processing than on a typical end-device, and also secures the analyser IP.

Additional Uses

Beyond the primary aim of 'Arousal Adjustment'—facilitating relaxation or excitement—there are other possible uses for the music analysis. It can be used to add an additional dimension to music discovery and navigation, by observing the effect of a large number of short music samples on a user, and then suggesting tracks or artists with similar characteristics. If the system has been used by someone for any reasonable time and has a well-adapted personal model, this initial step may be unnecessary. Similarity navigation of "Music like Artist/Album X" may also be possible based on features determined during track analysis.

Playback and Decision

The playback component handles 2 tasks. Controlling the music playback, and operating a real-time arousal analysis/ entrainment model, based on sensor input. The component may be responsible for actually playing the music, or may be a control layer on top of an existing media player such as iTunes/Windows Media Player, etc. The arousal analysis model will be based on the X-system INRM model, using the pre-computed values from the Music Analysis component as a starting point. The user will select a desired outcome, and the sensors will be used to gauge progress towards that outcome of each track. Explicit overrides will permit the user to manually skip a particular track either once, or to permanently blacklist it to ensure it will never be chosen again for them. In addition to their effect, these overrides will feed the decision model.

The capabilities of the component will be somewhat dependent on the environment it is operating in. On relatively low-power devices such as phones and portable music players, it may operate in a less precise, less computationally intensive mode, or if possible, offload some processing to a remote service.

For laptop/desktop/tablet applications, a more sophisticated model may be used. For niche uses, it may operate in conjunction with a visualiser or video playback component to enhance the entrainment effect.

It is likely that many users will wish to use the system from multiple different hosts, for example both their phone and laptop. The player requires some method of synchronising and sharing model data between these systems. This may be best implemented through (or on top of) some internet service similar to Apple iCloud or Google gDrive. This would also provide the channel for presenting data to the analysis system for modelling/training.

Additional Uses, Comments

Given enough training, it maybe possible to develop a version of the X-System that can operate at some level with no sensor feedback. This is likely to be less effective than a well-instrumented setup, but there may be sufficient value to the user in avoiding the complications of sensor purchase, upkeep, and inconvenience of wearing. If this proves impossible or undesirable, it may be possible to obtain some feedback through sensors without direct user attachment, for example a accelerometer in the phone carried in their pocket, or GPS in the same indicating their location.

Sensor Hardware

Currently, the sensing part of the system uses two distinct sensors. One is a pulse oximeter, which is used to monitor heart-rate, and the other is a skin conductance sensor, which measures the electrical conductance (the inverse of resistance) of the skin.

Pulse Oximeter

The pulse oximeter operates on the principle of wavelength-dependent absorption of light by the (oxy-)haemoglobin in the bloodstream. By comparing absorption values at red and infra-red wavelengths, the relative proportion of oxygenated blood can be determined, leading to the 'blood oxygen saturation' (spO2) figure. Tracking this value at a relatively high frequency allows detection of the sudden change which indicates a pulse due to a heart-beat, and hence, heart-beat rate can be determined. Whilst very useful in medical contexts, blood oxygenation does not change significantly or at timescales useful to the X-System, and only heart-rate data is collected.

The current system uses a COTS sensor, the Nonin 3150 WristOx2 wireless pulse oximeter. This device uses a soft rubber fingertip clip to house the light emitter/detectors, which is typical for the type of sensor. Alternatives exist which use sensors clipping gently to the lobe of the ear, as well as other parts of the body. This device uses Bluetooth (with the standard and generic SPP—Serial Port Protocol) for data transmission.

Future implementations of this sensor are likely to use sensor locations more convenient and less intrusive than a fingertip. The reliability and accuracy of the sensor is strongly improved by using direct transmission absorption (that is, directing light through a relatively thin body-part such as a finger or ear-lobe), but devices do exist which can operate in reflective mode, allowing them to be placed almost anywhere, although areas with high blood vessel density, and relatively close to the surface of the skin are to be preferred. One good site which fits well with the x-system goals would be as part of a watch strap, with the sensor on the inside of the wrist, where the buckle lies on a typical watch-strap.

Skin Conductance

Skin Conductance, variously termed EDA (Electro-Dermal activity), GSR (Galvanic Skin Resistance), or just Skin Resistance/Conductance, is a measure of the ability of the skin to carry electrical current. For obvious safety reasons, the current must be kept very low, and strictly limited. Baseline skin conductivity depends on a multitude of factors specific to individuals and their local environment, but on short timescales, the primary influence is that of sweat. Sweat, essentially just water high in electrolytes, is a good conductor, and its presence lowers the effective resistance of the skin. As an aside, Conductance (measured in Siemens/mhos) is defined as the inverse of resistance (in ohms). By convention conductance is used when describing these systems, although conversion to resistances is trivial.

Sweating is influenced by a variety of factors, but we are most interested in the relation to the parasympathetic nervous system. Increased arousal is strongly correlated with increased sweating, and hence increased skin conductance. This effect is relatively fast, on the order of seconds. The areas of the body with the highest density of sweat glands—the working surfaces of the hands and feet—are the most effective pickup locations, but other locations are possible, with varying results. The wrist and outer forearm have been shown to provide adequate results [ref available]

Measuring skin conductance can be achieved in several ways. The current sensor uses a simple potential divider with a high-precision resistor as one leg, and 2 skin contacts applied to the user serve as the other leg. The central node is also connected to a buffered ADC for measurement.

Other designs exist, and some prototype work has been done on using a Wheatstone Bridge—a particular circuit arrangement which allows highly precise differential measurements—to improve accuracy and noise rejection.

An important aspect of this parameter is that the value can vary over several orders of magnitude. Dry skin, in a cold, dry environment, can have conductances in the micro-Siemen (Mega-ohm) range, and extremely sweaty skin can go down to hundreds of milli-Siemen (1-1000 Ohms). Accurate measurement across this wide range presents some significant challenges in sensor design.

The existing sensor, as mentioned, uses a relatively unsophisticated potential divider. This is sampled at around 50 Hz by an Analogue-to-Digital Converter (ADC) integrated into the sensor microcontroller (MCU).

The particular MCU used at present is the Texas Instruments MSP430F2774. In addition to the ADC, this device contains an integrated programmable gain amplifier (PGA), which is used to magnify the signal from 1× to 16×. This provides an effective increase in precision of 4 bits to the existing 10-bit ADC. Preceding the amplifier is another integrated Op-Amp which is used in follower (unity-gain) mode, which acts to buffer the signal, and present a high-impedance load to the voltage divider, ensuring that the reading is not skewed due to significant current flowing through the sampling subsystem.

The ADC input is sampled at approximately 50 Hz. If the measured value falls into one of the two regions near the top and bottom of its full measurement range, the gain of the PGA pre-amp is adjusted to raise it towards the centre of the measurement range. Immediately following this adjustment (after a short settling period required by the amplifier) another sample is taken. A hysteresis method is implemented at the edge of each region to minimise the possibility of 'flip-flopping' repeatedly between 2 amplifier gain levels and interfering with the timely gathering of values. In addition, the relatively high sampling rate (50 Hz) compared to the transmission rate of approximately 2 Hz leaves plenty of room for amplifier adjustments. The high sample-rate readings are averaged using a simple low-pass (FIR) filter with a cutoff of 10 Hz.

Samples which fall into these border regions and result in an amplification change are discarded once this second sample completes. Software semaphores are used in the firmware to ensure the communication subsystem cannot access the sample buffer whilst it is in use or contains unreliable data.

If the reading falls into a buffer region but the pre-amp is already set to the maximum or minimum value possible, the reading is stored and transmitted, but marked with a flag indicating a potential saturation/clipping error.

The MCU is also connected to a wireless radio module, which it uses to communicate with a USB base-station. The wireless communications operate in the same unregulated frequency band as WiFi and Bluetooth, at 2.4 GHz. They are however of much lower power and data-rate, and are designed to co-exist with these other devices nearby.

Higher level radio communications are handled using a slightly modified version of the SimpliciTI proprietary network protocol on the sensor device and base station. This allows multiple sensors to operate in range of one another while ensuring that data is received by the correct base-station. Base stations are implemented using a second MSP430, this time with a USB interface, and which uses the standard USB-Serial device-driver which is supported by practically all host devices and operating systems. Layered on top of the network protocol is the X-System sensor protocol, which exists mainly to facilitate transmission of sensor readings, provide debugging output, and allow selective enabling/disabling of sensors to save power. The update frequency of the sensors can also be adjusted.

The sensors are battery powered, with in-situ charging possible over USB. This permits fully wireless operation, and minimises any noise that could be present in external power supply lines.

Notes

The above section describes the existing implementations, but there are a number of additional features planned, but not yet deployed. These include both upgrades to the current sensing modalities, and also the incorporation of additional types of sensor. Upgrades include:

Heart-rate:
  Reflective IR Pulse Oximeter suitable for wrist-mounted sensing.
  High frequency plethysmographic sampling for heart waveform & rhythm analysis, beyond a simple 'heart-rate' value.

Skin Conductance:
  Wheatstone Bridge based skin conductance pickup, with discrete or integrated precision instrumentation amplifiers.
  More sophisticated digital filtering stage
  Use of synchronised accelerometer attached to/near the skin contacts used to mark readings as suspicious due to contact-movement artifacts.

Additional modalities include:

EEG type sensors or 'caps' for brainwave activity

Electromyograph muscular tone/trigger rate

Multi-point ECG for high-resolution heart waveform

Breathing depth/rate

Eye-tracking/Gaze/blink analysis

Future sources of data which are not yet viable, but which would benefit the system include: stress hormone (e.g. Cortisol) plasma concentration, neural triggering rate, regional brain activity.

The primary obstacle to be overcome in the development of sensors is convenience. If aimed at a mass market, few users will tolerate cumbersome cables or obstructions of their hands or senses, in comparison to, for example, a therapeutic or medical market. Consolidation of sensors into a single package such as a wrist-watch or headphone style appliance would be ideal. Other possibilities include flexible circuits integrated into clothing or footwear.

A sensor package should be capable of interoperability with as many host devices as is feasible. This may include smart-phones, feature-phones, tablets, portable music players, laptops, desktops, home hifi, and in-car audio. The most common interfaces are likely WiFi or Bluetooth, although support varies significantly across the range of hosts described.

APPENDIX 2

Modelling Human Neuro-Physiological Response
  The following papers, which are incorporated by reference, provide information on modelling the neuro-physiological response of humans.
Aragon D, Farris C, Byers J F
The effects of harp music in vascular and thoracic surgical patients
Alternative Therapies in Health and Medicine 2002 September-October; 8(5): 52-4, 56-60
Baumgartner T, Lutz K, Schmidt C F, Jancke L
The emotional power of music: how music enhances the feeling of affective pictures
Brain Research 2006 February; 1075 (1): 151-64
Bernardi L, Porta C, Sleight P
Cardiovascular, cerebrovascular and respiratory changes induced by different types of music in musicians and non-musicians: the importance of silence
Heart (British Cardiac Society) 2006 April; 92(4): 445-52
Blood A J, Zatorre R J
Intensely pleasurable responses to music correlate with activity in brain regions implicated in reward and emotion
Proceedings of the National Academy of Sciences USA. 2001 Sep. 25; 98(20): 11818-23
Brown S, Martinez M J, Parsons L M
Passive music listening spontaneously engages limbic and paralimbic systems
Neuroreport 2004 Sep. 15; 15(13): 2033-7
Brugge J F
Patterns of organisation in auditory cortex
Journal of the Acoustical Society of America 78(½) 1985 353-359
Byers J F, Smyth K A
Effect of a musical intervention on noise annoyance, heart rate, and blood pressure in cardiac surgery patients
American Journal of Critical Care 1997 May; 6(3): 183-91
Cardigan M E, Caruso N A, Haldeman S M, McNamara M E, Noyes D A, Spadafora M A, Carroll D L
The effects of music on cardiac patients on bed rest
Progress in Cardiovascular Nursing 2001 Winter; 16(1): 5-13
Decety J, Chaminade T
Neural correlates of feeling sympathy
Neuropsychologia 41 2003 127-138
Evers S, Suhr B
Changes of the neurotransmitter serotonin but not of hormones during short time music perception
European Archives of Psychiatry and Clinical Neuroscience 2000; 250(3): 144-7
Formisano E, Kim D S, Di Salle F, van de Moortele P F, Ugurbil K, Goebel R
Mirror-symmetric tonotopic maps in human primary auditory cortex
Neuron 40(4) 2003 859-869
Gallese V
The roots of empathy. The shared manifold hypothesis and the neural basis of intersubjectivity
Psychopathology, 36 2003 171-180
Gerra G, Zaimović A, Franchini D, Palladino M, Giucastro G, Reali N, Maestri D, Caccavari R, Delsignore R, Brambilla F
Neuroendocrine responses of healthy volunteers to 'techno-music': relationships with personality traits and emotional state
International Journal of Psychophysiology 1998 January; 28(1): 99-111
Grape C, Sandgren M, Hansson L O, Ericson M, Theorell T
Does singing promote well-being?: An empirical study of professional and amateur singers during a singing lesson Integrative Physiological and Behavioral Science 2003 January-March; 38(1): 65-74

Griffiths T D, Buchel C, Frackowiak R S, Patterson R D
Analysis of temporal structure in sound by the human brain
Nature Neuroscience 1(5) 1998 422-427

Hebert S, Beland R, Dionne-Fournelle O, Crete M, Lupien S J
Physiological stress response to video-game playing: the contribution of built-in music
Life Sciences 2005 Apr. 1; 76(20): 2371-80

Holstege G, Bandler R, Saper C B (ed)
The emotional motor system
Progress in Brain Research 107, Elsevier, Amsterdam 1996

Iwanaga M
Relationship between heart rate and preference for tempo of music
Perceptual and Motor Skills 1995 October; 81(2): 435-40

Iwanaga M, Kobayashi A, Kawasaki C
Heart rate variability with repetitive exposure to music
Biological Psychology 2005 September; 70(1):61-6

Iwanaga M, Tsukamoto M
Effects of excitative and sedative music on subjective and physiological relaxation
Perceptual and Motor Skills 1997 August; 85(1): 287-96

Jeannerod M
Visual and action cuescontribute to the self-other distinction
Nature Neuroscience 7(3) 2004 421-422

Knight W E Rickard N S
Relaxing music prevents stress-induced increases in subjective anxiety, systolic blood pressure and heart rate in healthy males and females
Journal of Music Therapy 2001 Winter; 38(4): 254-72

Koelsch S, Fritz T, V Cramon D Y, Muller K, Friederici A D
Investigating emotion with music: an fMRI study
Human Brain Mapping 2006 March; 27(3): 239-50

Kumar A M, Tims F, Cruess D G, Mintzer M J, Ironson G, Loewenstein D, Cattan R, Fernandez J B, Eisdorfer C, Kumar M
Music therapy increases serum melatonin levels in patients with Alzheimer's disease
Alternative Therapies in Health and Medicine 1999 November; 5(6): 49-57

Lee D N
Guiding movement by coupling taus
Ecological Psychology 1998: 10(3-4): 221-250

Lee O K, Chung Y F, Chan M F, Chan W M
Music and its effect on the physiological responses and anxiety levels of patients receiving mechanical ventilation: a pilot study
Journal of Clinical Nursing 2005 May; 14(5): 609-20

Li L, Korngut L M, Frost B J, Beninger R J
Prepulse inhibition following lesions of the inferior collicus: prepulse intensity functions
Physiology and Behavior 1998 August; 65(1): 133-9

McAdams S, Winsberg S, Donnadieu S, De Soete G, Krimphoff J
Perceptual scaling of synthesised musical timbres: common dimensions, specidicities, and latent subject classes
Psychological Research 58 1995 177-192

Meloni E G, Davis M
The dorsal cochlear nucleus contributes to a high intensity component of the acoustic startle reflex in rats
Hearing Research 1998 May; 119(1-2): 69-80

Menon V, Levitin D J, Smith B K, Lembke A, Krasnow R D, Glazer D, Glover G H,
McAdams S
Neural correlates of timbre change in harmonic sounds
Neuroimage 17(4) 2002 1742-1754

Miluk-Kolasa B, Obminski Z, Stupnicki R, Golec L
Effects of music treatment on salivary cortisol in patients exposed to pre-surgical stress
Experimental and Clinical Endocrinology 1994; 102(2): 118-20

Mok E, Wong K Y
Effects of music on patient anxiety
AORN Journal 2003 February; 77(2): 396-7, 401-6, 409-10

Molnar-Szakacs I, Overy K
Music and mirror neurons: from motion to 'e' motion
Social Cognitive Affective Neuroscience 1 2006 235-241

Nilsson U, Unosson M, Rawal N
Stress reduction and analgesia in patients exposed to calming music postoperatively: a randomized controlled trial
European Journal of Anaesthesiology 2005 February; 22(2): 96-102

Osborne N 1.
Music for children in zones of conflict and post-conflict
in Communicative Musicality ed. Malloch and Trevarthen OUP 2009

Osborne N 2.
Towards a chronobiology of musical rhythm
in Communicative Musicality ed. Malloch and Trevarthen OUP 2009

Osborne N 3.
Neuroscience and real world practice . . .
Annals of the New York Academy of Sciences 2012 (in publication)

Overy K, Molnar-Szakacs I
Being together in time: musical experience and the mirror neuron system
Music Perception 26 2009 489-504

Pachetti C, Aglieri R, Mancini F, Martignoni E, Nappi G
Active music therapy and Parkinson's disease: methods
Functional Neurology 1998 January-March; 13(1): 57-67

Panksepp J, Trevarthen C
The neuroscience of emotion in music
in Communicative Musicality OUP 2009

Pantev C, Hoke M, Lehnertz K, Lutkenhoner B, Anogianakis G, Wittkowski W
Tonotopic organisation of the human auditory cortex revealed by transient auditory-evoked magnetic fields
Electroencephalographic Clinical Neurophysiology 69(2) 1988 160-170

Patterson R D, Uppenkamp S, Johnsrude I S, Griffiths T D
The processing of temporal pitch and melody information in the auditory cortes
Neuron 36(4) 2002 767-776

Penhune V B, Zatorre R J, Feindel W H
The role of auditory cortex in retention of rhythmic patterns as studied in patients with temporal lobe removals including Heschl's gyms
Neuropsychologia. 1999 March; 37(3):315-31

Peretz I
Listen to the brain: a biological perspective on musical emotions in Juslin P, Sloboda J (eds) Music and Emotion: Theory and Research OUP London 2001

Peretz I, Zatorre R J (ed)
The cognitive neuroscience of music OUP 2003

Peretz I, Kolinsky R
Boundaries of separability between rhythm in music discrimination: a neuropsychological perspective
The Quarterly Journal of Experimental Psychology 1993 May; 46(2): 301-25

Reinhardt U

Investigations into synchronisation of heart rate and musical rhythm in relaxation therapy in patients with cancer pain (in German)
Forschende Komplementarmedizin 1999 June; 6(3): 135-41
Rencanzone G H, Schreiner C E, Merzenich M M
Plasticity in the frequency representations of primary auditory cortex following discrimination training in adult owl monkeys
Neuroscience 13(1) 1993 87-103
Rizzolati G, Fogassi I, Gallese V.
Neuro-physiological mechanisms underlying the understanding and imitation of action
Nature Reviews Neuroscience, 2, 2001 661-670
Schneider N, Schedlowski M, Schurmeyer T H, Becker H
Stress reduction through music in patients undergoing cerebral angiography
Neuroradiology 2001 June; 43(6): 472-6
Stefano G B, Zhu W, Cadet P, Salamon E, Mantione K J
Music alters constitutively expressed opiate and cytokine processes in listeners
Medical Science Monitor 2004 June; 10(6): MS18-27
Sutoo D, Akiyama K
Music improves dopaminergic neurotransmission: demonstration based on the effect of music on blood pressure regulation
Brain Research 2004 Aug. 6; 1016(2): 255-62
Talavage T M, Sereno MIO, Melcher J R, Ledden P J, Rosen B R, Dale A M
Tonotopic organisation in human auditory cortex revealed by progressions of frequency sensitivity
Journal of Neurophysiology 91(3) 2004 1282-1296
Trevarthen C
Musicality and the Intrinsic Motive Pulse: Evidence from human psychobiology and infant communication
Special Issue of Musicae Scientiae: Rhythm, Narrative and Origins of Human Communication 1999: 157-213
Trevarthen C, Malloch S N,
The Dance of Wellbeing: Defining the Musical Therapeutic Effect
Nordic Journal of Music Therapy 2000; 9(2): 65-126
Turner R, Ioannides A A
Brain, music and musicality: inferences from neuroimaging in Communicative Musicality OUP 2009
Uedo N, Ishikawa H, Morimoto K, Ishihara R, Narahara H, Akedo I, Ioka T, Kaji I, Fukuda S
Reduction in salivary cortisol level by music therapy during colonoscopic examination
Hepato-gastroenterology 2004 March-April; 51(56): 451-3
Updike P A, Charles D M
Music Rx: physiological and emotional responses to taped music programs of preoperative patients awaiting plastic surgery
Annals of Plastic Surgery. 1987 July; 19(1): 29-33
Urakawa K, Yokoyama K
Music can enhance exercise-induced sympathetic dominancy assessed by heart rate variability
The Tohoku Journal of Experimental Medicine 2005 July; 206(3): 213-8
VanderArk S D, Ely D
Cortisol, biochemical, and galvanic skin responses to music stimuli of different preference values by college students in biology and music
Perceptual and Motor Skills. 1993 August; 77(1): 227-34
Warren J D, Uppenkamp S, Patterson R D, Griffiths T D
Separating pitch chroma and pitch height in the human brain
Proceedings of the National Academy of Sciences USA, 100(17) 2003 10038-10042
Wieser H G, Mazzola G
Musical consonances and dissonances: are they distinguished independently by the right and left hippocampi?
Neuropsychologia 1986; 24(6): 805-12
Yamamoto T, Ohkuwa T, Itoh H, Kitoh M, Terasawa J, Tsuda T, Kitagawa S, Sato Y
Effects of pre-exercise listening to slow and fast rhythm music on supramaximal cycle performance and selected metabolic variables
Archives of Physiology and Biochemistry 2003 July; 111(3): 211-4
Zatorre R J, Peretz I (ed)
The biological foundations of music
New York Academy of Sciences 2001
Zatorre R, J, Evans A C, Meyer E
Neural mechanisms underlying melodic perception and memory for pitch
Journal of Neuroscience 14(4) 1994 1908-1919
Note It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

The invention claimed is:

1. A computer implemented method for analysing sounds, such as audio tracks, and automatically classifying the sounds in a space in which arousal is one axis and valence is another axis; and the location of a sound or track in that arousal-valence space is automatically determined using a computer implemented system that analyses, measures or infers values for all of the following base feature parameters: harmonicity, turbulence, rhythmicity, sharpness, volume and linear harmonic cost; in which the turbulence is determined using an equation that links the turbulence to the harmonicity and energy during peak volume, and in which the linear harmonic cost arises from short-time Fourier transform (STFT) time slices whose fundamental frequency differs from that of the previous slice; in which the computer implemented system uses the analysed, measured or inferred values of the base feature parameters to locate the sound or track in that arousal-valence space.

2. The method of claim 1 in which values of some or all of the parameters for a sound or music track are plotted in the arousal-valence space and the location or region defined by those values predicts the emotion likely to be triggered by that sound or track.

3. The method of claim 1, in which values of some or all of the parameters for a sound or music track are plotted in the arousal-valence space and the location or region defined by those values predicts the emotion likely to be triggered by that sound or track.

4. The method of claim 1, in which the location of a sound or track in the arousal-valence space automatically determines how that sound or track is then used; or in which the location of the sound or track in that in the arousal-valence space is used to automatically predict a mood or emotion to be experienced by a listener to that sound or track.

5. The method of claim 1, in which an emotion is predicted by combining an automatically predicted arousal and valence value.

6. The method of claim 1, in which the predicted valence value is dependent on the predicted arousal value.

7. The method of claim 1, in which a neural network algorithm, which takes as input some or all of the base feature parameters, is used to output both a predicted neural net arousal and neural net valance.

8. The method of claim 1, in which an algorithm for predicting arousal is based on averaging the predicted arousal by a linear regression algorithm and a predicted neural net arousal by a neural network.

9. The method of claim 1,
   (i) in which for a high arousal value, a valence hypothesis algorithm uses the following base feature parameters as inputs: the harmonicity, 1 Hz turbulence and the rhythmicity; or
   (ii) in which for a medium arousal value, a valence hypothesis algorithm uses the following base feature parameters as inputs: the linear harmonic cost, the sharpness and the volume; or
   (iii) in which for low arousal value, a valence hypothesis algorithm uses the following base feature parameters as inputs: the linear harmonic cost, fundamental, the volume and 50 Hz turbulence.

10. The method of claim 1, in which an algorithm for predicting valence is based on the averaging of the neural net valence outputted by a neural network and the predicted valence generated by a valence hypothesis algorithm; or
   in which an algorithm for combining an automatically predicted arousal and valence value is based on plotting arousal and valence values on the X and Y axes of the arousal-valence space, in which the location on the arousal-valence space is associated with specific mood or emotion.

11. The method of claim 1, in which the base feature parameters and the outputs of the algorithms are averaged over one audio track.

12. The method of claim 1,
   (i) in which an audio track is also classified in terms of physical activity; or
   (ii) in which the location on the arousal-valence space is associated with a specific physical activity; or
   (iii) including the further step of automatically classifying a dataset of sounds or music in terms of their location in the arousal-valence space; or
   (iv) including the further step of automatically classifying music in terms of physical activities; or
   (v) including the further step of automatically constructing a playlist in terms of a preselected or desired mood or emotion to be experienced by a listener; or
   (vi) including the further step of automatically constructing a playlist in terms of preselected physical activity.

13. The method of claim 1,
   (i) including the further step of automatically streaming music depending on the listener's activity, such as working, exercising, driving, seeking pain relief, seeking relaxation, seeking mood enhancement; or
   (ii) including the further step of selecting sound or music to stream or otherwise provide to someone viewing online content.

14. The method of claim 1, in which the base feature parameters are derived from a neuro-physiological model of the functioning and response of one or more of the human lower cortical, limbic and subcortical regions in the brain to sounds.

15. The method of claim 1, in which the method is not genre sensitive.

16. The method of claim 1, in which a linear regression algorithm for predicting arousal is based on a combination of one or more or all of the base feature parameters, with weightings determined by linear regressions and that predict levels of neurophysiological arousal in the listener.

17. The method of claim 16 in which the linear regression algorithm also takes into account the genre or type of the sound or music track.

18. The method of claim 1, in which a valence hypothesis algorithm for predicting valence is based on a combination of subjective response and Heart Rate Variability data, which predicts how positive or negative the emotions of the listener are going to be; or in which a valence hypothesis algorithm using HRV (Heart Rate Variability) data is validated using empirical evidence that associates positive valence with high vagal power, as indicated by high HRV, and negative valence as low vagal power, as indicated by low HRV.

19. The method of claim 18 in which the valence hypothesis algorithm takes as an input one or more of the base feature parameters as well as the output of the linear regression algorithms.

20. The method of claim 1, in which the base feature parameters include one or more of the following: 50 Hz turbulence, 1 Hz turbulence, fundamental.

21. The method of claim 20 in which the base parameters that are used in calculating a valence value depend on the predicted arousal value.

22. The method of claim 1, in which a predicted arousal value by a linear regression algorithm is categorized into low, medium or high arousal values, which is then used by a valence hypothesis algorithm.

23. The method of claim 22 in which the valence hypothesis algorithm uses look up tables based on the category of the predicted arousal value by the linear regression algorithm.

24. The method of claim 1, including the further step of selecting sound or music to stream or otherwise provide to someone viewing or listening to online content to optimize the likelihood of that person reacting in a desired way to that content.

25. The method of claim 24, in which optimizing the likelihood of that person reacting in a desired way to that content includes reading or viewing or listening to that content, or purchasing goods or services advertised or promoted by that content.

26. The method of claim 1, implemented by a system including a processor programmed for automatically analysing sounds according to musical parameters derived from or associated with a predictive model of the neuro-physiological functioning and response to sounds by one or more of the human lower cortical, limbic and subcortical regions in the brain;
   and in which the system analyses sounds so that appropriate sounds can be selected and played to a listener in order to stimulate and/or manipulate neuro-physiological arousal and valence in that listener.

27. The method of claim 26,
   (i) in which the system predictively models primitive spinal pathways and the pre-motor loop (such as the basal ganglia, vestibular system, cerebellum), all concerned with primal responses to rhythmic impulses, by analysing beat induction, using a specifically calibrated onset window; or (ii) in which the system predictively models rhythmic pattern recognition and retention regions (such as the secondary auditory cortex of the temporal lobes) by using self-similarity/auto-correlation algorithms; or (iii) in which the system predictively models the activation of mirror neuron systems, which detect power, trajectory and intentionality of rhythmic activity, through one or more of: indices of rhythmic power, including computation of volume levels, volume peak density, "troughs", or the absence of energy and, dynamic profiles of performance energy; or (iv) in which the system predictively models activation of mirror neuron systems by analysing a profile of expenditure of energy (precipitous for high arousal, smooth for low) before and in between onsets, important mirror neuron information, by a computation of profiles of energy flow leading to significant articulations.

28. The method of claim 26, (i) in which the system predictively models the functioning and response of Heschl's Gyrus to sound by determining levels of harmonicity and inharmonicity; or (ii) in which the system detects a principal fundamental through calculation of the harmonic product spectrum, then establishes degrees of harmonicity both within and among spectra of different fundamentals; or (iii) in which detection of a principal fundamental and the establishment of degrees of harmonicity is applied both to instantaneous moments, and to progressions of pitches and spectra in time (related to the tonotopic mapping of the area around Heschl's Gyrus) and is expressed in terms of the linear harmonic cost, which represents both the rate at which the fundamental is changing, and the harmonic distance of the changes; or (iv) in which the system predictively models the neurophysiological sensing of simple timbre by Heschl's Gyrus, superior temporal sulcus, circular insular sulcus by analysing windows of harmonicity at instantaneous moments; or (v) in which the system predictively models melodic and harmonic progressions in terms of how far each STFT time slice deviates from simple ratios of the harmonic series; Time slices with no change in fundamental have a cost of zero; or (vi) in which the system combines indices of change in rhythmicity and harmonicity, with auditory brainstem and cortical activity innervating the amygdala, hippocampus and core emotional regions affecting neurotransmission and endocrine systems, including the HPA axis, dopamine circuits and levels of, for example, norepinephrine, melatonin and oxytocin; or (vii) in which the system determines the rhythmicity using an equation that relates R to B and S, such as the equation $R=\sqrt{B}*S^2$, and where R is the rhythmicity, B is beats per minute, and S is the mean of the beat strength; or (viii) in which the system determines the rhythmicity using an equation that relates I to C and H such as the equation $I=C/10-H$, where I is inharmonicity, C is linear harmonic cost and H is instantaneous harmonicity; or (ix) in which the system determines the turbulence using an equation that links T to H and P, such as $T=dH/dt*P$, where T is turbulence, H is harmonicity and P is energy during peak volume; or (x) in which the system determines the rhythmicity using an equation that relates R to B and S, and where R is rhythmicity, B is beats per minute, and S is the mean of the beat strength; or (xi) in which the system determines the rhythmicity using an equation that relates I to C and H, where I is inharmonicity, C is the linear harmonic cost and H is instantaneous harmonicity.

29. A computer implemented system configured to analyze sounds, such as audio tracks, and automatically classify the sounds in a space in which arousal is one axis and valence is another axis; and the location of a sound or track in that arousal-valence space is automatically determined by analyzing, measuring or inferring values for all of the following base feature parameters: harmonicity, turbulence, rhythmicity, sharpness, volume and linear harmonic cost; in which the turbulence is determined using an equation that links the turbulence to the harmonicity and energy during peak volume, and in which the linear harmonic cost arises from short-time Fourier transform (STFT) time slices whose fundamental frequency differs from that of the previous slice; in which the computer implemented system is configured to use the analysed, +-measured or inferred values of the base feature parameters to locate the sound or track in that arousal-valence space.

30. The system of claim 29, in which the analysis of sounds operates in real-time on locally stored music data and the system includes software embodied on a non-transitory storage medium, firmware embodied on a non-transitory storage medium and/or hardware running on a personal computing device.

* * * * *